(12) United States Patent
Natrajan et al.

(10) Patent No.: US 7,785,904 B2
(45) Date of Patent: *Aug. 31, 2010

(54) HIGH QUANTUM YIELD ACRIDINIUM COMPOUNDS AND THEIR USES IN IMPROVING ASSAY SENSITIVITY

(75) Inventors: Anand Natrajan, Manchester, NH (US); Qingping Jiang, East Walpole, MA (US); David Sharpe, Foxborough, MA (US); James Costello, Boston, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 277 days.

This patent is subject to a terminal disclaimer.

(21) Appl. No.: 11/764,924

(22) Filed: Jun. 19, 2007

(65) Prior Publication Data

US 2008/0014660 A1 Jan. 17, 2008

Related U.S. Application Data

(60) Division of application No. 11/142,938, filed on Jun. 2, 2005, now Pat. No. 7,309,615, which is a continuation-in-part of application No. 10/260,504, filed on Sep. 27, 2002, now Pat. No. 7,319,041.

(51) Int. Cl.
*G01N 33/533* (2006.01)
*G01N 21/76* (2006.01)
*G01N 33/53* (2006.01)
*C07D 219/00* (2006.01)

(52) U.S. Cl. .................. 436/546; 436/172; 436/805; 435/7.92; 435/968; 546/102

(58) Field of Classification Search .................. None
See application file for complete search history.

(56) References Cited

U.S. PATENT DOCUMENTS

| 5,593,845 | A  | * | 1/1997  | Akhavan-Tafti et al. ...... 435/7.9 |
| 6,783,948 | B1 | * | 8/2004  | Jiang et al. ..................... 435/18 |
| 7,083,986 | B2 | * | 8/2006  | Natrajan et al. ............. 436/546 |
| 7,309,615 | B2 | * | 12/2007 | Natrajan et al. ............. 436/546 |

FOREIGN PATENT DOCUMENTS

WO    WO 98/02421    *    1/1998

OTHER PUBLICATIONS

Akhavan-Tafti et al. Aryl N-alkylacridancarboxylate derivatives useful for chemiluminescent detection. STN international, HCAPLUS database, Accession No. 1997: 70326, document No. 126: 154813, RN No. 172834-47-8.*

* cited by examiner

*Primary Examiner*—Shafiqul Haq
(74) *Attorney, Agent, or Firm*—Kevin Stein

(57) ABSTRACT

The present invention relates to hydrophilic, high quantum yield acridinium compounds. It has been discovered that the placement of electron-donating groups in the acridinium ring system increases the amount of light that is emitted by the corresponding acridinium compound when its chemiluminescence is triggered by alkaline peroxide. More specifically, it has been found that the placement of one or two hydrophilic, alkoxy groups at the C-2 and/or C-7 position of the acridinium ring system of acridinium compounds increases their quantum yield and enhances the aqueous solubility of these compounds. The present hydrophilic, high quantum yield, acridinium compounds are useful chemiluminescent labels for improving the sensitivity of immunoassays.

15 Claims, 2 Drawing Sheets

HIGH QUANTUM YIELD ACRIDINIUM COMPOUNDS AND THEIR USES IN IMPROVING ASSAY SENSITIVITY

This application is a divisional of application Ser. No. 11/142,938 filed Jun. 2, 2005 which is a continuation-in-part of application Ser. No. 10/260,504 filed Sep. 27, 2002, both of which are hereby incorporated by reference in their entirety.

BACKGROUND OF THE INVENTION

1. Field of the Invention

The present invention relates to high quantum yield chemiluminescent acridinium compounds with increased light output. Structural features necessary for obtaining increased light emission from acridinium compounds are disclosed herein. Additionally, we also disclose hydrophilic versions of these structures, which not only have increased light output but also have increased water solubility and low nonspecific binding. These compounds because of their enhanced quantum yield and hydrophilic nature, are useful in improving assay sensitivity.

2. Background of the Invention

Chemiluminescent acridinium esters (AEs) are extremely useful labels that have been used extensively in immunoassays and nucleic acid assays. A recent review, Pringle, M. J., *Journal of Clinical Ligand Assay* vol. 22, pp. 105-122(1999) summarizes past and current developments in this class of chemiluminescent compounds.

McCapra, F. et al., *Tetrahedron Lett.* vol. 5, pp.3167-3172 (1964) and Rahut et al. *J. Org. Chem* vol. 301, pp. 3587-3592. (1965) disclosed that chemiluminescence from the esters of acridinium salts could be triggered by alkaline peroxide. Since these seminal studies, interest in acridinium compounds has increased because of their utility as labels. The application of the acridinium ester 9-carboxyphenyl-N-methylacridinium bromide in an immunoassay was disclosed by Simpson, J. S. A. et al., *Nature* vol. 279, pp. 646-647 (1979). However, this acridinium ester is quite unstable, thereby limiting its commercial utility. This instability arises from hydrolysis of the 9-carboxyphenyl ester linkage between the phenol and the acridinium ring.

Different strategies for increasing the stability of acridinium compounds have been described in the prior art. Law et al., *Journal of Bioluminescence and Chemiluminescence*, vol. 4, pp. 88-89 (1989) introduced two methyl groups to flank the acridinium ester moiety to stabilize this linkage. The resulting sterically stabilized acridinium ester, DMAE-NHS [2',6'-dimethyl-4'-(N-succinimidyloxycarbonyl)phenyl 10-methylacridinium-9-carboxylate] was found to have the same light output as an acridinium ester lacking the two methyl groups. The stability of the former compound when conjugated to an immunoglobulin was vastly superior and showed no loss of chemiluminescent activity even after one week at 37° C. at pH 7. In contrast, the unsubstituted acridinium ester only retained 10% of its activity when subjected to the same treatment. U.S. Pat. Nos. 4,918,192 and 5,110,932 describe DMAE and its applications.

The sterically-stabilized acridinium ester, DMAE-NHS has been used commercially in the ACS:180™ immunoanalyzer (Bayer Diagnostics). U.S. Pat. No. 5,656,426 to Law et al. discloses a hydrophilic version of DMAE termed NSP-DMAE-NHS ester. Both DMAE and NSP-DMAE are currently used in Bayer's ACS:180™ and Advia Centaur™ immunoanalyzers. The chemical structures of these compounds and the numbering system of the acridinium ring are illustrated in the following figures:

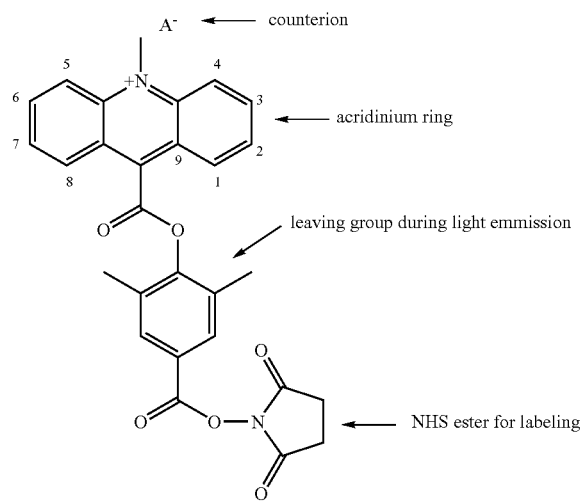

Structure of DMAE-NHS

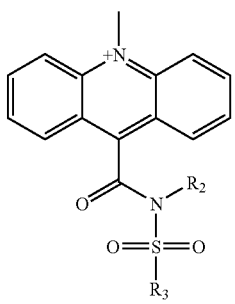

General structure of an acridinium sulfonamide (R2 and R3 are alkyl or aryl groups)

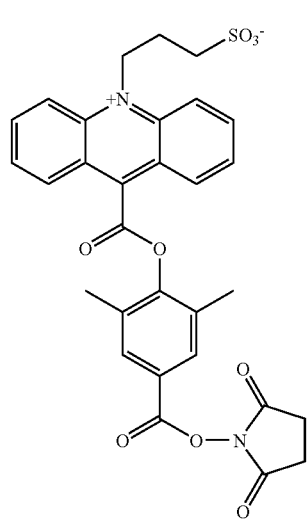

-continued

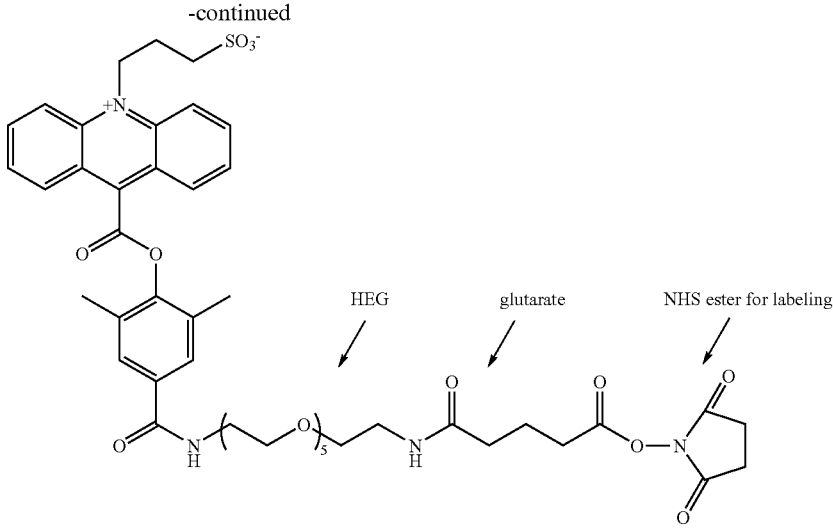

Because the acridinium ring is symmetrical, C-1 is equivalent to C-8, C-2 is equivalent to C-7, C-3 is equivalent to C-6, and C-4 is equivalent to C-5.

U.S. Pat. No. 6,664,043 B2 to Natrajan et al discloses NSP-DMAE derivatives with hydrophilic modifiers attached to the phenol. The structure of one such compound is illustrated in the above figure. In this compound a diamino hexa (ethylene) glycol (diamino-HEG) moiety is attached to the phenol to increase the aqueous solubility of the acridinium ester. A glutarate moiety was appended to the end of HEG and was converted to the NHS ester to enable labeling of various molecules.

A different class of stable chemiluminescent acridinium compounds has been described by Kinkel et al., *Journal of Bioluminescence and Chemiluminescence* vol. 4, pp. 136-139 (1989) and Mattingly, *Journal of Bioluminescence and Chemiluminescence* vol. 6, pp. 107-114 (1991) and U.S. Pat. No. 5,468,646. In this class of compounds, the phenolic ester linkage is replaced by a sulfonamide moiety, which is reported to impart hydrolytic stability without compromising the light output. In acridinium esters, the phenol is the 'leaving group' whereas in acridinium sulfonamides, the sulfonamide is the 'leaving group' during the chemiluminescent reaction with alkaline peroxide.

Light emission from acridinium compounds is normally triggered by alkaline peroxide. The overall light output, which can also be referred to as the chemiluminescence quantum yield, is a combination of the efficiencies of the chemical reaction leading to the formation of the excited-state acridone and the latter's fluorescence quantum yield.

A number of factors can influence the overall light output of acridinium compounds. The intrinsic chemiluminescence quantum yields of acridinium compounds are markedly affected by their structures. While most studies have focused on the effect of the leaving group on light emission, none have addressed the effect of functional groups on the acridinium ring on chemiluminescence quantum yields although their effects on the wavelengths of light emission have been well documented. See U.S. Pat. No. 6,355,803. Although, the synthesis of an acridinium ester with methoxy groups at C-2 and C-7 of the acridinium ring system has also been disclosed in U.S. Pat. No. 5,521,103, the effect of the two methoxy groups on either the quantum yield or wavelength of light emission of the acridinium ester was not disclosed.

DESCRIPTION OF THE PREFERRED EMBODIMENTS

Figure 1A:
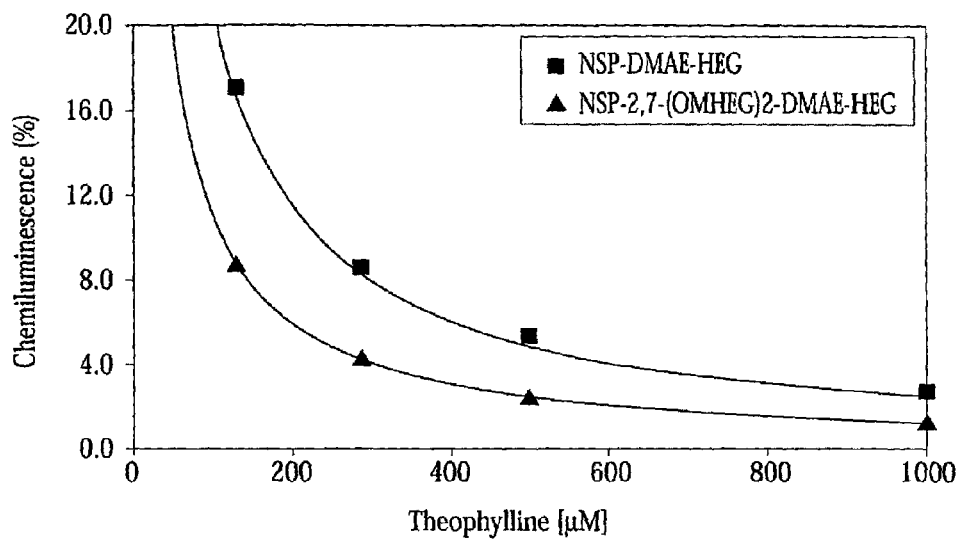
FIG. 1(a) is a graphical representation of the theophylline assay at high theophylline concentrations.

The present invention relates to acridinium compounds with enhanced quantum yields. It has been discovered that the placement of electron-donating groups in the acridinium ring increases the amount of light that is emitted by the corresponding acridinium compound when its chemiluminescence is triggered by alkaline peroxide. The concept of electron-donating groups is well known to practitioners in the field. Typically, an electron-donating group is a functional group, that is, an atom or a collection of atoms that, when compared to hydrogen, will donate electrons. A detailed discussion on electron-donating and electron-withdrawing groups can be found in Smith et al., *Advanced Organic Chemistry: Reactions, Mechanisms and Structure*, pp. 16-17 (5th Edition Wiley-Interscience).

More specifically, it has been found that the placement of one or two electron-donating functional groups, such as methoxy or alkoxy groups at C-2 and/or C-7 of the acridinium ring of acridinium compounds increases their quantum yield. Table 1 summarizes the relative quantum yields of various methoxy and alkoxy substituted acridinium compounds in relation to NSP-DMAE as well as their emission wavelength maxima. The chemical structures of representative acridinium compounds with electron-donating functional groups at the C-2 and/or C-7 position of the acridinium ring and corresponding acridinium compounds without electron-donating functional groups at the C-2 and/or C-7 position of the acridinium ring are listed in Table 1 and are structurally represented thereafter.

The acridinium compounds listed in Table 1 were synthesized using organic chemistry techniques well known to practitioners in the field. The acridinium ester NSP-DMAE, which does not have any electron-donating groups in the acridinium nucleus, was used as a reference compound. Information about the synthesis of the compounds in Table 1 can be found in the Examples. Light emission from each compound was measured using a luminometer equipped with a photomultiplier tube as the detector and the emission wavelength was measured using a FSSS (Fast Spectral Scanning System) camera from Photoresearch Inc.

TABLE 1

Relative Quantum Yields of Acridinium Compounds

| Compound | Relative quantum yield | Emission wavelength maximum, nm |
|---|---|---|
| 1. NSP-DMAE | 1 | 426 |
| 2. NSP-2-OMe-DMAE | 2.2 | 458 |
| 3. NSP-3-OMe-DMAE | 0.35 | 418 |
| 4. NSP-4-OMe-DMAE | 0.33 | 478 |
| 5. NSP-2,4-(OMe)$_2$-DMAE | 0.35 | 514 |
| 6. NSP-2,7-(OMe)$_2$-DMAE | 2.7 | 484 |
| 7. NSP-2,7-(OSP)$_2$-DMAE | 3.1 | 480 |
| 8. NSP-2,5-(OMe)$_2$-DMAE | 0.5 | 486 |
| 9. NSP-2,4,7-(OMe)$_3$-DMAE | 1 | 518 |
| 10. 2,7-(OMHEG)$_2$-DMAE | 1.5 | 480 |
| 11. NSP-2,7-(OMHEG)$_2$ DMAE | 3.3 | 480 |
| 12. NSP-AS | 1 | 426 |
| 13. NSP-2,7-(OMe)$_2$-AS | 1.7 | 484 |

Chemiluminescence was measured for 5 seconds on a Magic Lite Analyzer Luminometer (MLA1, Bayer Diagnostics). For quantum yield measurements, samples of the various compounds were prepared in 10 mM phosphate pH 8 containing 150 mM NaCl, 0.05% bovine serum albumin (BSA) and 0.01% sodium azide. For emission spectral determinations, samples were prepared in dimethyl formamide (DMF).

The chemical structures of the compounds listed in Table 1 are as follows:

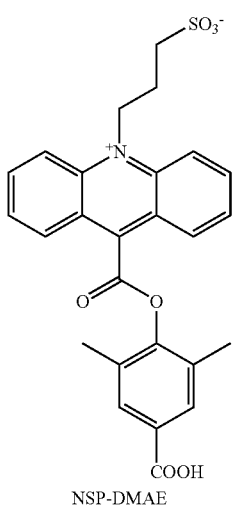
NSP-DMAE

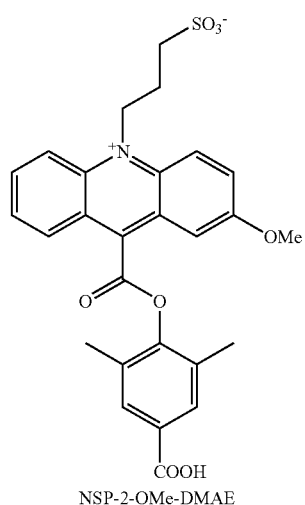
NSP-2-OMe-DMAE

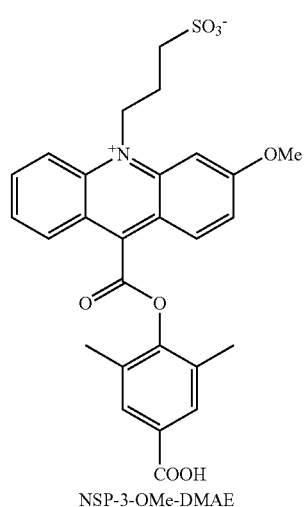
NSP-3-OMe-DMAE

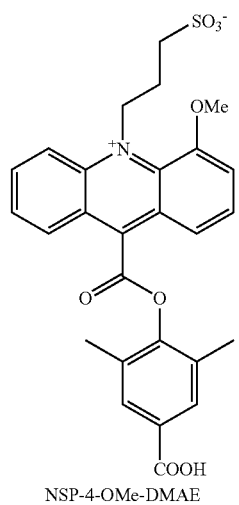
NSP-4-OMe-DMAE

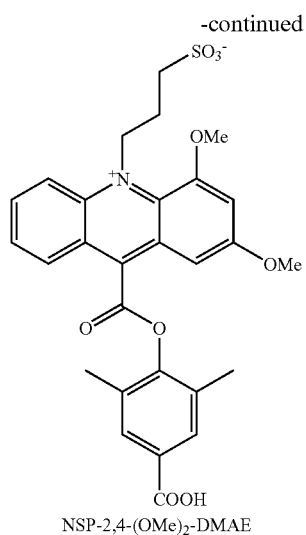
NSP-2,4-(OMe)₂-DMAE
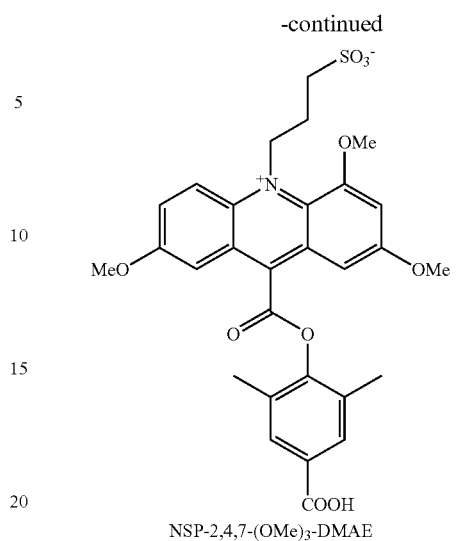
NSP-2,4,7-(OMe)₃-DMAE
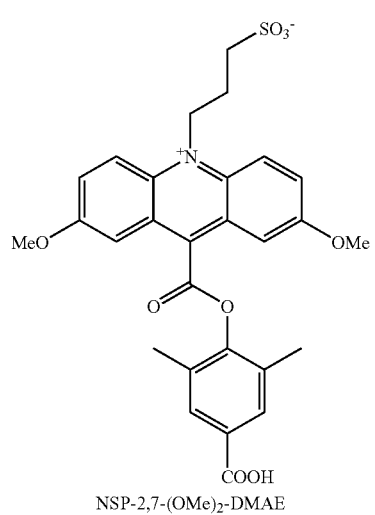
NSP-2,7-(OMe)₂-DMAE
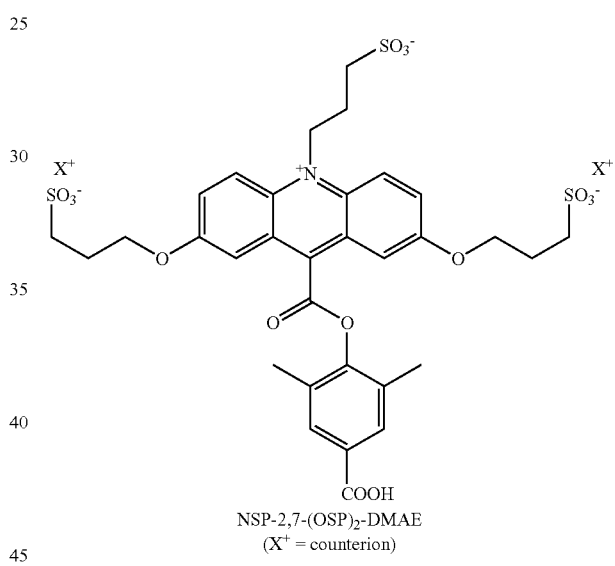
NSP-2,7-(OSP)₂-DMAE
(X⁺ = counterion)
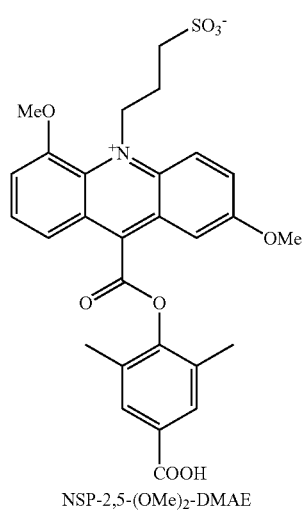
NSP-2,5-(OMe)₂-DMAE
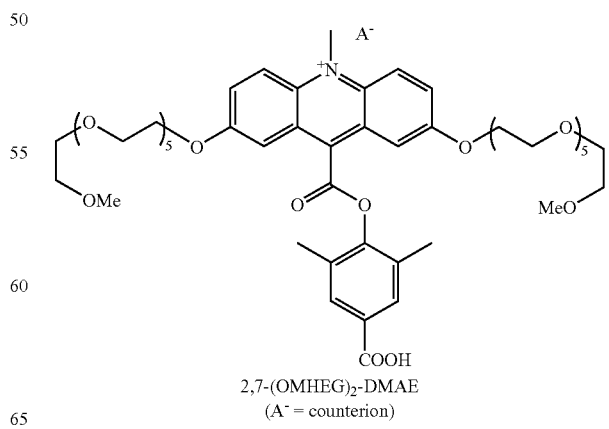
2,7-(OMHEG)₂-DMAE
(A⁻ = counterion)

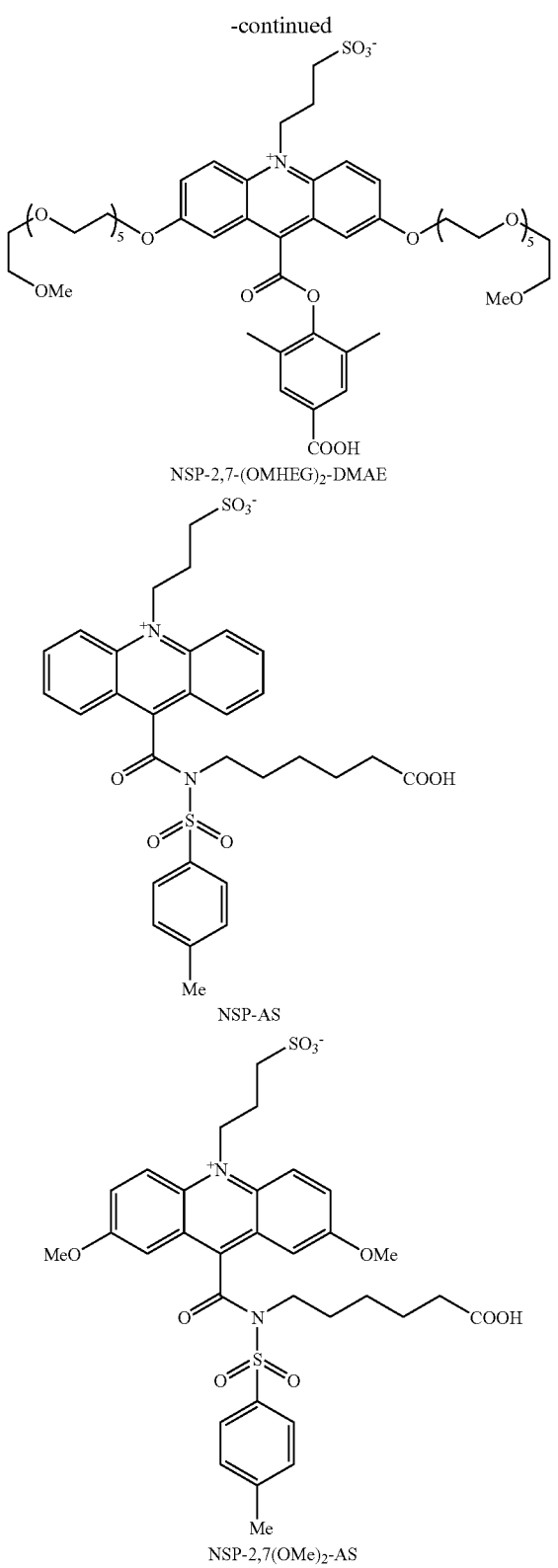

From an inspection of Table 1, it is evident that either a single methoxy group at C-2 or two methoxy groups at C-2 and C-7 of the acridinium ring, increase the light output from the corresponding acridinium compound. For example, NSP-2-OMe-DMAE has 2.2 times the light output of NSP-DMAE while NSP-2,7-(OMe)$_2$-DMAE has 2.7 times (270%) the light output of NSP-DMAE. Methoxy groups at other positions on the acridinium ring system do not lead to enhanced light emission. Thus, the finding that the specific placement of methoxy groups on the acridinium ring is required to obtain enhanced light yield is unexpected.

In addition to methoxy groups, other alkoxy groups ("OR"), wherein R can be alkyl, alkenyl, alkynyl, aryl, and aralkyl containing up to 20 heteroatoms, at C-2 and C-7 of the acridinium ring also lead to enhanced light emission. This finding is important because the structural components leading to enhanced light emission can be combined with hydrophilic groups to produce a hydrophilic, high quantum yield acridinium compound. For example, replacement of the two methoxy groups in NSP-2,7-(OMe)$_2$-DMAE with O-sulfopropyl groups ("OSP") in the compound NSP-2,7-(OSP)$_2$-DMAE also leads to enhanced light emission, that is, 3.1 times the light output of NSP-DMAE. Besides the O-sulfopropyl group, other hydrophilic groups such as the O-methoxy hexa(ethylene) glycol groups ("OMHEG") also lead to enhanced light emission.

Thus the two compounds 2,7-(OMHEG)$_2$-DMAE and NSP-(OMHEG)$_2$-DMAE emit 1.5 times and 3.3 times more light, respectively, than NSP-DMAE as shown in Table 1. In 2,7-(OMHEG)$_2$-DMAE, the acridinium nitrogen contains a methyl group whereas NSP-(OMHEG)$_2$-DMAE contains a sulfopropyl moiety. These observations clearly demonstrate that —OR groups in general can be used as electron-donating groups at these positions to obtain enhanced light emission. The key functional group substitution is thus the direct placement of electron-donating atoms at the C-2 and/or C-7 position on the acridinium nucleus.

A further advantage of the O-sulfopropyl groups as well as the OMHEG groups is that the resulting acridinium esters are extremely water soluble owing to the three sulfonate moieties or the methoxy hexa(ethylene)glycol moieties in these compounds. Other poly(ethylene) glycol moieties besides hexa(ethylene)glycol (HEG) can also be used. A high quantum yield acridinium ester that contains —OMTEG [O-methoxytri(ethylene)glycol] groups at C-2 and C-7 of the acridinium ring has also been synthesized as described in Example 10.

The acridinium sulfonamide with two methoxy groups at C-2 and C-7 also shows enhanced light emission in comparison to the unsubstituted acridinium sulfonamide. For example, NSP-2,7-(OMe)$_2$-AS emits 1.7 times more light than NSP-AS under identical conditions. Since the acridinium sulfonamide compounds contain a different leaving group than acridinium esters, the enhanced light emission obtained from NSP-2,7-(OMe)$_2$-AS clearly indicates that the leaving group does not play a critical role. The enhancement of quantum yield due to the presence of electron-donating groups at the C-2 and/or C-7 positions of the acridinium ring applies to both acridinium esters and acridinium sulfonamides.

The emission wavelength maxima of the various compounds listed in Table 1 show that the placement of methoxy or alkoxy groups at every position in the acridinium ring, except at C-3, leads to a shift to longer wavelength when compared to unsubstituted NSP-DMAE. However, there appears to be no simple correlation between emission wavelength maximum and quantum yield. For example, NSP-4-OMe-DMAE has an emission maximum of 478 nm and yet its quantum yield is only one third that of NSP-DMAE. A further point to note is that the nature of the alkyl group attached to the oxygen atoms at C-2 and C-7 does not appear to affect the emission wavelength maximum. Thus, NSP-2,7-(OMe)$_2$-

DMAE; NSP-2,7-(OSP)$_2$-DMAE and NSP-2,7-(OMHEG)$_2$-DMAE all have the same emission wavelength maxima.

In summary, Table 1 discloses acridinium compounds with specific structural components, such as the presence of an —OR group wherein R can be alkyl, alkenyl, alkynyl, aryl, and aralkyl containing up to 20 heteroatoms, at C-2 and/or C-7 of the acridinium ring, that contribute to enhanced light emission. A high quantum yield acridinium compound has a relative light yield greater than that of NSP-DMAE which is used as the reference compound in this study and is assigned a value of 1.

Acridinium compounds are used extensively in immunoassays and nucleic acid assays. Analytes that are typically measured in such assays are often substances of some clinical relevance and can span a wide range of molecules from large macromolecules such as proteins, nucleic acids, viruses bacteria, and the like, to small molecules such as ethanol, vitamins, steroids, hormones, therapeutic drugs, and the like.

A 'sandwich' immunoassay typically involves the detection of a large molecule, also referred to as macromolecular analyte, using two binding molecules such as antibodies. One antibody is immobilized or attached to a solid phase such as a particle, bead, membrane, microtiter plate or any other solid surface.

The methodology for the attachment of binding molecules such as antibodies to solid phases is well known in the prior art. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and microtiter plate. The second antibody is often covalently attached with a chemiluminescent or fluorescent molecule often referred to as a label. Labeling of binding molecules such as antibodies and other binding proteins are also well known in the prior art and are commonly called conjugation reactions and the labeled antibody is often called a conjugate. Typically, an amine-reactive moiety on the label reacts with an amine on the antibody to form an amide linkage. Other linkages such as thioether, ester, carbamate, and the like between the antibody and the label are also well known in the prior art.

In the sandwich assay, the two antibodies bind to different regions of the macromolecular analyte. The macromolecular analyte can be proteins, nucleic acids, oligosaccharides, antibodies, antibody fragments, cells, viruses, receptors, or synthetic polymers. The binding molecules can be antibodies, antibody fragments, nucleic acids, peptides, binding proteins or synthetic binding polymers. For example, the folate binding protein ("FBP") binds the analyte folate. Synthetic binding molecules that can bind a variety of analytes have also been disclosed by Mossbach et al. *Biotechnology* vol. 14, pp. 163-170 (1996).

When the solid phase with the immobilized antibody and the labeled antibody is mixed with a sample containing the analyte, a binding complex is formed between the analyte and the two antibodies. This type of assay is often called a heterogeneous assay because of the involvement of a solid phase. The chemiluminescent or fluorescent signal associated with the binding complex can then be measured and the presence or absence of the analyte can be inferred. Usually, the binding complex is separated from the rest of the binding reaction components such as excess, labeled antibody prior to signal generation. For example if the binding complex is associated with a magnetic bead, a magnet can be used to separate the binding complex associated with the bead from bulk solution.

By using a series of 'standards', that is, known concentrations of the analyte, a 'dose-response' curve can be generated using the two antibodies. Thus, the dose-response curve correlates a certain amount of measured signal with a specific concentration of analyte. In a sandwich assay, as the concentration of the analyte increases, the amount of signal also increases. The concentration of the analyte in an unknown sample can then be calculated by comparing the signal generated by an unknown sample containing the macromolecular analyte, with the dose-response curve.

In a similar vein, the two binding components can also be nucleic acids that bind or hybridize to different regions of a nucleic acid analyte. The concentration of the nucleic acid analyte can then be deduced in a similar manner.

In the assays described above, as the concentration of the analyte decreases, the amount of signal also decreases. At extremely low analyte concentrations, the ability to distinguish the specific signal of the label molecule associated with the binding complex, from 'noise' arising from non-specific binding of the labeled antibody to the solid phase, becomes increasingly difficult.

Non-specific binding is a common phenomenon and in assays it is measured as the signal in the absence of any analyte and often arises when the labeled-antibody binds to the solid phase in a random manner. To be able to measure the specific signal arising from a small concentration of analyte, this specific signal must be greater in magnitude than the signal associated with non-specific binding. Thus, to increase the sensitivity of an assay for an analyte, by which is meant the ability to detect and quantify very low amounts of an analyte, the specific signal must be increased and non-specific binding must be reduced.

A common strategy for improving the sensitivity of assays that employ chemiluminescent or fluorescent labels is to label one of the binding molecules with multiple labels in an attempt to increase the strength of the specific signal. However, this strategy has its own drawbacks such as an increase in non-specific binding which negates the gain in specific signal and moreover, multiple labeling of antibodies and nucleic acids can often have deleterious effects on their properties such as their ability to bind analytes as well as their solubility. For example, multiple labeling of antibodies with hydrophobic chemiluminescent or fluorescent labels can cause aggregation or precipitation of the antibody.

A more attractive approach to improving assay sensitivity is to enhance the chemiluminescent or fluorescent property of the label of interest. Accordingly, one objective of the present invention is the improvement of assay sensitivity by the use of high quantum yield, acridinium compounds. Another objective of this invention is the disclosure of hydrophilic, high quantum yield, acridinium compounds that not only have increased light output but are also extremely water-soluble and consequently, have low non-specific binding properties. Such chemiluminescent labels are unlikely to cause aggregation or precipitation of proteins and nucleic acids when compared to hydrophobic labels and offer a distinct advantage over conventional labels.

Finally, although multiple labeling strategies for signal amplification using hydrophobic labels are of limited utility, the present labels because of their hydrophilic nature may be more suited to such an approach. For example, a binding molecule such an antibody can be linked to another molecule which can serve as the label 'carrier'. In such a case, the binding molecule can be considered to be 'indirectly labeled' through the carrier.

The second molecule or carrier can be a protein or synthetic molecules such as polymers such as polyamino acids, or dendrimers that can be labeled with the chemiluminescent compound. By employing such a strategy, the properties of the binding molecule are segregated and preserved for the binding reactions, while the carrier molecule becomes the signal bearer for large increases in signal.

Conjugation of proteins to other proteins and polymers are well known in the prior art. A simple example of such an approach would be to label a protein such as bovine serum albumin (BSA) with multiple chemiluminescent labels and subsequently, covalently attach or conjugate the labeled BSA to an antibody for an analyte. The resulting labeled BSA-antibody conjugate when used in the assay is likely to generate greater amounts of signal by virtue of the multiple chemiluminescent labels on the BSA.

Another class of molecules that can be particularly suitable as carriers are dendrimers that are commercially available from Dendritech Inc. These dendrimers, by virtue of their small size in relation to the number of functional groups they carry for the attachment of labels, can be ideal carriers of chemiluminescent and fluorescent labels.

The attachment of the labeled carriers to the binding molecule or antibody can also be accomplished non-covalently. For example if the antibody molecule is labeled with biotin, then streptavidin with a chemiluminescent label can bind to the biotinylated antibody because of the strong affinity of streptavidin for biotin. The resulting antibody-streptavidin conjugate can then be used in an assay for an analyte.

Another class of immunoassays for small molecule analytes such as steroids, vitamins, hormones, therapeutic drugs or small peptides employs an assay format that is commonly referred to as a competitive assay. Typically, in a competitive assay, a conjugate is made of the analyte of interest and a chemiluminescent or fluorescent label by covalently linking the two molecules. The small molecule analyte can be used as such or its structure can be altered prior to conjugation to the label.

The analyte with the altered structure is called an analog. It is often necessary to use a structural analog of the analyte to permit the chemistry for linking the label with the analyte. A structural analog of an analyte is sometimes used to attenuate or enhance its binding to a binding molecule such an antibody. Such techniques are well known in the prior art. The antibody or a binding protein to the analyte of interest is often immobilized on a solid phase either directly or through a secondary binding interaction such as the biotin-avidin system described earlier.

The concentration of the analyte in a sample can be determined in a competitive assay by allowing the analyte-containing sample and the analyte-label conjugate to compete for a limited amount of solid phase-immobilized binding molecule. As the concentration of analyte in a sample increases, the amount of analyte-label conjugate captured by the binding molecule on the solid phase decreases. By employing a series of 'standards', that is, known concentrations of the analyte, a dose-response curve can be constructed where the signal from the analyte-label conjugate captured by the binding molecule on the solid phase is inversely correlated with the concentration of analyte. Once a dose-response curve has been devised in this manner, the concentration of the same analyte in an unknown sample can be determined by comparing the signal obtained from the unknown sample with the signal in the dose-response curve.

Another format of the competitive assay for small molecule analytes involves the use of a solid phase that is immobilized with the analyte of interest or an analyte analog and an antibody or a binding protein specific for the analyte that is conjugated with a chemiluminescent or fluorescent label. In this format, the antibody-label conjugate is captured onto the solid phase through the binding interaction with the analyte or the analyte analog on the solid phase.

The analyte of interest present in a sample then "competitively" binds to the antibody-label conjugate and thus inhibits or replaces the interaction of the antibody-label conjugate with the solid phase. In this fashion, the amount of signal generated from the antibody-label conjugate captured on the solid phase is correlated to the amount of the analyte in sample.

The high quantum yield acridinium compounds of the present invention when used in competitive assays for small molecule analytes offer the advantage of producing higher signals at all concentrations of analyte thereby facilitating the measurement of a wider range of analyte concentration. Thus, at high analyte concentration, when the amount of label-analyte conjugate captured by the binding molecule on the solid phase becomes very small, it is still possible to measure a discernible signal from a conjugate of a high quantum yield acridinium compound and the analyte.

The hydrophilic, high quantum yield acridinium compounds of the present invention are useful for the detection of macromolecular analytes in heterogeneous assays with improved sensitivity comprising the following steps:
a) providing a conjugate of a binding molecule specific for a macromolecular analyte with a hydrophilic, high quantum yield chemiluminescent acridinium compound containing electron donating functional groups at the C-2 and/or C-7 position of the acridinium ring;
b) providing a solid phase immobilized with a second binding molecule specific for said macromolecular analyte;
c) mixing the conjugate, the solid phase and a sample suspected of containing the analyte to form a binding complex;
d) separating the binding complex captured on the solid phase;
e) triggering the chemiluminescence of the separated binding complex by adding chemiluminescence triggering reagents;
f) measuring the amount of light emission with a luminometer; and
g) detecting the presence or calculating the concentration of the analyte by comparing the amount of light emitted from the reaction mixture with a standard dose response curve which relates the amount of light emitted to a known concentration of the analyte.

The hydrophilic, high quantum yield acridinium compounds of the present invention are also useful for the detection of small molecule analytes in heterogeneous assays with improved sensitivity comprising the following steps:
(a) providing a conjugate of an analyte with a hydrophilic, high quantum yield chemiluminescent acridinium compound containing electron donating functional groups at the C-2 and/or C-7 position of the acridinium ring;
(b) providing a solid phase immobilized with a binding molecule specific for the analyte;
(c) mixing the conjugate, solid phase and a sample suspected of containing the analyte to form a binding complex;
(d) separating the binding complex captured on the solid phase;
(e) triggering the chemiluminescence of the separated binding complex by adding chemiluminescence triggering reagents;
(f) measuring the amount of light with an luminometer; and
(g) detecting the presence or calculating the concentration of the analyte by comparing the amount of light emitted from the reaction mixture with a standard dose response curve which relates the amount of light emitted to a known concentration of the analyte.

The hydrophilic, high quantum yield acridinium compounds of the present invention are also useful for the detection of small molecule analytes in heterogeneous assays with improved sensitivity comprising the following steps:

a) providing a solid phase immobilized with an analyte or an analyte analog;
b) providing a conjugate of a binding molecule specific for the analyte with a hydrophilic, high quantum yield chemiluminescent acridinium compound containing electron donating functional groups at the C-2 and/or C-7 position of the acridinium ring;
c) mixing the solid phase, the conjugate and a sample suspected containing the analyte to form a binding complex;
(d) separating the binding complex captured on the solid phase;
(e) triggering the chemiluminescence of the separated binding complex by adding chemiluminescence triggering reagents;
(f) measuring the amount of light with an luminometer; and
(g) detecting the presence or calculating the concentration of the analyte by comparing the amount of light emitted from the reaction mixture with a standard dose response curve which relates the amount of light emitted to a known concentration of the analyte.

The chemiluminescence triggering reagents can be either hydrogen peroxide or peroxide salts.

The utility of hydrophilic, high quantum yield, acridinium compounds of the present invention is evident in heterogeneous immunoassays for two analytes. For example, theophylline is a small molecule analyte and the theophylline assay serves as an example of the competitive assays of the present invention. Thyroid stimulating hormone (TSH) is a macromolecular analyte that is commonly measured by immunoassays. The TSH assay is used as an example of the sandwich assays.

For the theophylline assay, the assay performance of two theophylline-acridinium conjugates was compared, the conjugate NSP-DMAE-HEG-theophylline described in U.S. Pat. No. 6,664,043 and the high quantum yield hydrophilic conjugate NSP-2,7-(OMHEG)₂-DMAE-HEG-theophylline described in Example 15.

The assay is described in Example 18 and the structures of the two conjugates are as follows:

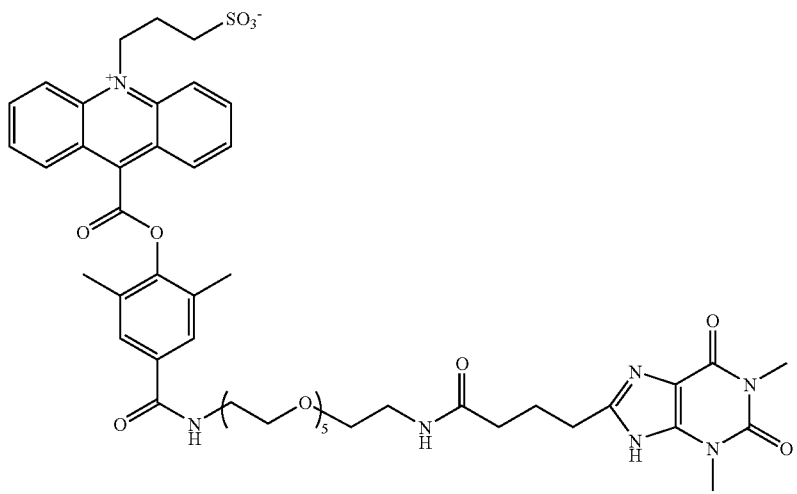

NSP-DMAE-HEG-Theophylline

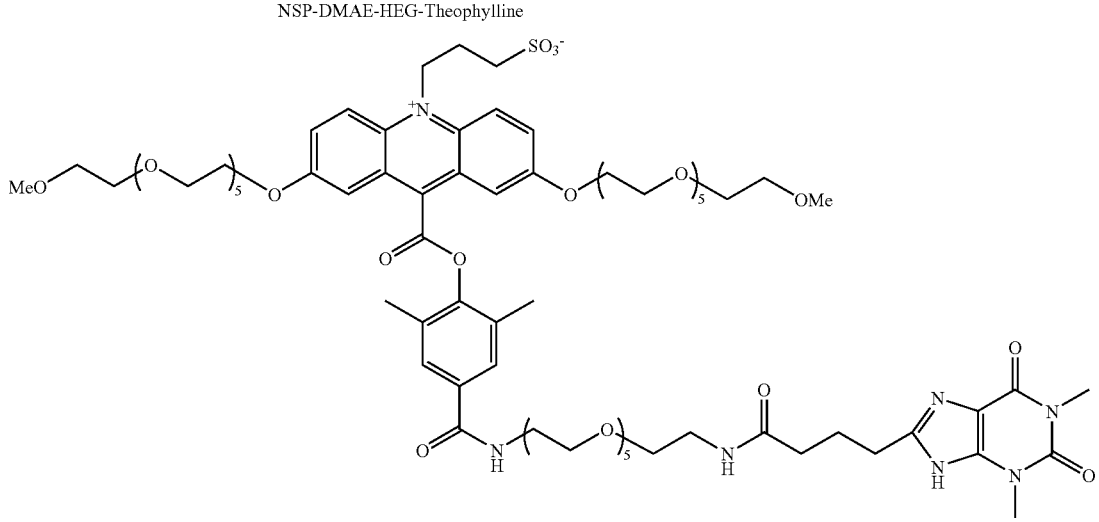

NSP-2,7-(OMHEG)₂-DMAE-HEG-Theopylline

The Bayer Diagnostics ACS:180® Theophylline Assay is one of a series of commercially marketed immunoassays manufactured by Bayer Diagnostics for application on the ACS:180® (Automated Chemiluminescent Immunoassay System).

The assay is a competitive immunoassay which uses a chemiluminescent acridinium compound conjugate of theophylline, NSP-DMAE-HEG-theophylline, for measurement of theophylline in a sample. In the theophylline assay, two reagents were mixed with the sample containing the analyte theophylline to start the assay. The first assay reagent is an anti-theophylline antibody immobilized on paramagnetic particles (PMP) which binds both the analyte, which is theophylline, and the theophylline-acridinium ester conjugates. The second assay reagent is the theophylline-acridinium ester conjugate.

Since the solid phase has a limited amount of the anti-theophylline antibody, the theophylline analyte in the sample and the theophylline-acridinium ester conjugate compete for binding to the antibody on the solid phase. Therefore, the amount of analyte in a sample is inversely correlated to the amount of the theophylline-acridinium ester conjugate that will bind to the solid phase in the assay.

The Bayer Diagnostics ACS:180® automatically performed the following steps for the theophylline Assay. First, 0.020 mL of each of fourteen samples was dispensed into a separate cuvet. A cuvet is an optically transparent or translucent container that holds the assay reagents and in which the assay takes place.

The fourteen samples each contained separate known amounts of theophylline. The amounts of theophylline given as concentrations in each of these fourteen samples were 0, 1.40, 2.10, 2.80, 4.20, 5.60, 9.21, 15.6, 32.7, 68.3, 129, 288, 500, and 1000 micromolar (uM). The amounts of theophylline given as numbers of molecules in each of these same fourteen samples were 0, 0.028, 0.042, 0.056, 0.084, 0.112, 0.184, 0.313, 0.655, 1.37, 2.59, 5.76, 10.0, and 2.00 picomoles ($10^{-12}$ moles), respectively.

Next, the ACS:180® dispensed the two assay reagents together into each cuvet and mixed the assay reagents with the sample within each cuvet. The first of the two assay reagents was 0.450 mL of solid phase, which contained 8.7 picomoles of anti-theophylline antibody on magnetically separable paramagnetic particles. The second of the two assay reagents was 0.100 mL of theophylline-acridinium ester conjugate, which was 0.026 picomole of acridinium compound conjugated to theophylline.

The assay proceeded for 7.5 minutes at 37° C. The Bayer Diagnostics ACS:180® finished the assay by magnetically separating the solid phase from other assay reagents, then removing fluid from the cuvet and then washing the solid phase in the cuvet with water. Chemiluminescence from the acridinium compound on the solid phase was initiated with subsequent light emission with the sequential additions of 0.30 mL each of Bayer Diagnostics ACS:180® Reagent 1 and Bayer Diagnostics ACS:180® Reagent 2. Reagent 1 was 0.1 M nitric acid and 0.5% hydrogen peroxide. Reagent 2 was 0.25 M sodium hydroxide and 0.05% cetyltrimethylammonium chloride.

Figure 1B:
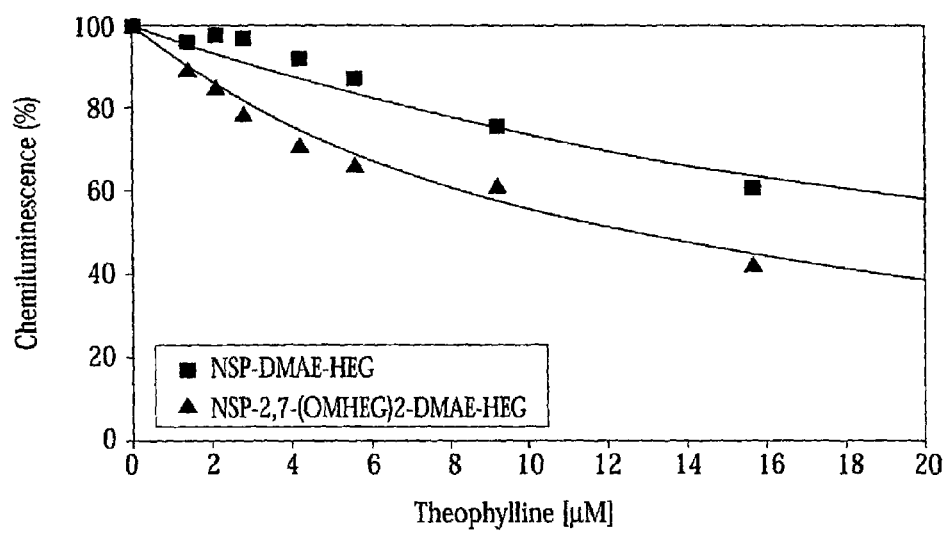
FIG. 1(b) is a graphical representation of the theophylline assay at low theophylline concentrations.

The Bayer Diagnostics ACS:180® measured the chemiluminescence in each cuvet with each cuvet corresponding to a single assayed sample as relative light units (RLUs). Normalization to percentage of chemiluminescence measured in the absence of analyte was calculated for comparison of the relative chemiluminescence given for each amount of analyte for the two theophylline-acridinium ester conjugates. The assay results are tabulated in Table 2 below and in graphical form in FIG. 1.

The spacing between chemiluminescence values for successive amounts of analyte is an indicator of assay sensitivity with greater spacing equating to greater sensitivity. This is well known to practitioners in the field. In the current assay, relative to the lower quantum yield label NSP-DMAE-HEG, the high quantum yield acridinium compound NSP-2,7-(OMHEG)$_2$-DMAE-HEG generated greater differentiation between samples containing small amounts of theophylline and no theophylline.

TABLE 2

Theophylline Assay

| Theophylline [µM] | Acridinium Compound Label | | | |
|---|---|---|---|---|
| | NSP-DMAE-HEG | | NSP-2,7-(OMHEG)2-DMAE-HEG | |
| | Chemiluminescence | | | |
| | (RLU) | (%) | (RLU) | (%) |
| 0 | 1846515 | 100 | 2493756 | 100 |
| 1.40 | 1774943 | 96.1 | 2237897 | 89.7 |
| 2.10 | 1806959 | 97.9 | 2115736 | 84.8 |
| 2.80 | 1790450 | 97.0 | 1959285 | 78.6 |
| 4.20 | 1698641 | 92.0 | 1770358 | 71.0 |
| 5.60 | 1609515 | 87.2 | 1647086 | 66.0 |
| 9.21 | 1391668 | 75.4 | 1523003 | 61.1 |
| 15.6 | 1119475 | 60.6 | 1056765 | 42.4 |
| 32.7 | 808738 | 43.8 | 682131 | 27.4 |
| 68.3 | 525335 | 28.5 | 395396 | 15.9 |
| 129 | 314966 | 17.1 | 217917 | 8.74 |
| 288 | 158037 | 8.56 | 107430 | 4.31 |
| 500 | 100707 | 5.45 | 61806 | 2.48 |
| 1000 | 51284 | 2.78 | 32293 | 1.29 |

The slope of the line generated for each tracer using the Bayer Diagnostics ACS:180® Theophylline Assay is an indicator of sensitivity. In the present assay, the high quantum yield acridinium compound label NSP-2,7-(OMHEG)$_2$-DMAE-HEG gave enhanced slope relative to the acridinium compound label NSP-DMAE-HEG at all concentrations of the analyte theophylline.

Assay sensitivity is often defined as the least measurable amount of analyte. The least measurable amount of analyte in the current competitive immunoassay is the amount of analyte corresponding to the greatest measured chemiluminescence that is less than the difference of the chemiluminescence measured in the absence of analyte minus two standard deviations of chemiluminescence measured in the absence of analyte. For example in competitive immunoassays where the following representations are given:

n=positive integer greater than 0.

x=the measured amount of analyte corresponding to y, where $x0<x1<x2<x3<\ldots<xn$ are successively greater measured amounts of analyte.

y=the chemiluminescence measured for an amount of analyte, represented by x, where $y0>y1>y2>y3>\ldots>yn$ are successively lesser values of chemiluminescence, measured for $x0<x1<x2<x3<\ldots<xn$, respectively.

x0=a zero amount of analyte or the amount of analyte equal to zero.

y0=the chemiluminescence measured for an amount of analyte equal to zero, which is x0.

s=one standard deviation of y0.

Then the sensitivity=xn for $yn<y0-2s$, when n=the least, positive, nonzero integer.

Using this definition, the sensitivity of the theophylline assay using the high quantum yield acridinium compound NSP-2,7-(OMHEG)$_2$-DMAE-HEG was 1.4 μM. The sensitivity of the assay using the acridinium compound NSP-DMAE-HEG was 4.2 μM. The quotient of 4.2 μM and 1.4 μM is 3.

The high quantum yield acridinium compound NSP-2,7-(OMHEG)$_2$-DMAE-HEG thus enhanced the sensitivity of the Bayer Diagnostics ACS:180® Theophylline Assay three-fold when compared to the acridinium compound NSP-DMAE-HEG.

The example clearly establishes that when used as chemiluminescent immunoassay labels the enhanced chemiluminescent light emission from high quantum yield acridinium compounds enhances the sensitivity of competitive immunoassays.

For the TSH assay, the assay performance of the acridinium ester NSP-DMAE-HEG-glutarate-NHS described in U.S. Pat. No. 6,664,043 was compared with the hydrophilic, high quantum yield acridinium compounds of the present invention, which is described in Example 19.

A comparison was made of the compounds NSP-2,7-(OMTEG)$_2$-DMAE-NHS, NSP-2,7-(OMTEG)$_2$-DMAE-HEG-glutarate-NHS, NSP-2,7-(OMHEG)$_2$-DMAE-AC-NHS and NSP-2,7-(OMHEG)$_2$-HEG-glutarate-NHS whose structures are shown below and whose syntheses are described in Example 9 (HEG-containing compounds) and Example 10 (TEG-containing compounds) respectively.

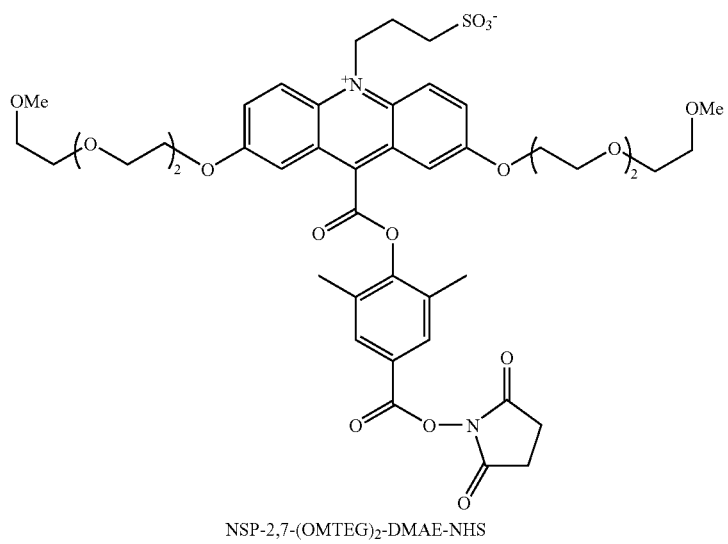

NSP-2,7-(OMTEG)$_2$-DMAE-NHS

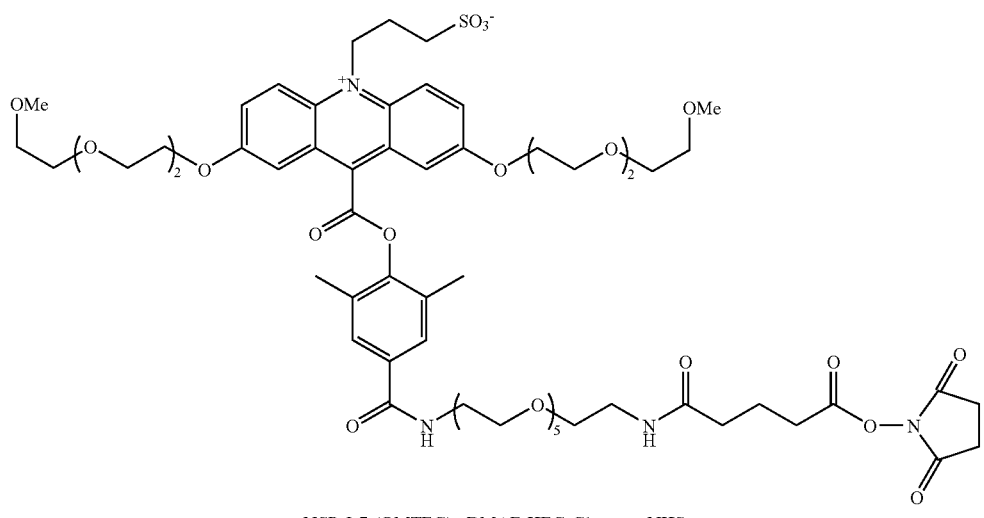

NSP-2,7-(OMTEG)$_2$-DMAE-HEG-Glutarate-NHS

-continued

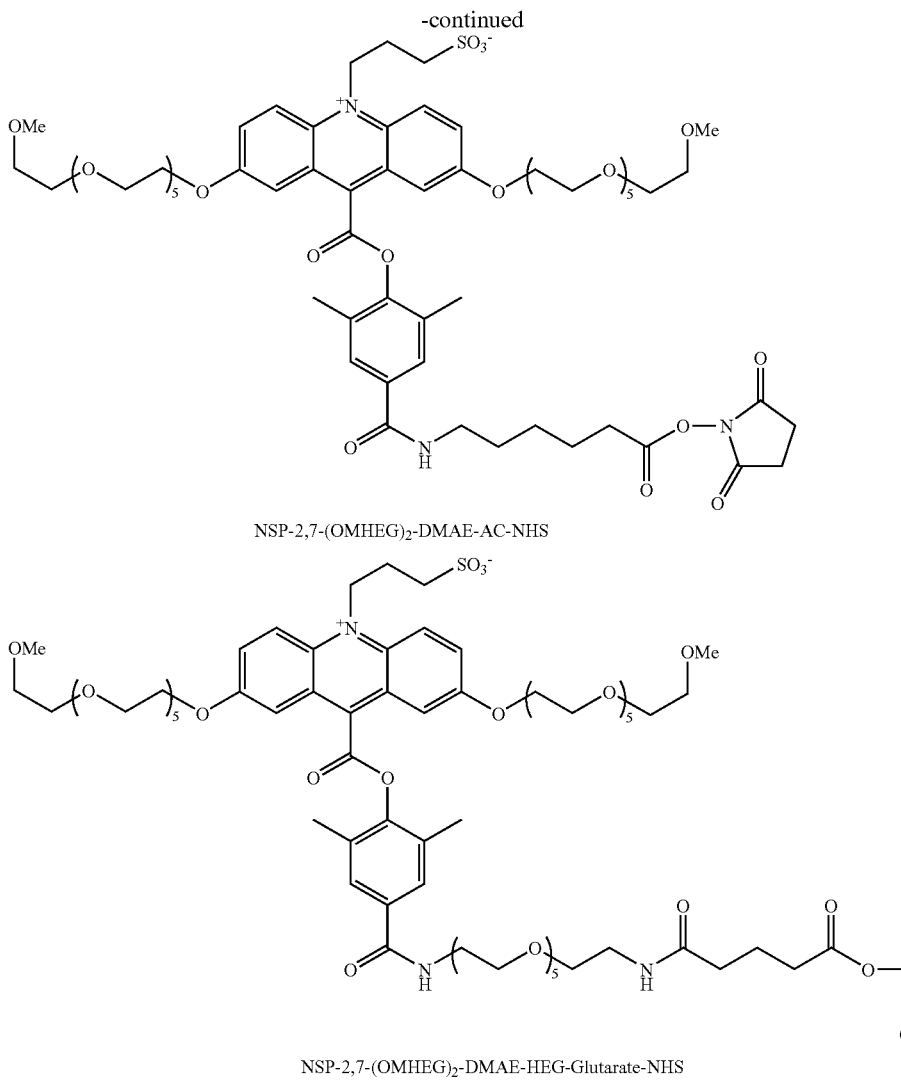

NSP-2,7-(OMHEG)$_2$-DMAE-AC-NHS

NSP-2,7-(OMHEG)$_2$-DMAE-HEG-Glutarate-NHS

The Bayer Diagnostics ACS:180® TSH3 assay is one of a series of commercially marketed immunoassays manufactured by Bayer Diagnostics for application on the ACS:180®. The TSH3 assay is a sandwich immunoassay which uses a chemiluminescent acridinium compound conjugate of an anti-TSH antibody, for measurement of the analyte TSH (Thyroid Stimulating Hormone) in a sample. In this assay there are two antibodies one of which is labeled with acridinium ester while the other is immobilized on paramagnetic particles (PMP).

In the assay, the two antibodies are mixed with the sample containing the analyte TSH to start the assay. This results in the binding of both the antibodies to the TSH analyte. As the concentration of the analyte TSH increases, a greater amount of the acridinium ester labeled antibody is bound to the solid phase. Thus, the concentration of analyte is directly correlated with the amount of chemiluminescent signal observed in the assay.

The ACS:180® automatically performed the following steps for the current TSH3 assay. First, 200 μl of each of twelve samples was dispensed into separate cuvets. The twelve samples each contained separate known amounts of TSH. The amounts of TSH given as concentrations in each of these twelve samples were 0, 0.002, 0.004, 0.010, 0.015, 0.020, 0.025, 0.030, 0.10, 1.0, 10 and 100 mIU/L. Next, the ACS:180® dispensed two assay reagents together into each cuvet and mixed the assay reagents with the sample within each cuvet. The first of the two assay reagents was 0.100 mL of a solution, which contained 0.22 picomoles of anti-TSH antibody conjugated with acridinium compound.

Both the high quantum yield acridinium compounds and NSP-DMAE-HEG-glutarate were tested separately as labels conjugated to the anti-TSH antibody. The conjugates were prepared and purified using the procedure described in example 16. The number of labels per antibody molecule for NSP-DMAE-HEG-glutarate, NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate were 8, 8, 7, 10 and 8 respectively.

Thus, all the conjugates contained an approximately equivalent number of labels. Therefore, any difference in assay performance can be correlated directly to the properties of the acridinium compound label.

The binding reaction proceeded for 2.5 minutes at 37° C. The second of the two assay reagents was 0.225 mL of solid phase, which was the other anti-TSH antibody conjugated to paramagnetic particles. The assay then proceeded for 5.0 minutes at 37° C. The assay was finished by magnetically separating the solid phase from other assay reagents, removing fluid from the cuvet and, washing the solid phase in the cuvet with water.

Chemiluminescence from the acridinium compound on the solid phase was initiated with subsequent light emission with sequential additions of 0.30 mL each of Bayer Diagnostics ACS:180® Reagent 1 and Bayer Diagnostics ACS:180® Reagent 2. The chemiluminescence in each cuvet was then measured as relative light units (RLUs) with each cuvet corresponding to a single assayed sample. The amount of analyte is correlated with the number of RLUs measured by the Bayer Diagnostics ACS:180®. The greater the amount of the analyte TSH in a sample, the greater the amount of RLUs that are measured.

In the current assay, the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced chemiluminescence for all amounts of analyte relative to the acridinium compound label NSP-DMAE-HEG-glutarate. The results of the assay are tabulated in Tables 3-5 and plotted graphically in FIG. 2.

current assay signal and noise were determined for each tested antibody-acridinium ester conjugate. The ratio of the signal divided by the noise in a sandwich immunoassay for a particular amount of analyte is an indicator of sandwich immunoassay sensitivity. The greater the signal to noise ratio for a particular amount of analyte in a sandwich immunoassay, the more distant is the corresponding signal from the noise and the better able is the assay to measure the difference between the signal and the noise.

In the current assay, the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced signal to noise ratios for the analyte relative to the label NSP-DMAE-HEG-glutarate for all concentrations of the analyte. The greater signal to noise ratios generated by the high quantum yield acridinium compound labels for both the high amounts and particularly the low

TABLE 3

TSH Assay using Acridinium Compounds as Labels

| TSH [mIU/L] | NSP-DMAE-HEG-glutarate | NSP-2,7-(OMTEG)$_2$-DMAE | NSP-2,7-(OMHEG)$_2$-DMAE-HEG-glutarate Chemiluminescence (RLU) | NSP-2,7-(OMHEG)$_2$-DMAE-AC | NSP-2,7-(OMHEG)$_2$-DMAE-HEG-glutarate |
|---|---|---|---|---|---|
| 0 | 12504 | 13492 | 20114 | 11871 | 12343 |
| 0.002 | 12831 | 14514 | 20185 | 12567 | 13973 |
| 0.004 | 13127 | 15567 | 22650 | 13084 | 14152 |
| 0.01 | 13680 | 17442 | 24519 | 13418 | 15493 |
| 0.015 | 14161 | 21150 | 25387 | 15268 | 17577 |
| 0.02 | 15106 | 21628 | 27810 | 16831 | 19542 |
| 0.025 | 15558 | 22920 | 29258 | 18547 | 21139 |
| 0.03 | 15750 | 23840 | 30872 | 20170 | 22404 |
| 0.1 | 20998 | 50110 | 66057 | 46578 | 58692 |
| 1 | 62108 | 306958 | 352706 | 286667 | 283798 |
| 10 | 553358 | 1916772 | 3147811 | 1867356 | 1999399 |
| 100 | 4350612 | 16861210 | 21937230 | 15763393 | 17584945 |

Noise is the portion of chemiluminescence in a sandwich immunoassay of a sample which is due to the non-specific binding of the labeled antibody to the solid phase and which is measured in samples that contain no analyte. Signal is the portion of the chemiluminescence due to the specific binding of the labeled antibody to the solid phase when analyte is present in the sample. The total chemiluminescence measured in the current TSH assay for samples that do contain analyte is the sum of signal plus noise, where signal is calculated as the difference of the total chemiluminescence minus the noise.

For the current assay, sensitivity is defined as the least measurable amount of analyte which corresponds to the least measured chemiluminescence that is greater than the sum of the noise plus two-standard deviations of the noise. In the amounts of TSH, relative to NSP-DMAE-HEG-glutarate, indicate an enhancement of sensitivity for the TSH assay.

Figure 2A:
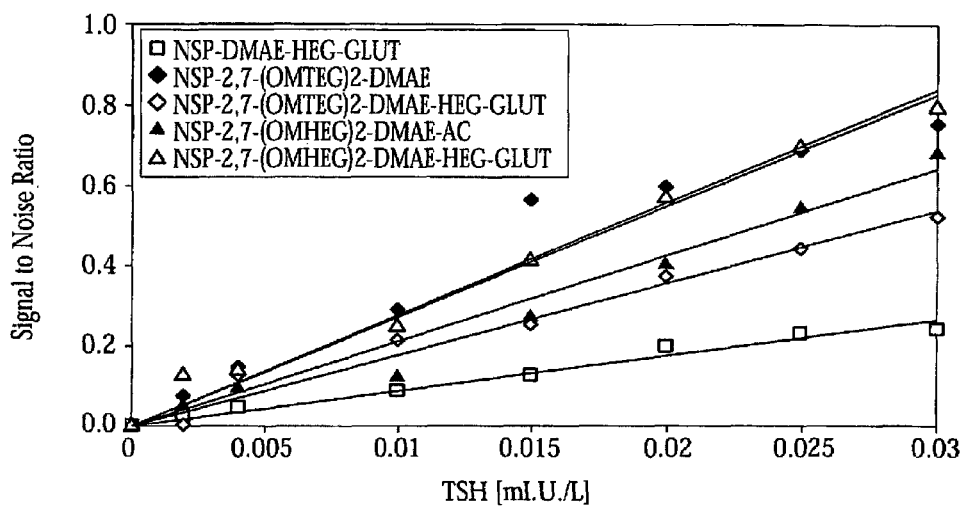
FIG. 2(a) is a graphical representation of the thyroid stimulating hormone (TSH) assay at low TSH concentrations.
Figure 2B:
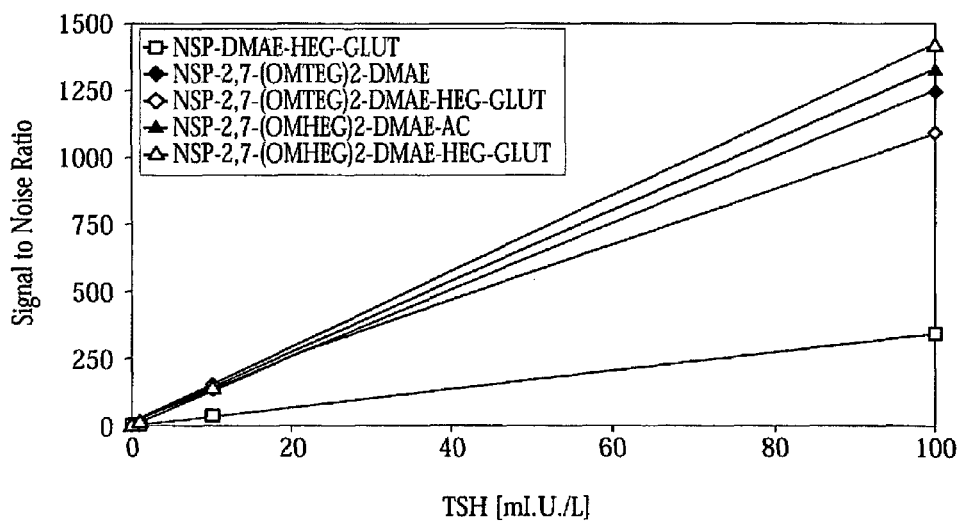
FIG. 2(b) is a graphical representation of the TSH assay at high TSH concentrations.

When the results of Table 3 are plotted in graphical form in FIG. 2, then the slope of the line generated for each antibody-acridinium ester conjugate is also an indicator of sensitivity. The greater the slope of the line, the more distant is the signal for a particular amount of analyte from the noise and the assay is better able to measure the difference between the signal and the noise. In the current assay, the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced slopes relative to NSP-DMAE-HEG-glutarate as is evident from FIG. 2. The slopes of the lines in FIG. 2 are tabulated in Table 4.

TABLE 4

TSH Assay Slopes using Acridinium Compounds as Labels

|  |  | NSP-DMAE-HEG-glutarate | NSP-2,7-(OMTEG)$_2$-DMAE | NSP-2,7-(OMTEG)$_2$-DMAE-HEG-glutarate | NSP-2,7-(OMHEG)$_2$-DMAE-AC | NSP-2,7-(OMHEG)$_2$-DMAE-HEG-glutrate |
|---|---|---|---|---|---|---|
| Low TSH Slope (RLU/[mI.U./L]) | from 0 to 0.03 mI.U./L TSH | 1.1E+05 | 3.4E+05 | 3.6E+05 | 2.8E+05 | 3.4E+05 |
| High TSH Slope (RLU./(mI.U./L]) | from 1 to 100 mI.U./L TSH | 4.3E+04 | 1.7E+05 | 2.2E+05 | 1.6E+05 | 1.7E+05 |

Assay sensitivity is often defined as the least measurable amount of analyte. In the current sandwich immunoassay the least measurable non-zero amount of analyte is the amount of analyte corresponding to the least measured chemiluminescence that is greater than the sum of the noise plus two-standard deviations of the noise. For example in sandwich immunoassays where the following representations are given:

n=positive integer greater than 0.

x=the measured amount of analyte corresponding to y, where x0<x1<x2<x3< . . . <xn are successively greater measured amounts of analyte.

y=the chemiluminescence measured for an amount of analyte, represented by x, where y0<y1<y2<y3< . . . <yn are successively greater values of chemiluminescence, measured for x0<x1<x2<x3< . . . <xn, respectively.

x0=a zero amount of analyte or the amount of analyte equal to zero.

y0=the chemiluminescence measured for an amount of analyte equal to zero, which is x0.

s=one standard deviation of y0.

Then the sensitivity=xn for yn>y0+2s, when n=the least, positive, nonzero integer.

The assay sensitivity in the current assay using the high quantum yield acridinium compound labels were enhanced as shown in Table 5 with the lower numbers indicative of a more sensitive assay. For example, using the hydrophilic, high quantum yield label NSP-2,7-(OMHEG)$_2$-DMAE-HEG-glutarate in the assay affords an assay sensitivity that is >7-fold more sensitive (0.015/0.002) when compared to the label NSP-DMAE-HEG-glutarate. The example clearly demonstrates that when used as labels, hydrophilic high quantum yield acridinium compounds enhances the sensitivity of sandwich immunoassays.

The enhanced sensitivity in the theophylline assay and TSH assay using the high quantum yield acridinium compounds of the present invention illustrates, in general, the utility of these compounds in enhancing assay sensitivity of a variety of assays. There are numerous methods of designing immunoassays and nucleic acid assays, which are well known in the art. Regardless of the assay design, if an assay for an analyte relies on the generation of a chemiluminescent signal for measurement of the concentration of that analyte, then the acridinium compounds of the present invention, because of their high quantum yield and hydrophilic nature, will enable a more sensitive measurement of concentration of that analyte.

The chemiluminescent acridinium compounds suitable for use in the present invention have the following structure:

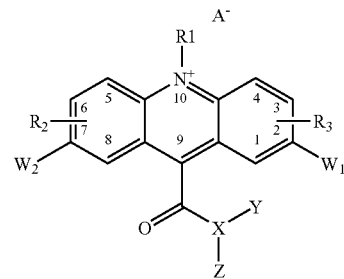

wherein, $R_1$ is selected from an alkyl, alkenyl, alkynyl or aralkyl containing up to 20 heteroatoms; preferably a methyl, a sulfopropyl, or a sulfobutyl group;

$R_2$ and $R_3$ can be the same or different, and are selected from groups comprising hydrogen, halides or R where R is

TABLE 5

TSH Assay Sensitivity using Acridinium Compounds as Labels

|  | NSP-DMAE-HEG-glutarate | NSP-2,7-(OMTEG)$_2$-DMAE | NSP-2,7-(OMTEG)$_2$-DMAE-HEG-glutarate | NSP-2,7-(OMHEG)$_2$-DMAE-AC | NSP-2,7-(OMHEG)$_2$-DMAE-HEG-glutarate |
|---|---|---|---|---|---|
| TSH [mI.U./L] | 0.015 | 0.004 | 0.004 | 0.010 | 0.002 | selected from an alkyl, alkenyl, alkynyl, aryl, or aralkyl containing up to 20 heteroatoms at positions other than C-2 and C-7;

X is oxygen or nitrogen;

when X is oxygen, Z is omitted and Y is a substituted aryl moiety of the formula:

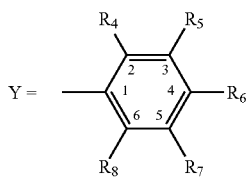

where $R_4$ and $R_8$ can be the same or different and are selected from hydrogen, alkyl, alkenyl, alkynyl, alkoxyl (—OR), alkylthiol (—SR), or —NR$_a$R$_b$ groups where R$_a$ and R$_b$ can be the same or different, and are selected from alkyl, alkenyl, alkynyl, aryl, or aralkyl containing up to 20 heteroatoms, $R_4$ and $R_8$ are preferably methyl;

$R_5$ and $R_7$ are the same or different and are hydrogen or the same as R as defined above;

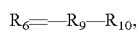

where $R_9$ is not required and is selected from branched or straight-chained alkyl, substituted or unsubstituted aryl or aralkyl containing up to 20 heteroatoms, and $R_{10}$ is a leaving group or an electrophilic functional group attached with a leaving group selected from the group consisting of:

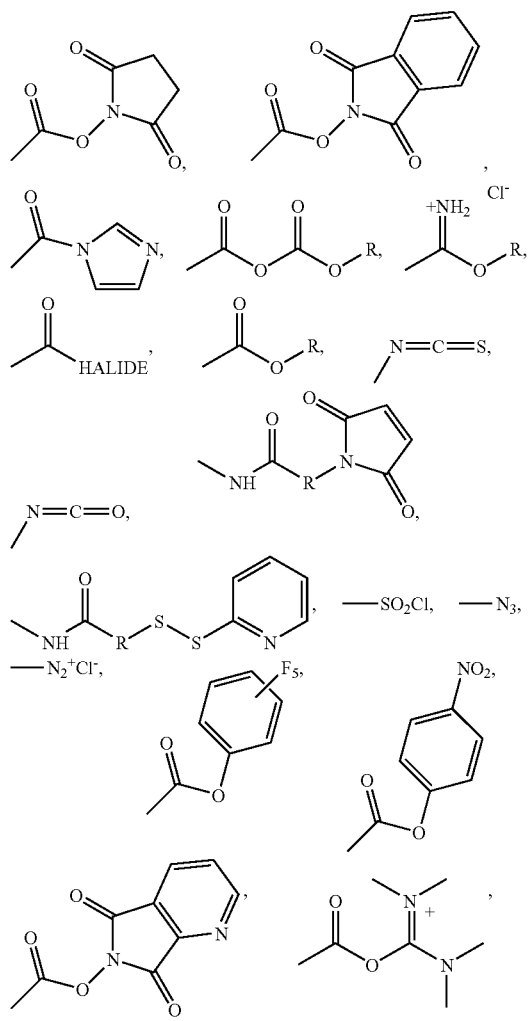

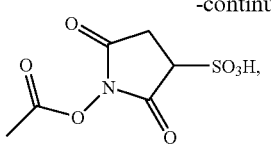

a halide or —COOH;

$R_5$ and $R_6$, and $R_6$ and $R_7$ are interchangeable.

Alternatively, when X is oxygen, Z is omitted and Y is —N=C(R$_{11}$R$_{12}$) where $R_{11}$ and $R_{12}$ are the same as $R_6$ defined above and can be the same or different;

when X is nitrogen, Y is the same as $R_6$ defined above, Z is —SO$_2$—Y', and Y' is a substituted or unsubstituted aryl group or branched or straight chain;

$W_1$ and $W_2$ are the same or different and are electron-donating groups comprising —OR, —OH, —SR, —SR, —NH$_2$, —NR'R''; wherein R, R' and R'' can be the same or different, and are selected from the group consisting of alkyl, alkenyl, alkynyl, aryl, and aralkyl containing up to 20 heteroatoms; preferably $W_1$ and $W_2$ can be the same or different and are selected from —OMe, —OCH$_2$CH$_2$CH$_2$SO$_3^-$ and —O(CH$_2$CH$_2$O)$_n$—CH$_2$—CH$_2$—OMe, wherein Me represents a methyl group and n=0-5.

A$^-$ is a counter ion which is introduced to pair with the quaternary nitrogen of said acridinium nucleus, and is selected from the group consisting of CH$_3$SO$_4^-$, FSO$_3^-$, CF$_3$SO$_4^-$, C$_4$F$_9$SO$_4^-$, CH$_3$C$_6$H$_4$SO$_3^-$, halide, CF$_3$COO$^-$, CH$_3$COO$^-$, and NO$_3^-$.

More specifically, the acridinium compound can be an acridinium ester of the following structure:

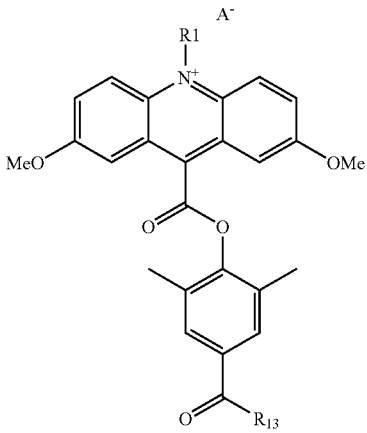

where $R_{13}$ is selected from —OH, —O—N-succinimidyl, —NH—(CH$_2$)$_5$—C(O)—O—N-succinimidyl, —NH—(C$_2$H$_4$O)$_n$—C$_2$H$_4$NH—C(O)—(CH$_2$)$_3$—C(O)—O—N-succinimidyl, wherein n=0 to 5, or —NH—R—NHR, and where $R_1$, A$^-$, and R are as described previously.

The acridinium compound can also be an acridinium ester of the following structure:

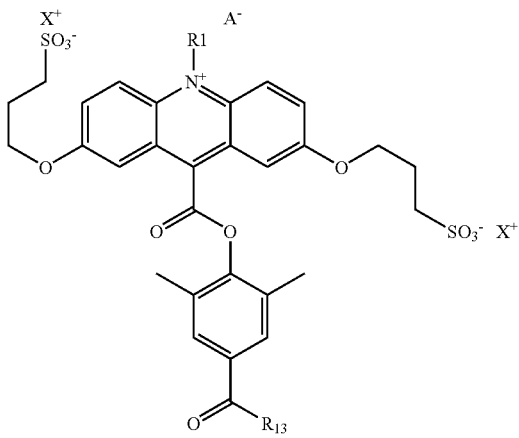

where $R_{13}$, $R_1$ and $A^-$ are defined above, and $X^+$ is a positively charged counterion to pair with the sulfonate moiety and can include $H^+$, $Na^+$, $K^+$, or $NH_4^+$.

The acridinium compound can also be an acridinium ester of the following structure:

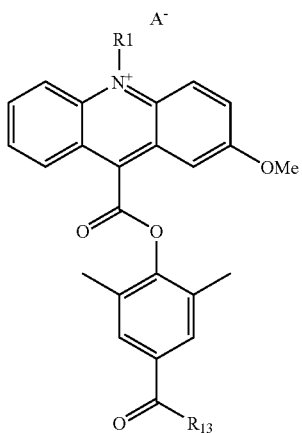

where $R_{13}$, $R_1$ and $A^-$ are defined previously.

The acridinium compound can also be an acridinium ester of the following structure:

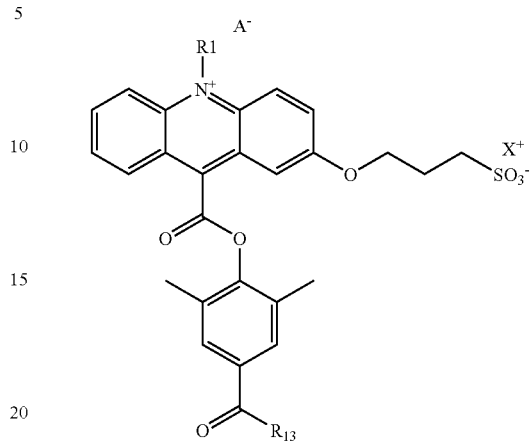

where $R_{13}$, $R_1$, $A^-$ and $X+$ are defined previously.

The acridinium compound can also be an acridinium ester of the following structure:

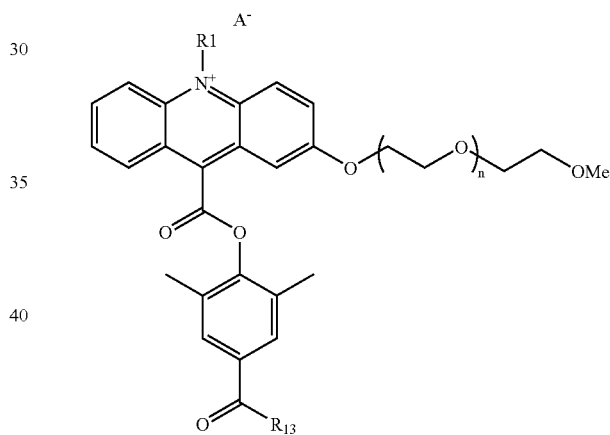

where $R_{13}$, $R_1$ and $A^-$ are defined previously, and n=0 to 5.

The acridinium compound can also be an acridinium ester of the following structure:

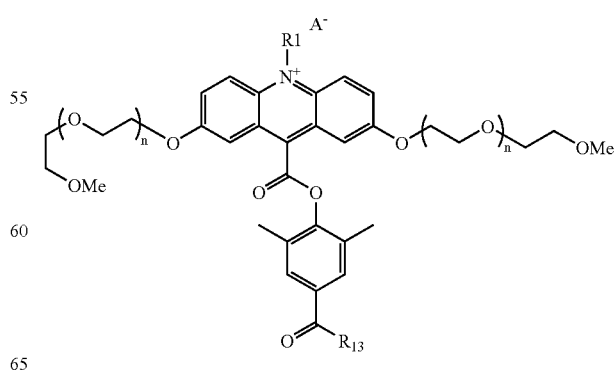

where $R_{13}$, $R_1$ and $A^-$ and n are described previously.

The acridinium compound can also be an acridinium ester of the following structure:
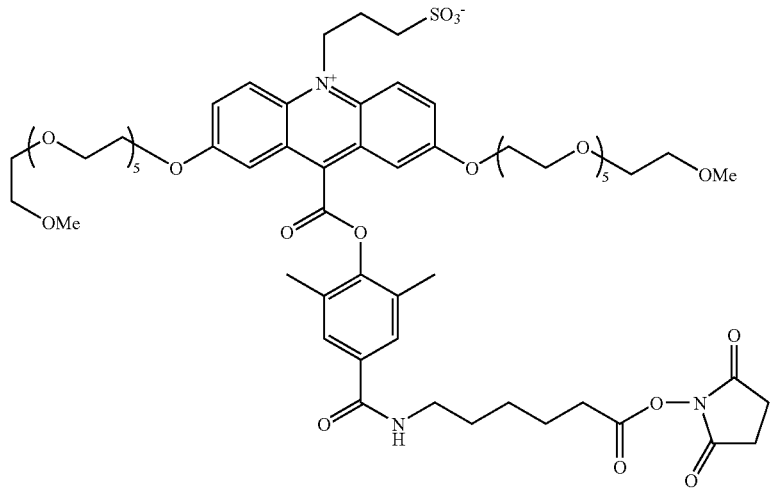
The acridinium compound can also be an acridinium ester of the following structure:
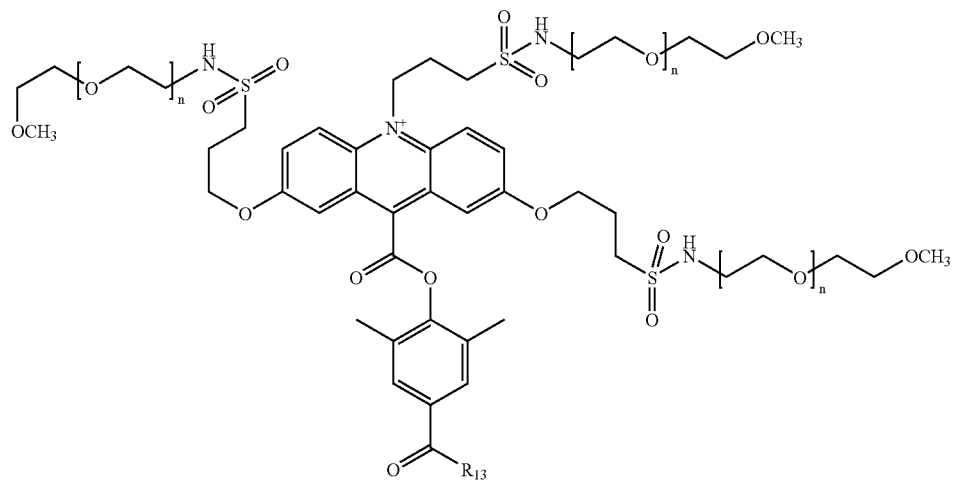
where n and $R_{13}$ are as described previously.

The acridinium compound can also be an acridinium ester of the following structure:

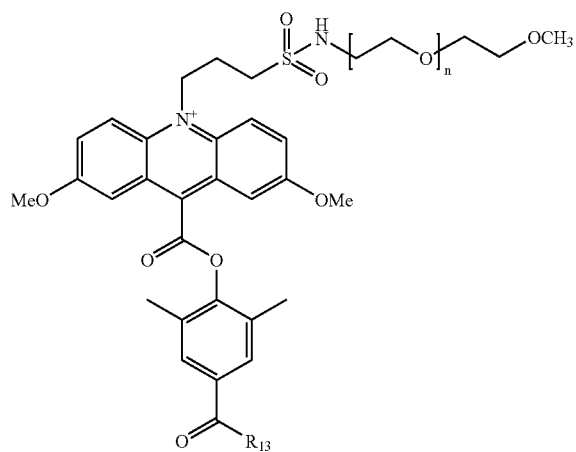

where n and $R_{13}$ are as described previously.

The acridinium compound can also be an acridinium sulfonamide of the following structure:

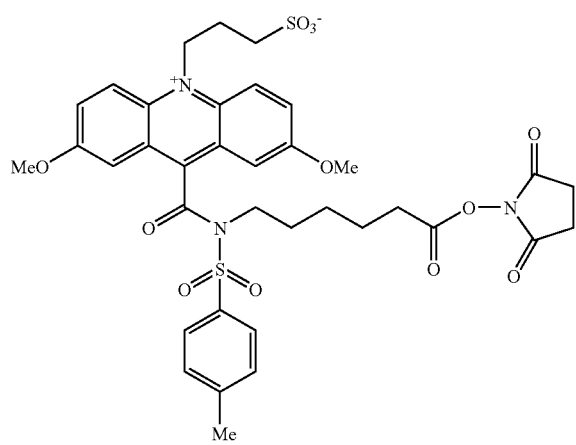

The acridinium compound can also be an acridinium sulfonamide of the following structure, where n=0 to 5.

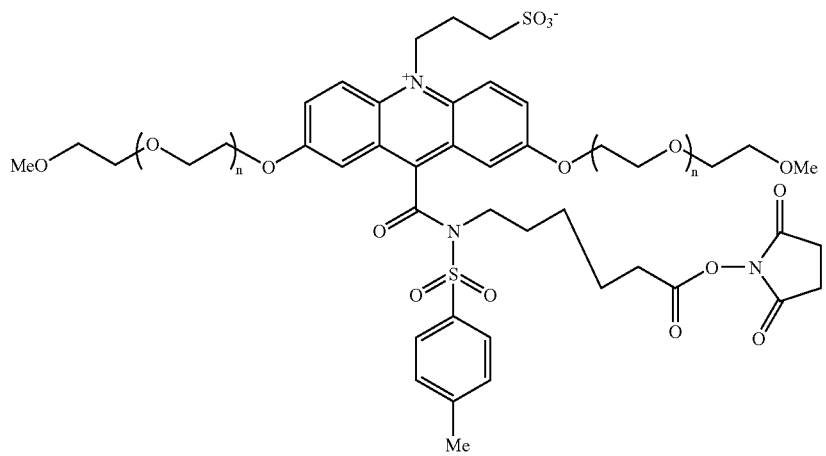

Example 1

Synthesis of 2',6'-dimethyl-4'-carboxyphenyl 2,7-dimethoxy-10-N-sulfopropyl-acridinium-9-carboxylate [NSP-2,7-(OMe)$_2$-DMAE] and its N-succinimidyl ester [NSP-2,7-(OMe)$_2$-DMAE-NHS]

(a) Synthesis of 2',6'-dimethyl-4'-benzyloxycarbonylphenyl 2,7-dimethoxy-acridine-9-carboxylate 2,7-Dimethoxy acridine-9-carboxylic acid (U.S. Pat. No. 5,521,103) (0.5 g, 0.00177 mol) in pyridine (~25 mL) was treated with tosyl chloride (0.674 g, 2 equivalents). After 10 minutes of stirring, 4-benzyloxycarbonyl-2,6-dimethylphenol (0.453 g, 1 equivalent) was added and the resulting mixture was stirred at room temperature under a nitrogen atmosphere. After 1-2 hours, an additional 2 equivalents of toluenesulfonyl chloride was added along with 0.5 equivalent of the phenol and 10-15 mL pyridine. The reaction was stirred at room temperature under nitrogen atmosphere for 48 hours. The solvent was then removed under reduced pressure and the residue was dissolved in 50 mL chloroform. This solution was washed with 2% aqueous ammonium chloride and 2% aqueous sodium bicarbonate. The chloroform extract was then dried over magnesium sulfate, filtered and evaporated to dryness. The crude product was purified by preparative TLC using 5% ethyl acetate in chloroform. Yield=0.663 g (72%). MALDI-TOF MS 524.3 obs. (521.6 calc.).

(b) Synthesis of 2',6'-dimethyl-4'-carboxyphenyl 2,7-dimethoxy-10-N-sulfopropyl-acridinium-9-carboxylate The acridine ester from above (20 mg, 38.4 umoles), 1,3-propane sulfone (0.28 g, 2.29 mmoles) and sodium bicarbonate (32 mg, 384 umoles) were mixed in a 10 mL round bottom flask and heated in an oil-bath at 120° C. under a nitrogen atmosphere. After 4 hours, the reaction was cooled to room temperature and diluted with ethyl acetate (10 mL). The suspension was sonicated until the gummy solid was dispersed into the solvent to give a reddish-yellow precipitate. This precipitate was collected by filtration and rinsed with ethyl acetate. It was then dissolved in methanol and filtered. HPLC analysis of the filtrate using a $C_{18}$ column (Phenomenex 4.6 mm×30 cm) and a 30 minute gradient of 10-70% MeCN in water (each solvent with 0.05% trifluoroacetic acid) showed product eluting at 23 minutes with ~10% starting material eluting at 31 minutes. The methanol solution was evaporated to dryness to give 42 mg of crude product which was stirred in 2 mL of 30% HBr/AcOH at room temperature. Ether (30 mL) was added after 6 hours to precipitate the product, which was collected by filtration and rinsed with ether. The product was dissolved in methanol (40 mL) and analyzed by HPLC as described above. The product was found to elute at 15.9 minutes with no starting material. Evaporation of the methanol filtrate afforded an oily solid, which was re-dissolved in methanol (2-3 mL) and diluted with ethyl acetate (20 mL). Evaporation of the solvent yielded a yellow solid. Yield=34 mg. A portion of this material was dissolved in DMF (2-3 mL) and purified by preparative HPLC using a 30 mm×30 cm $C_{18}$ column. The HPLC fraction, containing product was frozen at −80° C. and, lyophilized to dryness to give a bright yellow powder. MALDI-TOF MS 555.7 obs. (553.6 calc.).

(c) Synthesis of 2',6'-dimethyl-4'-N-succinimidyloxycarbonyphenyl 2,7-dimethoxy-10-N-sulfopropyl-acridinium-9-carboxylate Crude NSP-2,7-(OMe)$_2$-DMAE (34 mg, 61.5 umoles,) in DMF (3 mL) was treated with diisopropylethylamine (13 uL, 1.2 equivalents) and TSTU (18.5 mg, 1 equivalent). After stirring for 15 minutes, HPLC analysis as described in step (b) r, indicated complete conversion to product eluting at 17.8 minutes. A portion of the above reaction mixture was purified by preparative HPLC as described in step (b). The HPLC fraction, containing product was frozen at 80° C. and lyophilized to dryness to give a bright yellow powder. MALDI-TOF MS 653.2 obs. (650.7 calc.).

The following reactions describe the synthesis of NSP-2, 7-(OMe)$_2$-DMAE and its NHS ester.

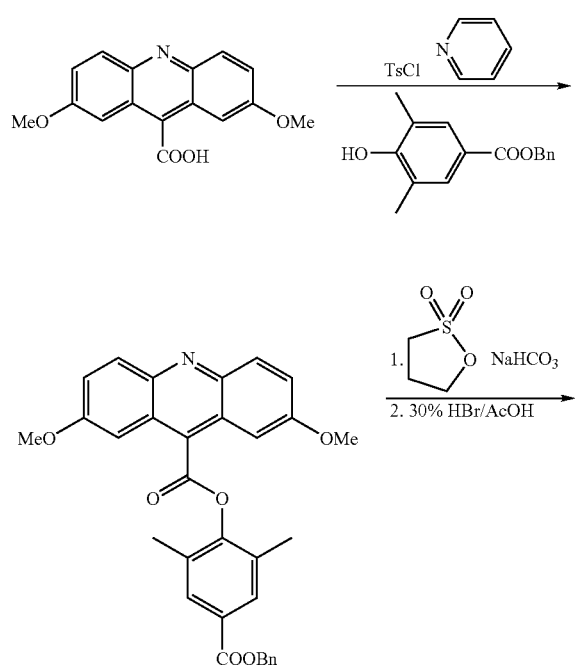

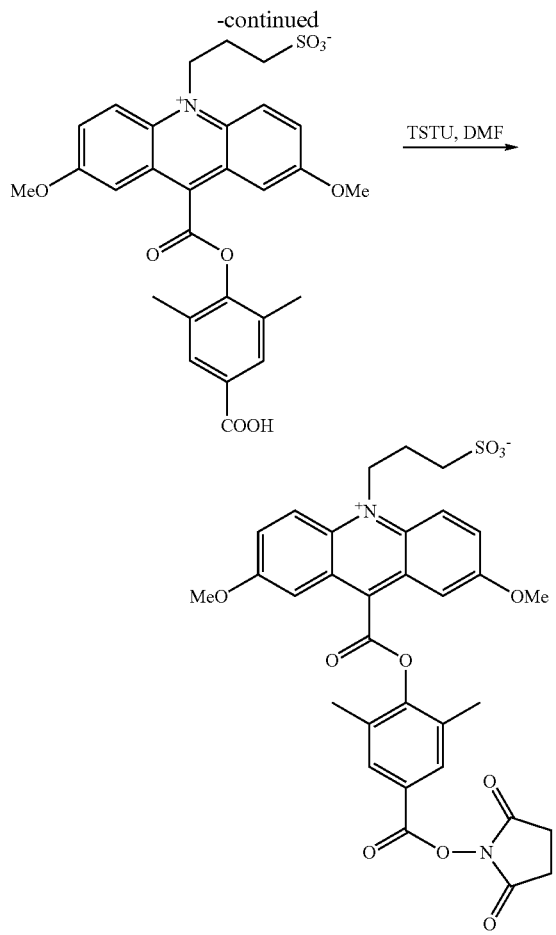

Example 2

Synthesis of 2',6'-dimethyl-4'-carboxyphenyl 2-methoxy-10-N sulfopropyl-acridinium-9-carboxylate (NSP-2-OMe-DMAE)

(a) Synthesis of N-(4-methoxyphenyl)isatin

A solution of isatin (2.5 g, 0.017 mol) in anhydrous DMF (50 mL) was cooled to 0° C. in an ice-bath and treated with sodium hydride (0.5 g, 1.2 equivalents). A purple solution was formed which was stirred at 0° C. for 30 minutes and then warmed to room temperature. To this solution was added 4-bromoanisole (2.13 mL, 1 equivalent) followed by copper iodide (6.46 g, 2 equivalents). The reaction was heated in an oil-bath at 145° C. for 6-7 hours. The reaction was then cooled to room temperature, diluted with an equal volume of ethyl acetate and filtered. The filtrate was evaporated to dryness. The crude product, which was obtained as a dark brown solid was used as such for the next reaction.

(b) Synthesis of 2-methoxy-acridine-9-carboxylic acid

The isatin from step (a) was refluxed with 150 mL of 10% potassium hydroxide under a nitrogen atmosphere. After 4 hours, the reaction was cooled to room temperature and filtered. The filtrate was diluted with water (150 mL) and ice.

This solution was then acidified with concentrated HCl. A yellow precipitate separated out which was collected by filtration and rinsed with cold water and ether. After air drying, the precipitate was transferred to a round-bottom flask with methanol and evaporated to dryness. The resulting residue was evaporated to dryness twice from toluene and was obtained as a yellowish brown powder. Yield=1.15 g (26%).

(c) Synthesis of 2',6'-dimethyl-4'-benzyloxycarbonylphenyl 2-methoxy-acridine-9-carboxylate 2-Methoxy acridine-9-carboxylic acid (0.8 g, 0.0032 mol) in pyridine (30 mL) was cooled in an ice-bath under a nitrogen atmosphere and treated with tosyl chloride (1.32 g, 2 equivalents) followed by 4-benzyloxycarbonyl-2,6-dimethylphenol (0.81 g). The reaction was warmed to room temperature and stirred for 24 hours. The solvent was then removed under reduced pressure and the residue was suspended in 100 mL toluene and evaporated to dryness. The resulting residue was dissolved in chloroform (10 mL) and purified by flash chromatography on silica gel using 5% ethyl acetate, 25% chloroform 70% hexanes. Yield=0.84 g (54%), bright yellow powder. MALDI-TOF MS 492.8 obs. (491.5 calc.).

(d) Synthesis of 2',6'-dimethyl-4'-carboxyphenyl-2-methoxy-10-N-sulfopropyl-acridinium-9-carboxylate This compound was synthesized from the acridine ester by the method described in Example 1, section (b) for NSP-2,7-(OMe)$_2$-DMAE.

(e) Synthesis of 2',6'-dimethyl-4'-N-succinimidyloxycarbonyphenyl 2-methoxy-10-N-sulfopropyl-acridinium-9-carboxylate NSP-2-OMe-DMAE (23 mg, 0.044 mmol) in DMF (1.5 mL) was treated with N-hydroxysuccinimide (25 mg, 5 equivalents) and diisopropyl carbodiimide (68 uL, 10 equivalents). The reaction was stirred vigorously at room temperature. After 36 hours, HPLC analysis, as described earlier in Example 1, section (b), showed complete conversion to product eluting at 16.7 minutes with no starting material at 14.7 minutes. The product was purified by preparative HPLC using a C$_{18}$, 20 mm×30 cm column. The HPLC fraction, containing product was frozen at −80° C. and lyophilized to dryness to give a bright yellow powder. Yield=23 mg (84%).

The following reactions describe the synthesis of NSP-2-OMe-DMAE

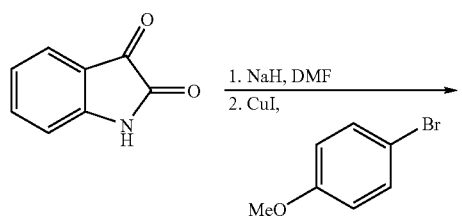

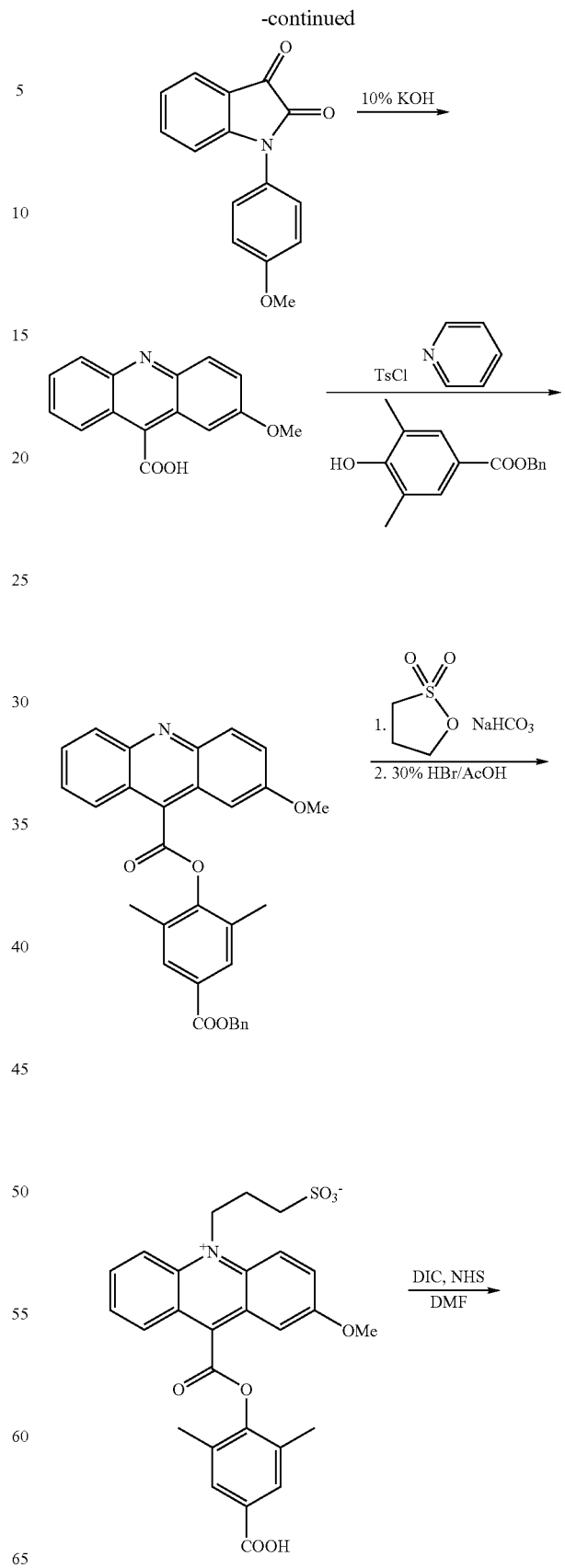

-continued

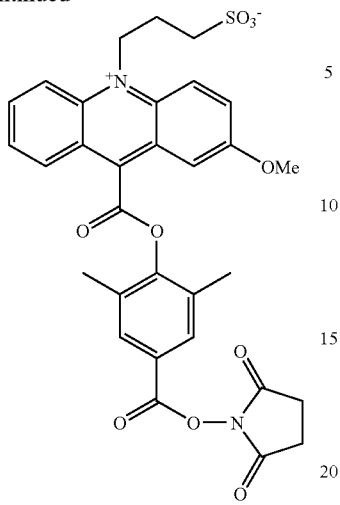

Example 3

Synthesis of 2',6'-dimethyl-4'-carboxyphenyl 3-methoxy-10-N-sulfopropyl-acridinium-9-carboxylate [NSP-3-OMe-DMAE]

This compound was made from 3-bromoanisole, isatin and 4-benzyloxycarbonyl-2,6-dimethylphenol using the same procedures described above for the 2-methoxy analog in Example 2.

The following reactions describe the synthesis of NSP-3-OMe-DMAE.

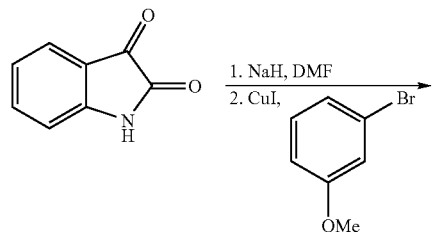

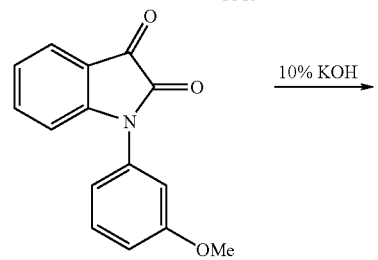

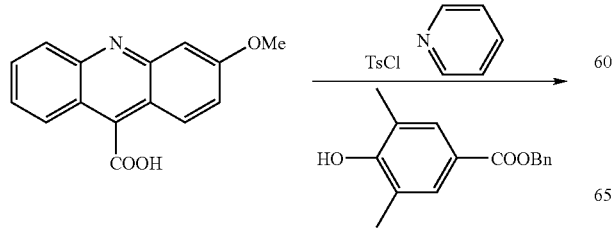

-continued

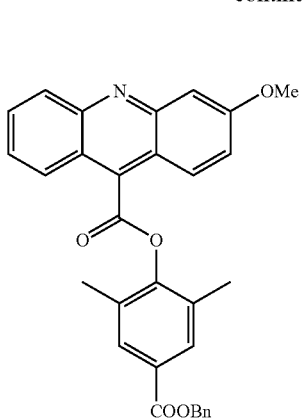

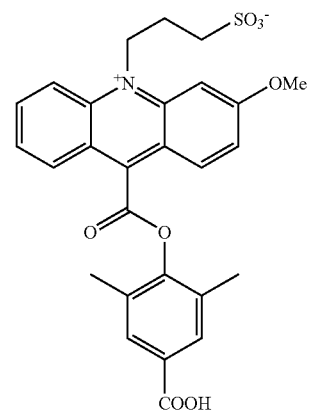

Example 4

Synthesis of 2',6'-dimethyl-4'-carboxyphenyl 4-methoxy-10-N-sulfopropyl-acridinium-9-carboxylate [NSP4-OMe-DMAE]

This compound was made from 2-bromoanisole, isatin and 4-benzyloxycarbonyl-2,6-dimethylphenol using the same procedures described above for the 2-methoxy analog in Example 2. The following reactions describe the synthesis of NSP4-OMe-DMAE.

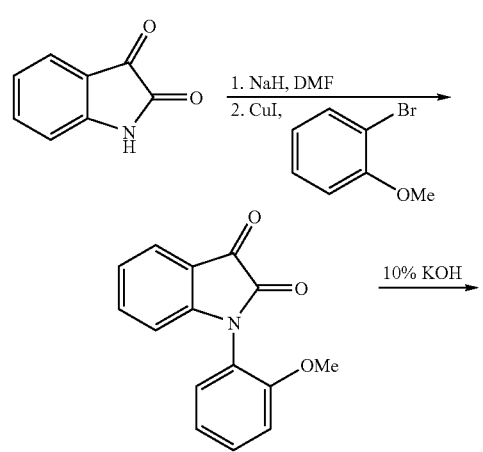

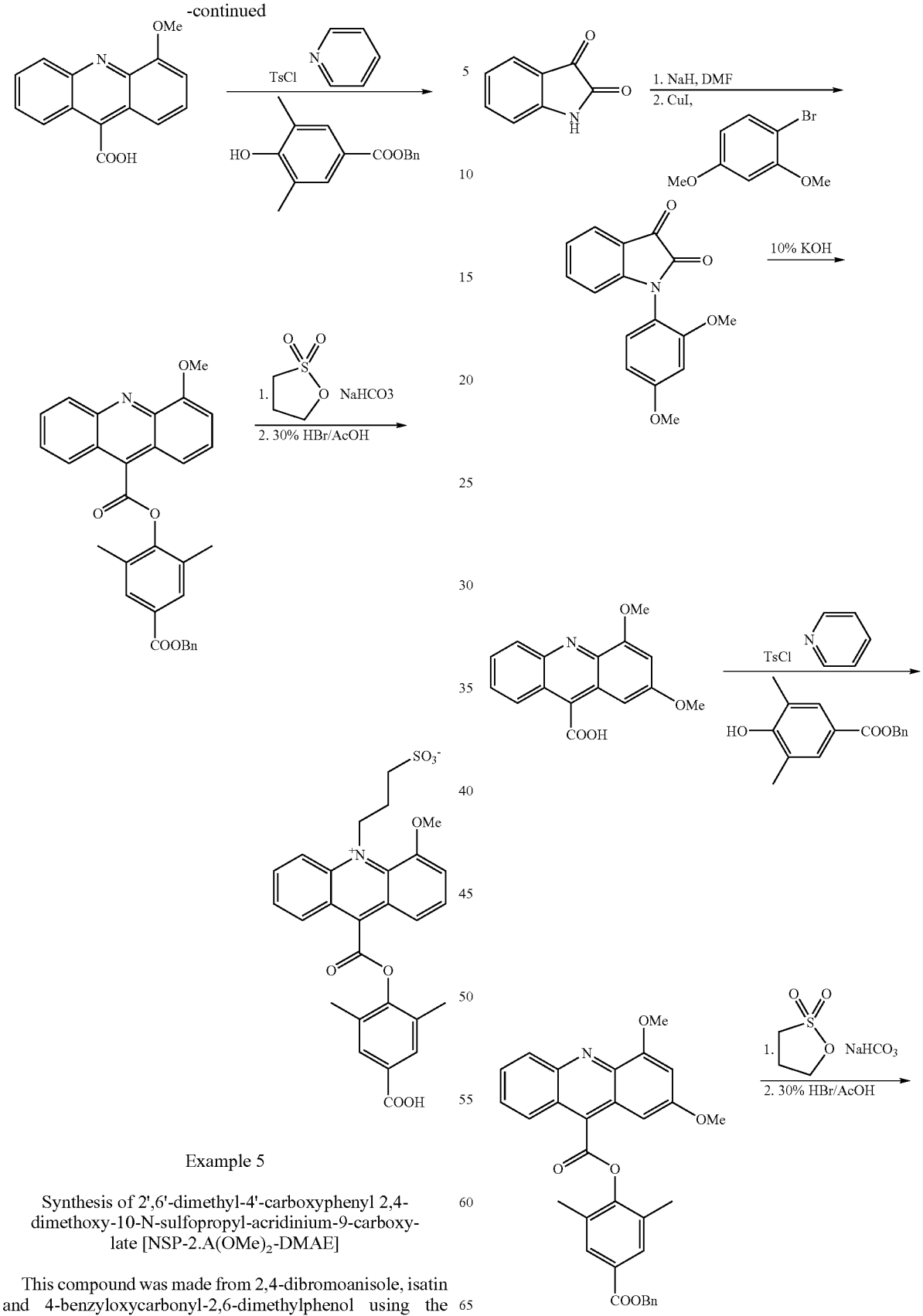
Example 5
Synthesis of 2',6'-dimethyl-4'-carboxyphenyl 2,4-dimethoxy-10-N-sulfopropyl-acridinium-9-carboxylate [NSP-2.A(OMe)$_2$-DMAE]
This compound was made from 2,4-dibromoanisole, isatin and 4-benzyloxycarbonyl-2,6-dimethylphenol using the same procedures described above for the 2-methoxy analog in Example 2. The following reactions describe the synthesis of -continued

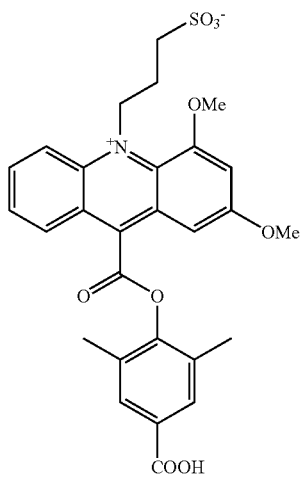

NSP-2,4-(OMe)₂-DMAE.

Example 6

Synthesis of 2',6'-dimethyl-4'-carboxyphenyl 2,5-dimethoxy-10-sulfopropyl-acridinium-9-carboxylate [NSP-2,5-(OMe)₂-DMAE]

(a) Synthesis of N-(2-methoxyphenyl)-5-methoxyisatin

5-Methoxyisatin (2 g, 0.0113 mol) in anhydrous DMF (15 mL) was cooled in an ice-bath under a nitrogen atmosphere and treated with sodium hydride (0.54 g, 1.2 equivalents, 60% dispersion in mineral oil). The reaction was stirred at 0° C. for 0.5 hour and then 2-bromoanisole (1.4 mL, 1 equivalent) was added along with copper iodide (4.3 g, 2 equivalents). The reaction was heated in an oil-bath at 140° C. for 16 hours. The reaction was then cooled to room temperature and filtered. The filtrate was evaporated to dryness. The dark brown oily solid was used directly for the next reaction.

(b) Synthesis of 2,5-dimethoxy acridine-9-carboxylic acid

The crude isatin derivative from step (a) was refluxed in 60 mL of 10% potassium hydroxide in water for 4 hours. The reaction was then cooled to room temperature and filtered. The filtrate was acidified with a mixture of concentrated hydrochloric acid and ice until a dark precipitate separated out. The product was collected by filtration and dried under vacuum. Yield=0.32 g (10%).

(c) Synthesis of 2',6'-dimethyl-4'-benzyloxycarbonylpheny-2,5-dimethoxy-acridine-9-carboxylate This compound was synthesized from 2,5-dimethoxy acridine-9-carboxylic acid and 4-benzyloxycarbonyl-2,6-dimethylphenol using the procedure described for the synthesis of the 2,7-dimethoxy analog in Example 1.

(d) Synthesis of 2',6'-dimethyl-4'-carboxyphenyl 2,5-dimethoxy-10-N-sulfopropyl-acridinium-9-carboxylate [NSP-2,5-(OMe)₂-DMAE]

This compound was synthesized by reaction of the acridine ester with 1,3-propane sultone using the procedure described for the synthesis of the NSP-2,7-(OMe)₂-DMAE in Example 1, section (b).

The following reactions describe the synthesis of NSP-2,5-(OMe)₂-DMAE.

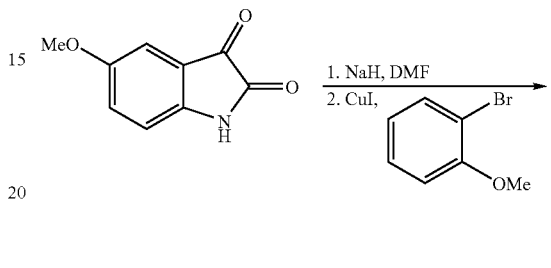

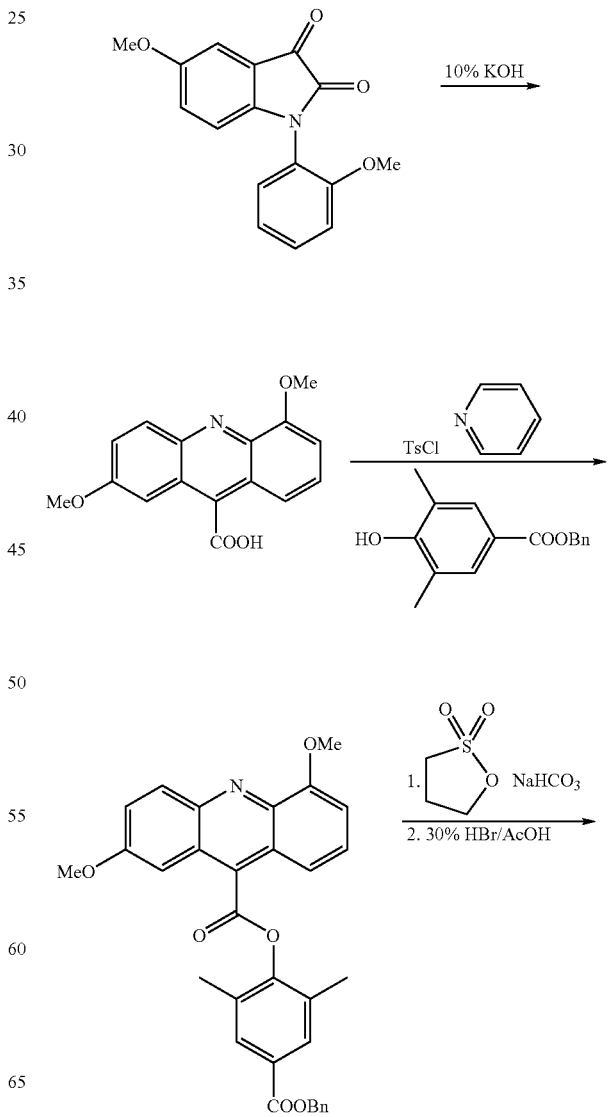

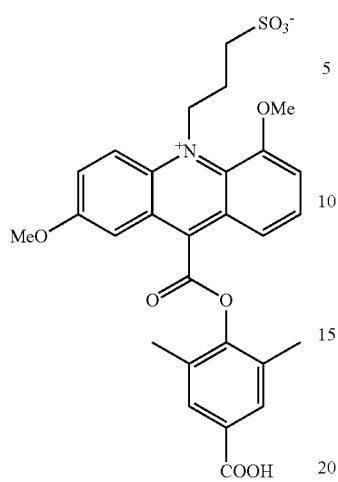

Example 7

Synthesis of 2',6'-dimethyl-4'-carboxyphenyl 2,4,7-trimethoxy-10-N-sulfopropyl-acridinium-9-carboxylate [NSP-2,4,7-(OMe)₃-DMAE]

This compound was synthesized from 5-methoxyisatin, 2,4-dibromoanisole and 2,6-dimethyl-4-carboxybenzylphenol using procedures described in Example 6.

The following reactions describe the synthesis of NSP-2,4,7-(OMe)₃-DMAE.

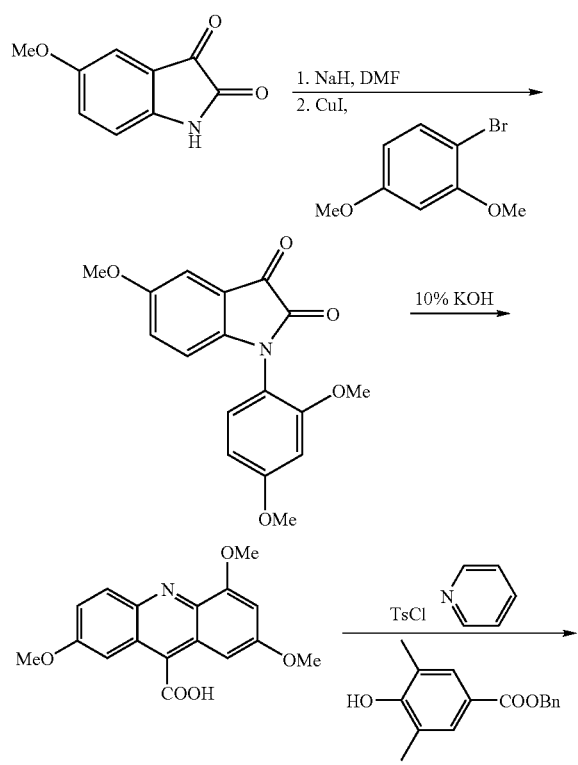

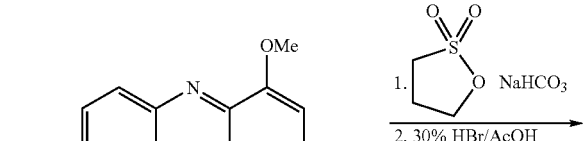

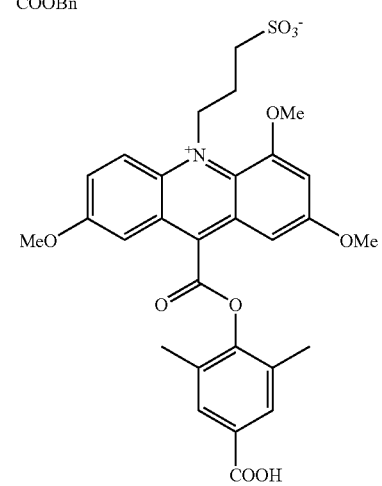

Example 8

Synthesis of 2',6'-dimethyl-4'-carboxyphenyl 2,7-bis(O-sulfopropyl)-10-N-sulfopropyl-acridinium-9-carboxylate [NSP-2.7-(OSP)₂-DMAE] and its N-succinimidyl ester [NSP-2,7-(OSP)₂-DMAE-NHS]

(a) Synthesis of 2',6'-dimethyl-4'-methoxycarbonylphenyl 2,7-dihydroxy-acridine-9-carboxylate A solution of 2',6'-dimethyl-4'-benzyloxycarbonylphenyl-2,7-dimethoxy-acridine-9-carboxylate (52 mg, 100 umoles) in dichloromethane (5 mL) was cooled in an ice-bath under a nitrogen atmosphere and treated with a 1M solution of boron tribromide in dichloromethane (4 mL). The reaction was warmed to room temperature and stirred for 34 hours. The reaction was then cooled again in an ice-bath and methanol (10 mL) was added carefully. The reaction was then warmed to room temperature and stirred for 16 hours. After the indicated reaction time, solid sodium bicarbonate was added to the reaction till neutral by pH paper. The whole reaction mixture was then evaporated to dryness. The residue was partitioned between ethyl acetate (30 mL) and water (50 mL). The ethyl acetate layer was dried over anhydrous magnesium sulfate, filtered and evaporated to dryness to give a yellow powder. Yield=30 mg (75%). MALDI-TOF MS 419.4 obs. (420.5 calc.).

(b) Synthesis of 2',6'-dimethyl-4'-carboxyphenyl 2,7-bis(O-sulfopropyl)-10-N-sulfopropyl acridinium-9-carboxylate The 2,7-dihydroxy acridine derivative from section (a) (30 mg, 71.6 umoles) was mixed with 1,3-propane sultone (0.875 g, 100 equivalents) and sodium bicarbonate (120 mg, 20 equivalents). The mixture was heated in an oil-bath at 140° C. with vigorous stirring. After one hour, additional 100 equivalents of 1,3-propane sultone and 20 equivalents of sodium bicarbonate were added and the reaction was continued. After an additional hour, the reaction mixture was treated with more 1,3-propane sultone (100 equivalents) and sodium bicarbonate (20 equivalents). The reaction was continued for an hour and then cooled to room temperature. Ethyl acetate (20 mL) was added and the reaction mixture was sonicated briefly (15 minutes) to disperse the gum into a yellow precipitate. This precipitate was collected by filtration and rinsed with ethyl acetate. This solid and then transferred with the help of methanol to a round-bottom flask and was then evaporated to dryness. The resulting residue was suspended in 20 mL of IN hydrochloric acid and was refluxed for 3 hours. HPLC analysis as described in Example 1, section (b), indicated product eluting at 11 minutes along with some by-products. The reaction mixture was concentrated to a small volume and was purified by preparative HPLC using a $C_{18}$, 20 mm×30 cm column. The HPLC fraction containing the product was frozen at −80° C. and lyophilized to dryness to yield a bright yellow powder. Yield=12.5 mg (23%). 772.7 obs. (769.8 calc.).

(c) Synthesis of 2',6'-dimethyl-4'-N-succinimidyloxycarbonylphenyl 2,7-bis(O-sulfopropyl)-10-N-sulfopropyl acridinium-9-carboxylate NSP-2,7-(OSP)$_2$-DMAE (3 mg, 3.9 umoles) was dissolved in anhydrous DMN (1 mL) and treated with diisopropylethylamine (1.4 uL) and TSTU (1.8 mg, 1.2 equivalents). The reaction was stirred at room temperature. After 40 minutes, additional diisopropylethylamine and TSTU was added and the reaction was continued for 30 minutes. HPLC analysis using a $C_{18}$ column from Phenomenex, 4.6 mm×30 cm, and a 40 minute gradient of 10%→40% MeCN in water, each with 0.05% trifluoroacetic acid, at a flow rate of 1 mL/min showed complete conversion to product eluting at 19 minutes with so starting material at 17 minutes. The product was purified by preparative HPLC using a $C_{18}$, 20 mm×30 cm column. The product fraction, containing product was frozen at −80° C. and lyophilized to dryness. Yield=2 mg (59%). MALDI-TOF MS 868.2 obs. (866.9 calc.).

The following reactions describe the synthesis of NSP-2, 7-(OSP)$_2$-DMAE and its NHS ester.

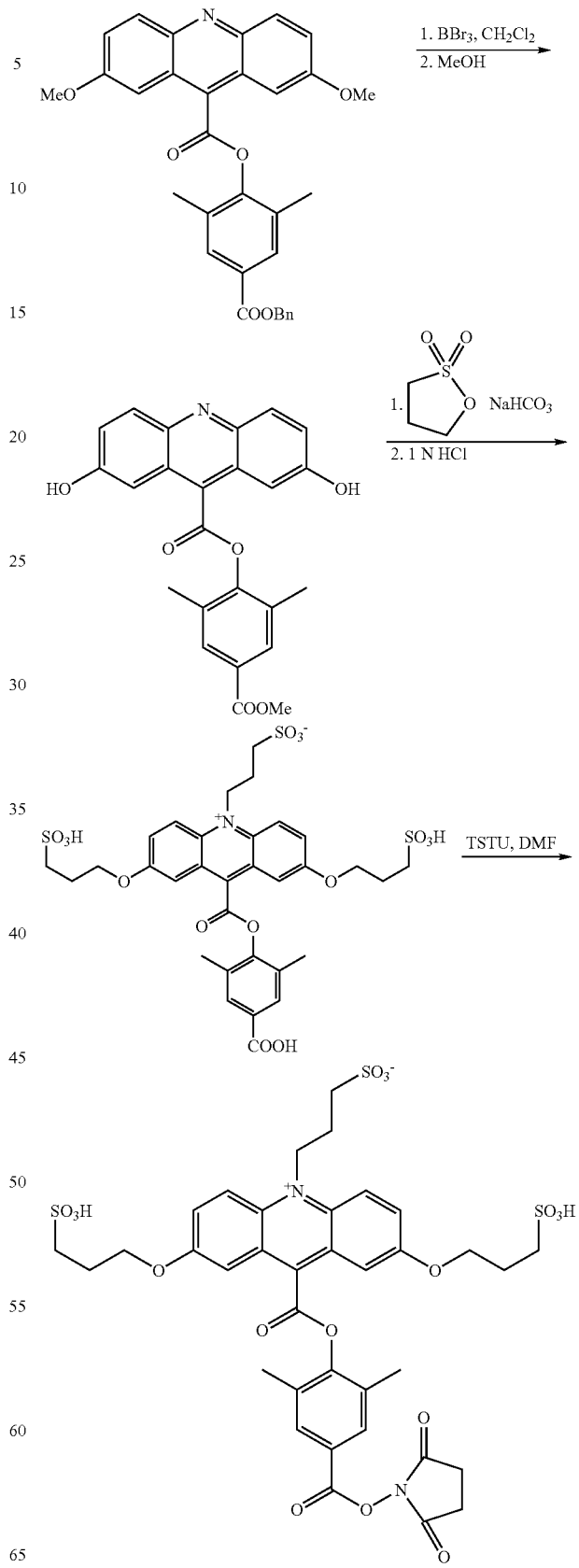

Example 9

Synthesis of 2',6'-dimethyl-4'-carboxyphenyl 2,7-bis [O-methoxyhexa(ethylene)glycol]-10-N-sulfopropyl-acridinium-9-carboxylate [NSP-2,7-(OMHEG)$_2$-DMAE]: 2',6'-dimethyl-4'-carboxyphenyl 2,7-bis[O-methoxyhexa(ethylene)glycol]-10-N-methyl-acridinium-9-carboxylate [2,7-(OMHEG)$_2$-DMAE]: their N-succinimidyl esters [2,7-(OMHEG)$_2$-DMAE-NHS] and [NSP-2,7-(OMHEG)$_2$-DMAE-NHS]: 2'6'-dimethyl-4'-N-succinimidyloxy-glutarylamidohexa(ethylene)glycolamidocarbonylphenyl-2,7-bis[O-methoxy-hexa(ethylene)glycol]-10-sulfopropyl-acridinium-9-carboxylate [NSP-2,7-(OMHEG)$_2$-DMAE-HEG-glutarate-NHS] and 2',6'-dimethyl-4'-N-succinimidyl-oxycaproylamidocarbonylphenyl-2, 7-bis[O-methoxy(hexa)ethyleneglycol]-10-N-sulfopropyl-acridinium-9-carboxylate [NSP-2,7-(OMHEG)$_2$-DMAE-AC-NHS]

(a) Synthesis of 2',6'-dimethyl-4'-methoxycarbonylphenyl-2,7-bis[O-methoxyhexa(ethylene) glycol]-acridine-9-carboxylate A solution of 2',6'-dimethyl-4'-methoxycarbonylphenyl-2, 7-dihydroxy acridine-9-carboxylate (100 mg, 0.24 mmol) in anhydrous THF (25 mL) was cooled in an ice bath under a nitrogen atmosphere and treated with sodium hydride (60% dispersion, 25 mg, 2.5 equivalents). After stirring for 30 minutes in the ice bath, methoxy hexa(ethylene) glycol tosylate (Yamashita et al. *J. Am Chem. Soc.* 1995, 117, 6249-6253, 195 mg, 3 equivalents) was added. The resulting reaction was refluxed under nitrogen for 4 hours. The reaction was then cooled to room temperature and quenched with ethyl acetate and methanol and was then evaporated to dryness. The residue was partitioned between chloroform (30 mL) and saturated sodium chloride solution (30 mL). The chloroform layer was separated and the aqueous layer was extracted two more times with chloroform (2×10 mL). The combined organic layer was dried over magnesium sulfate, filtered and evaporated to dryness to give an oil solid. Yield=0.242 g (quant.). HPLC analysis using a $C_{18}$ column from Phenomenex, 4.6 mm×30 cm, and a 30 minute gradient of 10%→70% MeCN in water, each with 0.05% trifluoroacetic acid, at a flow rate of 1 mL/min showed complete conversion to product eluting at 24 minutes. This material was used as such for subsequent transformations.

(b) Synthesis of 2',6'-dimethyl-4'-carboxyphenyl-2,7-bis[O-methoxyhexa(ethylene)glycol]-10-N-methyl-acridinium-9-carboxylate The acridine ester from step (a) (45 mg, 46 umoles) was dissolved in anhydrous dichloromethane (5 mL) and was treated with sodium bicarbonate (20 mg, 5 equivalents) and methyl trifluoromethanesulfonate (50 uL, 10 equivalents). The reaction was stirred at room temperature for 16 hours. HPLC analysis as described in section (a) indicated product eluting at 21 minutes. The reaction was filtered through glass wool to remove sodium bicarbonate and the filtrate was evaporated to dryness. The residue was suspended in 10 mL of 1N HCl and the resulting reaction was refluxed under a nitrogen atmosphere for 2 hours. HPLC analysis showed clean hydrolysis of the methyl ester with the product eluting at 19 minutes. The reaction mixture was then concentrated to a small volume (3-4 mL) by rotary evaporation and the product was purified by preparative HPLC using a YMC, $C_{18}$, 30×300 mm column and the gradient described earlier. The HPLC fraction, containing product was frozen at −80° C. and lyophilized to dryness. Yield=18.2 mg (oil), 40%.

(c) Synthesis of 2',6'-dimethyl-4'-carboxyphenyl-2,7-bis[O-methoxyhexa(ethylene)glycol]-10-N-sulfopropyl-acridinium-9-carboxylate The acridine ester from step (a) (0.1 g, 0.102 mmol) was mixed with 1,3-propane sultone (1.25 g, ~100 equivalents) and sodium bicarbonate (170 mg, 20 equivalents). The mixture was heated in an oil-bath at 130° C. under a nitrogen atmosphere. After 2-3 hours, the reaction was cooled to room temperature and diluted with ethyl acetate (~10 mL). The mixture was sonicated briefly to disperse the gum into a powder, which was collected by filtration. The product was suspended in 10 mL of 1 N HCl and refluxed under a nitrogen atmosphere for 2 hours. It was then cooled to room temperature and analyzed by HPLC as described in section (a) which indicated product eluting at 17 minutes. The product was purified by preparative HPLC as described above and the HPLC fraction was frozen at −80° C. and lyophilized to dryness. Yield ~10 mg (10%).

(d) Synthesis of 2',6'-dimethyl-4'-N-succinimidyloxycarbonyl-phenyl-2,7-bis[O-methoxyhexa(ethylene)glycol]-10-N-methyl-acridinium-9-carboxylate The carboxylic acid 2',6'-dimethyl-4'-carboxyphenyl-2,7-bis[O-methoxyhexa(ethylene)glycol]-10-N-methyl-acridinium-9-carboxylate (18 mg, 18.7 umoles) in anhydrous DMF (2 mL) was treated with diisopropylethylamine (5 uL, 1.5 equivalents) and TSTU (7 mg, 1.2 equivalents). The reaction was stirred at room temperature. After 1 hour HPLC analysis using a $C_{18}$ column from Phenomenex, 4.6 mm×30 cm, and a 30 minute gradient of 10%→70% MeCN in water, each with 0.05% trifluoroacetic acid, at a flow rate of 1 mL/min showed complete conversion to product eluting at Rt=20 minutes. The product was purified using a YMC, $C_{18}$ 20×300 mm column. The HPLC fraction, containing product was frozen at −80° C. and lyophilized to dryness. Yield=14.4 mg (72%). MALDI-TOF MS 1073.1 obs. (1071.2 calc.).

(e) Synthesis of 2',6'-dimethyl-4'-N-succinimidyloxycarbonylphenyl-2,7-bis[O-methoxyhexa(ethylene)glycol]-10-N-sulfopropyl-acridinium-9-carboxylate A solution of 2',6'-dimethyl-4'-carboxyphenyl-2,7-bis[O-methoxyhexa(ethylene)glycol]-10-N-sulfopropyl-acridinium-9-carboxylate (9.3 mg, 8.6 umoles) in anhydrous DMF (2 mL) was treated with diisopropylethylamine (2.3 uL, 1.5 equivalents) and TSTU (3 mg, 1.2 equivalents). The reaction was stirred at room temperature. After 1 hour, HPLC analysis as described in section (d) showed conversion to product eluting at 18.3 minutes. The product was purified by preparative HPLC as described above and the HPLC fraction was frozen at −80° C. and lyophilized to dryness. Yield=6.7 mg (66%). MALDI-TOF MS 1181.1 obs. (1179.3 calc.).

(f) Synthesis of 2',6'-dimethyl-4'-aminohexa(ethylene)glycolamidocarbonylphenyl-2,7-bis[O-methoxyhexa(ethylene)glycol]-10-N-sulfopropyl-acridinium-9-carboxylate A solution of 2',6'-dimethyl-4'-carboxyphenyl-2,7-bis[O-methoxyhexa(ethylene)glycol]-10-N-sulfopropyl-acridinium-9-carboxylate (20 mg, 18.6 umoles) in DMF (2 mL) was treated with diisopropylethylamine (8 uL, 5 equivalents) and TSTU (14 mg, 5 equivalents). The reaction was stirred at room temperature. After 30 minutes, HPLC analysis performed as described in section (d) indicated complete conversion to the NHS ester eluting at 18.5 minutes. This DMF solution was added in 0.1 mL portions to a solution of diamino hexa(ethylene) glycol (U.S. Pat. No. 6,664,043, 56 mg, 5 equivalents) in DMF (1 mL). The reaction was stirred at room temperature. After 30 minutes, HPLC analysis performed as described in section (d) indicated complete conversion to product eluting at 16.2 minutes. The product was purified by preparative HPLC using a YMC, $C_{18}$, 20×300 mm column. The HPLC fraction containing product was evaporated to dryness. Yield 16 mg (62%).

(g) 2',6'-dimethyl-4'-N-succinimidyloxyglutarylamidohexa(ethylene)glycol-amidocarbonylphenyl-2,7-bis[O-methoxyhexa(ethylene)glycol]-10-sulfopropyl-acridinium-9-carboxylate [NSP-2,7-(OMHEG)$_2$-DMAE-HEG-glutarate-NHS]

The product from section (f) (16 mg, 11 umoles) was dissolved in methanol (1 mL) and treated with diisopropylethylamine (9.6 uL, 5 equivalents) and glutaric anhydride (6 mg, 5 equivalents). The reaction was stirred at room temperature. After 30 minutes, HPLC analysis performed as described in section (d) indicated complete conversion to product eluting at 17 minutes. The solvent was then removed under reduced pressure and the residue was suspended in toluene (2 mL) and evaporated to dryness. The crude product was dissolved in DMF (1 m) and treated with diisopropylethylamine (19.2 uL, 10 equivalents) and TSTU (33 mg, 10 equivalents). The reaction was stirred at room temperature. After 30 minutes, HPLC analysis indicated >80% conversion to product eluting at 18 minutes. The product was purified by preparative HPLC as described above. The HPLC fraction containing product was frozen at −80° C. and lyophilized to dryness. Yield=10.7 mg (63%); MALDI-TOF MS 1557.8 obs. (1556.8 calc.).

(h) Synthesis of 2',6'-dimethyl-4'-carboxycaproylamidocarbonylphenyl-2,7-bis[O-methoxy(hexa)ethyleneglycol]-10-N-sulfopropyl-acridinium-9-carboxylate [NSP-2,7-(OMHEG)$_2$-DMAE-AC]

NSP-2,7-(OMHEG)$_2$-DMAE (16 mg, 14.8 umoles) in DMF (1.5 mL) was treated with diisopropylethylamine (5.2 uL, 2 equivalents) and TSTU (9 mg, 2 equivalents). The reaction was stirred at room temperature for 30 minutes and then cooled to 0° C. This solution was then added drop wise to a solution of 6-aminocaproic acid (20 mg, 55.5 10 equivalents) dissolved in 0.1 M NaHCO$_3$ (2 mL). The resulting reaction was stirred at 0° C. in an ice-bath and after 15 minutes it was warmed to room temperature. After 1 hour, the reaction was analyzed by HPLC using a $C_{18}$ column from Phenomenex, 4.6 mm×30 cm, and a 30 minute gradient of 10%→70% MeCN in water, each with 0.05% trifluoroacetic acid, at a flow rate of 1 mL/min, showed complete conversion to product eluting at 17.2 minutes. The product was purified by preparative HPLC using a $C_{18}$, 20 mm×30 cm column. The HPLC fraction, containing product was frozen at −80° C. and lyophilized to dryness. Yield=15.2 mg (84%).

(i) Synthesis of 2',6'-dimethyl-4'-N-succinimidyloxycaproylamidocarbonylphenyl-2,7-bis[O-methoxy(hexa)ethyleneglycol]-10-N-sulfopropyl-acridinium-9-carboxylate [NSP-2,7-(OMHEG)$_2$-DMAE-AC-NHS]

NSP-2,7-(OMHEG)$_2$-DMAE-AC (15 mg, 12,7 umoles) from step (h) was dissolved in DMF (1.5 mL) and treated with diisopropylethylamine (3.3 uL, 1.5 equivalents) and TSTU (4.6 mg, 1.2 equivalents). The reaction was stirred at room temperature for 30 minutes and then analyzed by HPLC using a $C_{18}$ column from Phenomenex, 4.6 mm×30 cm, and a 40 minute gradient of 10%→60% MeCN in water, each with 0.05% trifluoroacetic acid, at a flow rate of 1 mL/min, which, showed complete conversion to product eluting at 24.5 minutes. The product was purified by preparative HPLC using a $C_{18}$, 20 mm×30 cm column. The HPLC fraction, containing product was frozen at −80° C. and lyophilized to dryness. Yield=8 mg (50%). MALDI-TOF MS 1294.5 obs. (1293.5 calc.).

The following reactions describe the synthesis of 2,7-(OMHEG)$_2$-DMAE and NSP-2,7-(OMHEG)$_2$-DMAE, their NHS esters

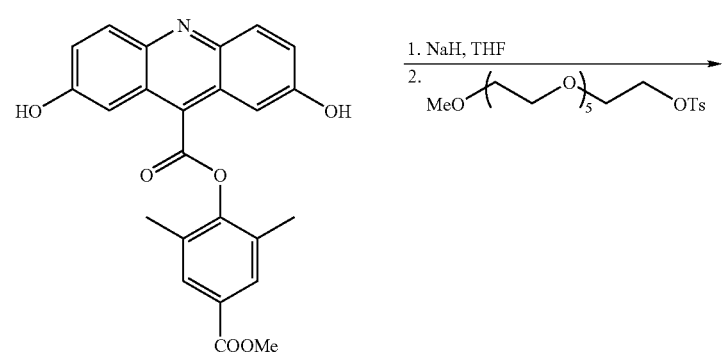

-continued
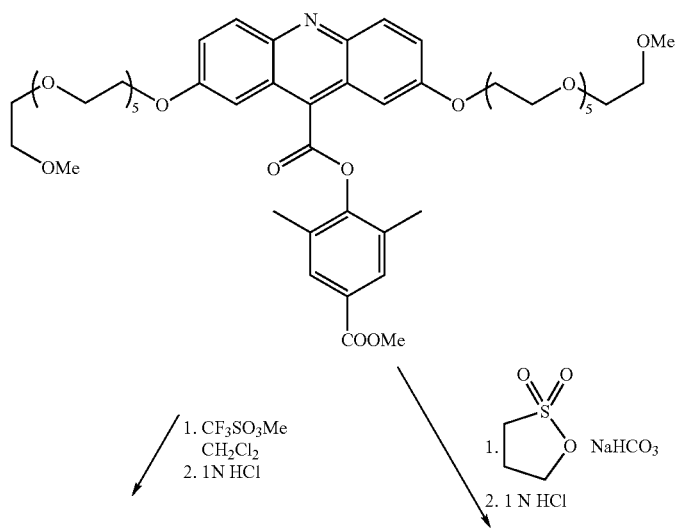
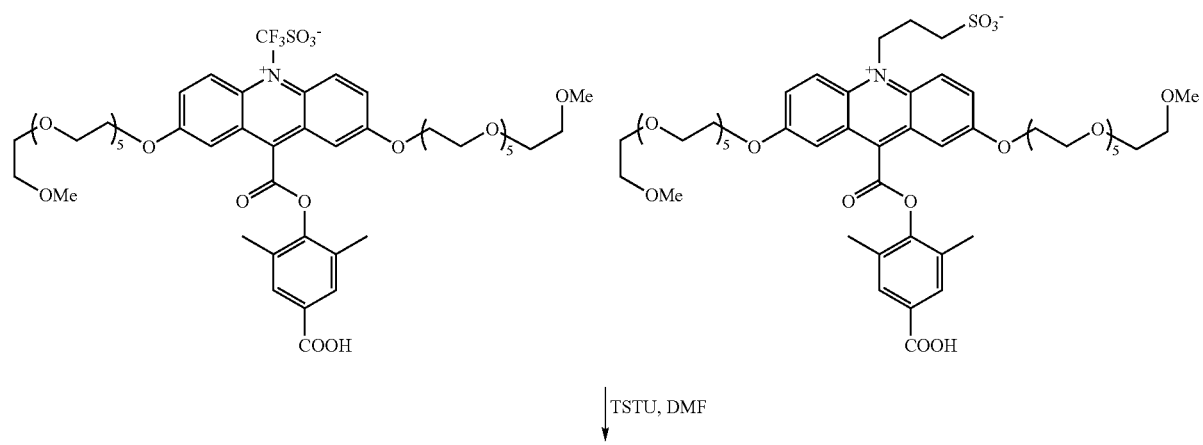
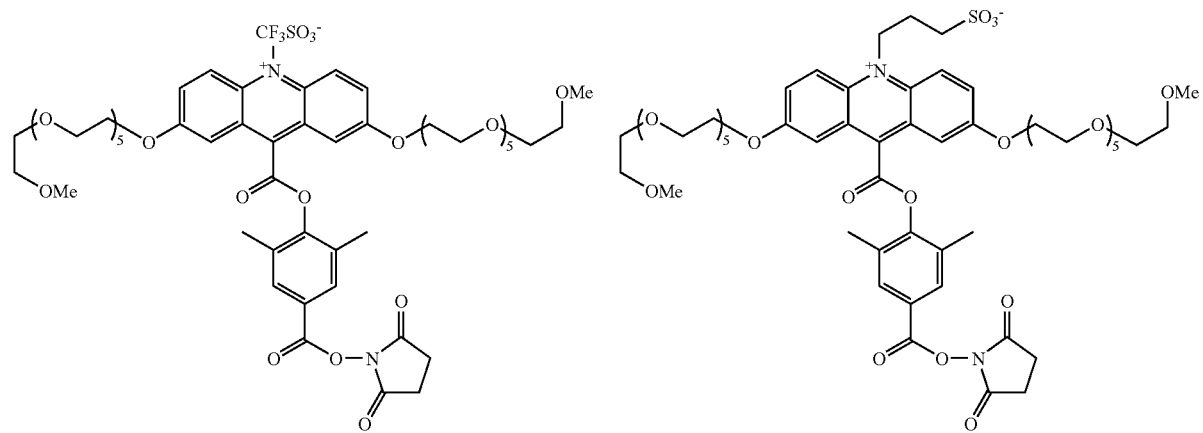

The following reactions describe the synthesis of NSP-2, 7-(OMG)$_2$-DMAE-AC-NHS and NSP-2,7-(OMHEG)$_2$-DMAE-HEG-glutarate-NHS ester.
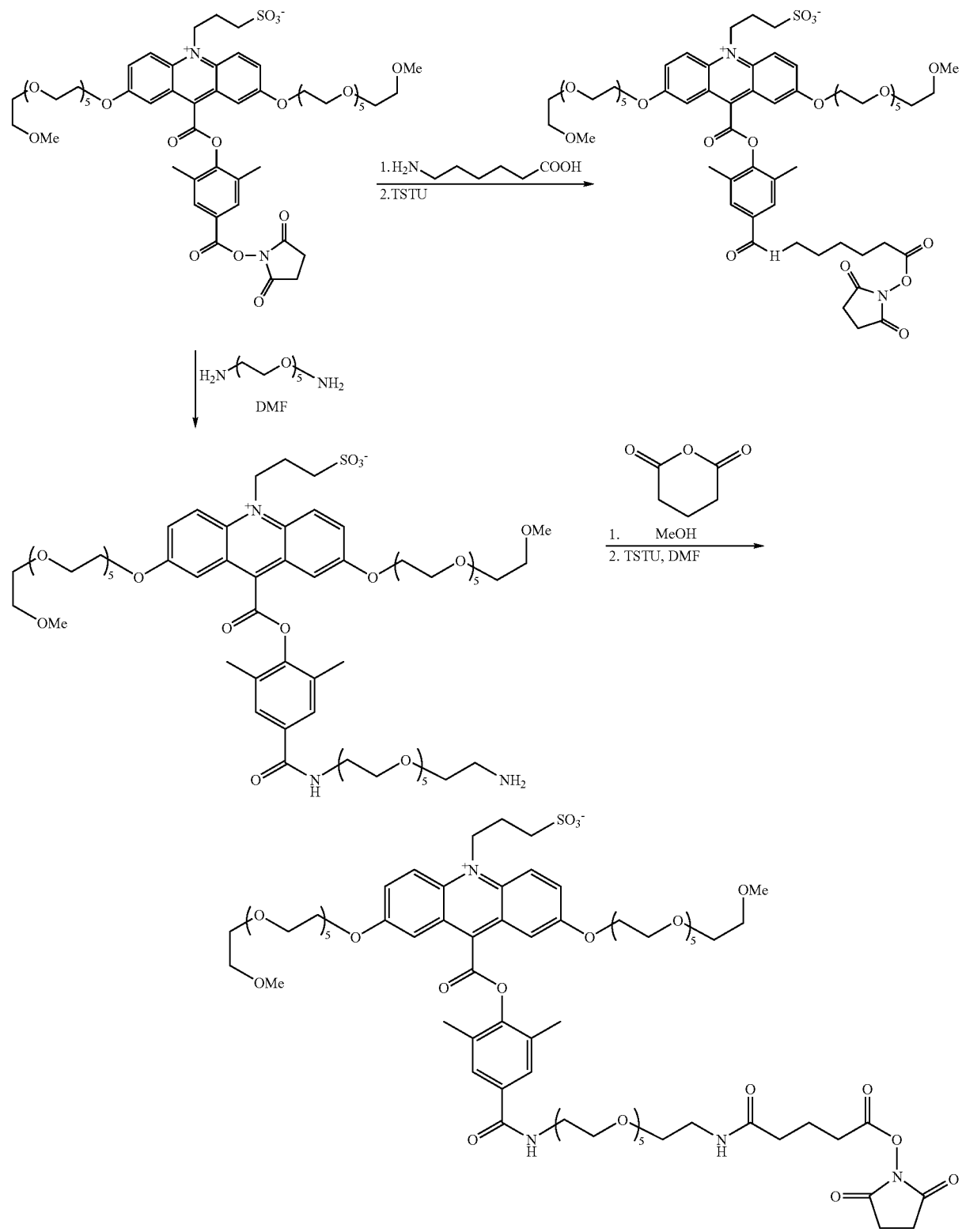

Example 10

Synthesis of 2',6'-dimethyl-4'-carboxyphenyl 2,7-bis[O-methoxytri(ethylene)glycol]-10-N-sulfopropyl-acridinium-9-carboxylate [NSP-2,7-(OMTEG)$_2$-DMAE], its NHS Ester and 2',6'-dimethyl-4'-N-succinimidyl-oxyglutarylamidohexa(ethylene)-glycolamido-carbonylphenyl-2,7-bis[O-methoxytri(ethylene)glycol]-10-sulfopropyl-acridinium-9-carboxylate [NSP-2,7-(OMTEG)$_2$-DMAE-HEG-glutarate-NHS]

These compounds were synthesized using the procedures described in Example 9 for the synthesis of NSP-2,7-(OMTEG)$_2$-DMAE-NHS ester using methoxytri(ethylene)glycol instead of methoxyhexa(ethylene)glycol.

The following reactions describe the synthesis of NSP-2,7-(OMTEG)$_2$-DMAE-NHS ester and NSP-2,7-(OMTEG)$_2$-DMAE-HEG-glutarate-NHS ester.

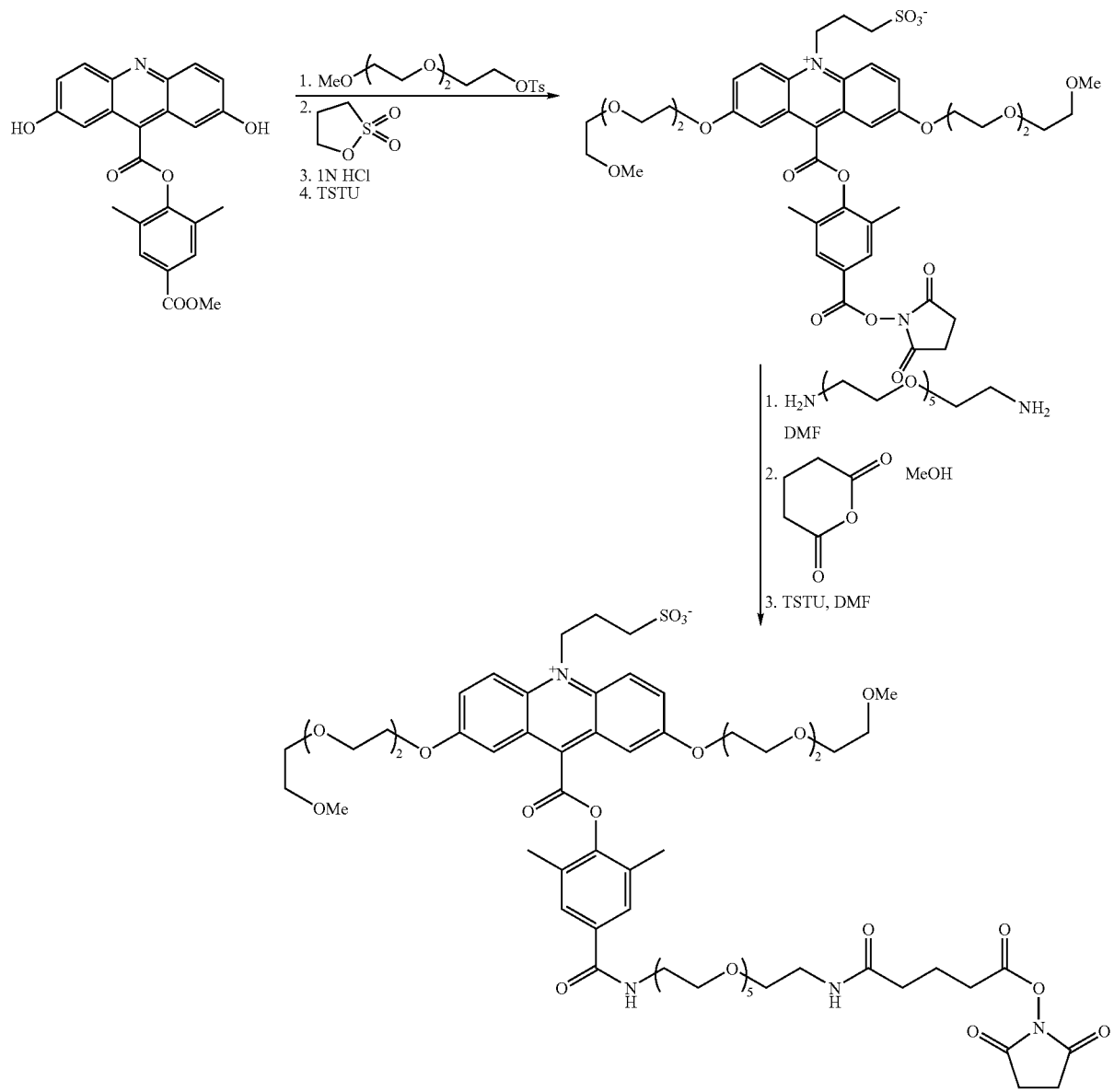

Example 11

Synthesis of 2',6'-dimethyl-4'-N-succinimidyloxycapropyl-amidocarbonylphenyl-$N^{10}$-2,7-tris[O-methoxyhexa(ethylene)glycol-sulfonamidylpropyl]-acridinium-9-carboxylate [$N^{10}$-2,7-(OMHEG-SP)$_3$-DMAE-AC-NHS]

(a) Synthesis of 2',6'-dimethyl-4'-carboxyphenyl-$N^{10}$-2,7-tris[O-methoxyhexa(ethylene)glycol-sulfonamidylpropyl]-acridinium-9-carboxylate NSP-2,7-(OSP)$_2$-DMAE (10 mg, 0.0129 mmol) was dissolved in methanol (5 mL), and cooled in an ice-bath. Thionyl chloride (0.5 mL) was added drop wise and the reaction was stirred briefly in the ice-bath and then warmed to room temperature and stirred for 16 hours. HPLC analysis using a $C_{18}$ column from Phenomenex, 4.6 mm×30 cm, and a 30 minute gradient of 10%→70% MeCN in water, each with 0.05% trifluoroacetic acid, at a flow rate of 1 mL/min, showed complete conversion to product eluting at 12 minutes. The solvent was removed under reduced pressure and the residue was suspended in ethyl acetate (~5 mL) and evaporated to dryness.

The methyl ester was then suspended in thionyl chloride (1.5 mL) and heated at reflux for 1 hour under a nitrogen atmosphere. It was then cooled to room temperature and the thionyl chloride was removed under vacuum. The residue was rinsed with anhydrous ether (~5 mL) several times and then dried under vacuum. It was then treated with a solution of methoxy hexa(ethylene)glycol amine (synthesized using procedures described in U.S. Pat. No. 6,664,043 and Yamashita et al. *J. Am. Chem. Soc.* 1995, 117, 6249-6253) (0.1 mL) dissolved in dichloromethane (2 mL).

The reaction was stirred at room temperature. After one hour, HPLC analysis indicated complete conversion to product eluting at 21 minutes. The solvent was then removed under reduced pressure and the crude product was suspended in 1 N HCl (~5 mL) and refluxed under a nitrogen atmosphere for 2 hours to hydrolyze the methyl ester. It was then cooled to room temperature and analyzed by HPLC which, indicated complete hydrolysis of the methyl ester. The product was observed to elute at 19.5 minutes.

The product was purified by preparative HPLC using a $C_{18}$ YMC, 20×300 mm column using the above gradient and a solvent flow rate of 16 mL/min. The HPLC fraction containing product was frozen at −80° C. and lyophilized to dryness. Yield=3.8 mg (~20%), MALDI-TOF MS 1602.92 (calc.).

b) Synthesis of 2',6'-dimethyl-4'-carboxycaproylamidocarbonylphenyl-$N^{10}$-2,7-tris[O-methoxyhexa(ethylene)glycol-sulfonamidylpropyl]-acridinium-9-carboxylate A solution of $N^{10}$-2,7-(OMHEG-SP)$_3$-DMAE (3.8 mg, 2.4 umoles) from in anhydrous DMF (1 mL) was treated with diisopropylethylamine (2.0 uL, 2.4×5 umoles) and TSTU (4 mg, 2.4×5 umoles). The reaction was stirred at room temperature for 30 minutes and then HPLC analysis using a $C_{18}$ column from Phenomenex, 4.6 mm×30 cm, and a 30 minute gradient of 10%→100% MeCN in water, each with 0.05% trifluoroacetic acid, at a flow rate of 1 mL/min, showed complete conversion to product eluting at 16.2 minutes (starting material elutes at 15.3 minutes). The DMF solution was cooled in an ice-bath and then added in 0.1 mL portions to an ice-cold solution of 6-aminocaproic acid (6 mg, 47.4 umoles) dissolved in 0.1 M sodium bicarbonate (1 mL). The reaction was then warmed to room temperature and stirred for an hour. HPLC analysis indicated complete conversion to product eluting at 15.4 minutes. The product was purified by preparative HPLC using a $C_{18}$ YMC 20×300 mm column. The HPLC fraction was frozen at −80° C. and lyophilized to dryness. Yield=3.3 mg (81%); MALDI-TOF MS 1719 obs. (1717.1 calc.).

c) Synthesis of 2',6'-dimethyl-4'-N-succinimidyloxycapropylamidocarbonylphenyl-$N^{10}$-2,7-tris[O-methoxyhexa(ethylene)glycolsulfonamidylpropyl]-acridinium-9-carboxylate A solution of $N^{10}$-2,7-(OMHEG-SP)$_3$-DMAE-AC (3.3 mg, 2 umoles) from step (a) in anhydrous DMF (1 mL) was treated with diisopropylethylamine (1.8 uL, 10 umoles) and TSTU (3 mg, 10 umoles). The reaction was stirred at room temperature after 15 minutes, HPLC analysis as described above in section (a) showed complete conversion to product eluting at 16.2 minutes. The product was purified by preparative HPLC and the HPLC fraction was frozen at −80° C. and lyophilized to dryness. Yield=2.2 mg (63%); MALDI-TOF MS (1814.1 calc.)

The following reactions describe the synthesis of $N^{10}$-2,7-(OMHEG-SP)$_3$-DMAE-AC-NHS.

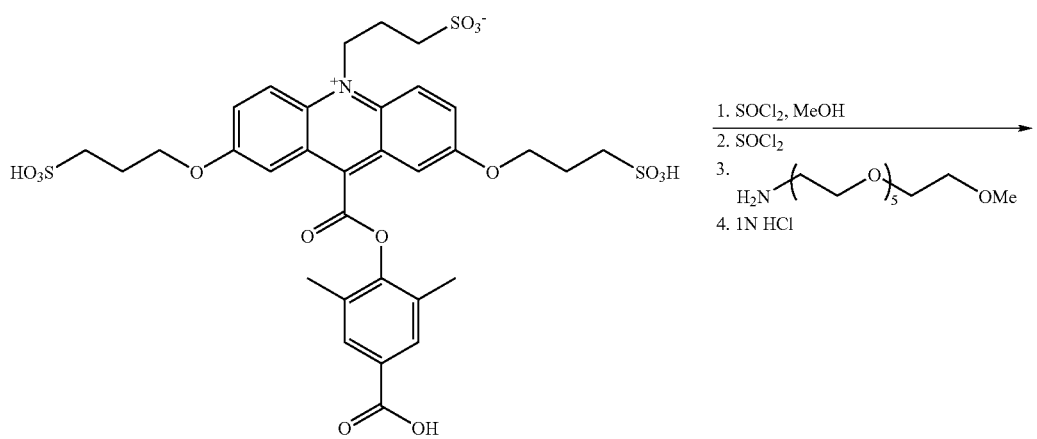

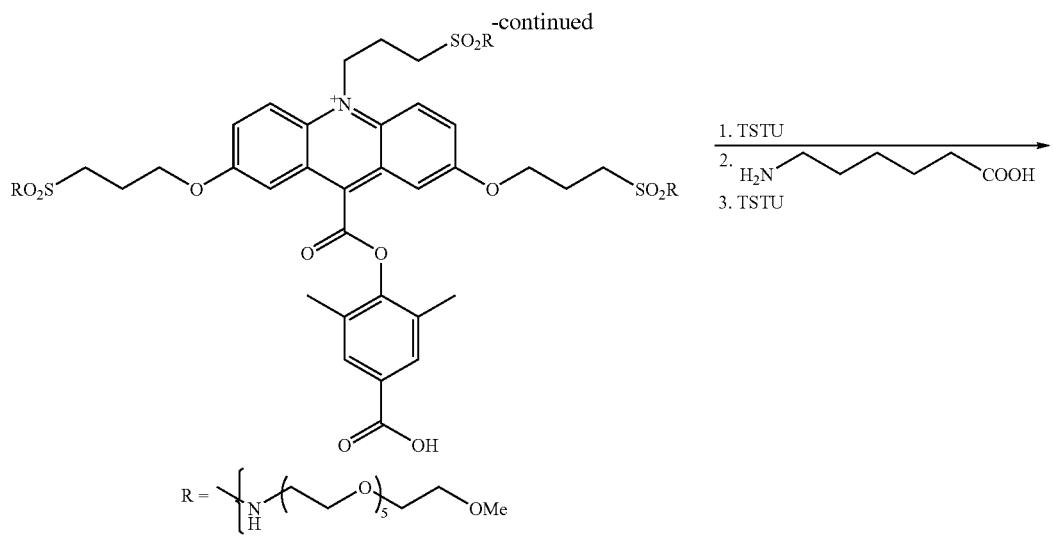

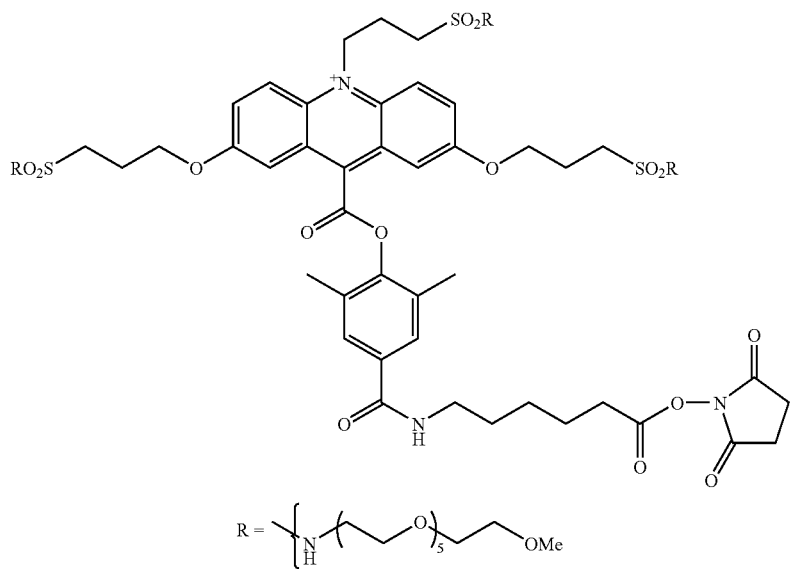

Example 12

Synthesis of 2',6'-dimethyl-4'-N-succinimidyloxy-glutaryl-amidohexa(ethylene)glycol-amidocarbonylphenyl-N[10]-methoxyhexa(ethylene)glycol-sulfonamidylpropyl-2,7-dimethoxy-acridinium-9-carboxylate [N[10]-(OMHEG-SP)-2,7-(OMe)$_2$-DMAE-HEG-Glutarate-NHS]

(a) Synthesis of 2',6'-dimethyl-4'-carboxyphenyl-N[10]-methoxyhexa(ethylene)glycol-sulfonamidylpropyl]-2,7-dimethoxy-acridinium-9-carboxylate NSP-2,7-dimethoxy-DMAE benzyl ester (22 mg) from Example 1 was dissolved in thionyl chloride and the solution was heated in an oil-bath at 55° C. under a nitrogen atmosphere for 4 hours. The thionyl chloride was removed under reduced pressure and the residue was rinsed with anhydrous ether and dried under vacuum. This residue was treated with a solution of methoxy hexa(ethylene)glycol amine (0.1 mL) in dichloromethane (2 mL). The reaction was stirred at room temperature. After 30 minutes, HPLC analysis-using a $C_{18}$ column from Phenomenex, 4.6 mm×30 cm, and a 30 minute gradient of 10%→100% MeCN in water, each with 0.05% trifluoroacetic acid, at a flow rate of 1 mL/min, showed complete conversion to product eluting at 19 minutes. The solvent was them removed under reduced pressure and the resulting oil was stirred in 30% HBr/AcOH (2 mL) at room temperature for 6 hours to effect the debenzylation of the carboxylic acid. Ether (10 mL) was then added and a dark red oil separated out. The ether was decanted and the oil was rinsed several times with ether. It was then dissolved in DMF (2-3 mL) and analyzed by HPLC which, indicated product eluting at 15 minutes. The product was purified by preparative HPLC using a YMC $C_{18}$, 20×300 mm column. The HPLC fractions containing product were frozen at −80° C. and lyophilized to dryness. Yield=5.3 mg (19%); MALDI-TOS MS 831.9 calc.

(b) Synthesis of 2',6'-dimethyl-4'-aminohexa(ethylene)glycolamidocarbonylphenyl-$N^{10}$-methoxyhexa(ethylene)glycol-sulfonamidylpropyl 2,7-dimethoxy-acridinium-9-carboxylate A solution of $N^{10}$-(OMHEG-SP)-2,7-(OMe)$_2$-DMAE (5.3 mg, 6.4 umoles) from step (a) in anhydrous DMF (1 mL) was treated with diisopropylethylamine (5.6 uL, 17 umoles) and TSTU (6 mg, 10.2 umoles). The reaction was stirred at room temperature. After 30 minutes, HPLC analysis as described above in section (a) indicated complete conversion to product eluting at 16.3 minutes. The reaction mixture was added drop wise to a solution of diamino hexa(ethylene)glycol (10 mg, 0.0354 mmol) in DMF (0.5 mL). The reaction was stirred at room temperature for 30 minutes and then analyzed by HPLC which, indicated complete conversion to product eluting at 14 minutes. The product was purified by preparative HPLC using a YMC $C_{18}$, 20×300 mm column. The HPLC fraction was frozen at −80° C. and lyophilized to dryness. Yield=3.7 mg (53%).

(c) Synthesis of 2',6'-dimethyl-4'-N-succinimidyloxyglutarylamidohexa(ethylene)-glycolamidocarbonylphenyl-$N^{10}$-methoxyhexa(ethylene)glycol-sulfonamidylpropyl 2,7-dimethoxy-acridinium-9-carboxylate A solution of $N^{10}$-(OMHEG-SP)-2,7-(OMe)$_2$-DMAE-HEG-NH$_2$ (3.7 mg, 3.4 umoles) from step (b) in anhydrous methanol (1 mL) was treated with diisopropylethylamine (3 uL, 17 umoles) and glutaric anhydride (2 mg, 17 umoles). The reaction was stirred at room temperature and after 30 minutes, HPLC analysis as described in section (a) indicated complete conversion to product eluting at 14.6 minutes. The reaction mixture was evaporated to dryness. The residue was dissolved in DMF (1 mL) and treated with diisopropylethylamine (3 uL) and TSTU (6 mg, 17 umoles). The reaction was stirred at room temperature and after 30 minutes, HPLC analysis indicated product eluting at 15.3 minutes. The product was purified by preparative HPLC using a $C_{18}$ YMC, 20×300 mm column. The HPLC fraction containing product was frozen at −80° C. and lyophilized to dryness. Yield=1.7 mg (39%). MALDI-TOF-MS 1303.5 calc.

The following reactions describe the synthesis of $N^{10}$-(OMHEG-SP)-2,7-(OMe)$_2$-DMAE-HEG-Glutarate-NHS.

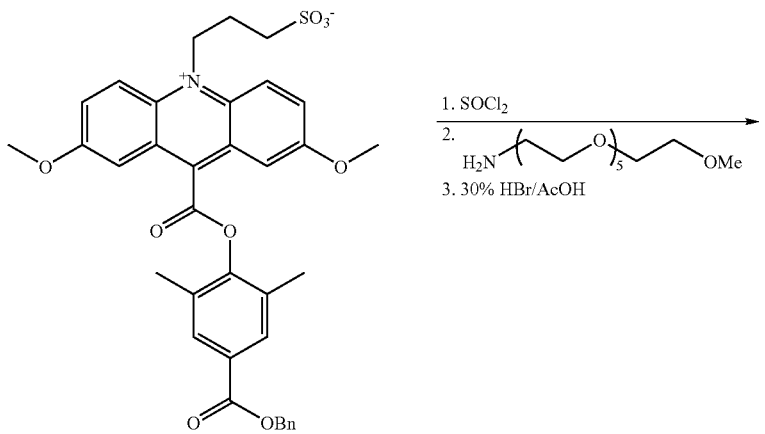

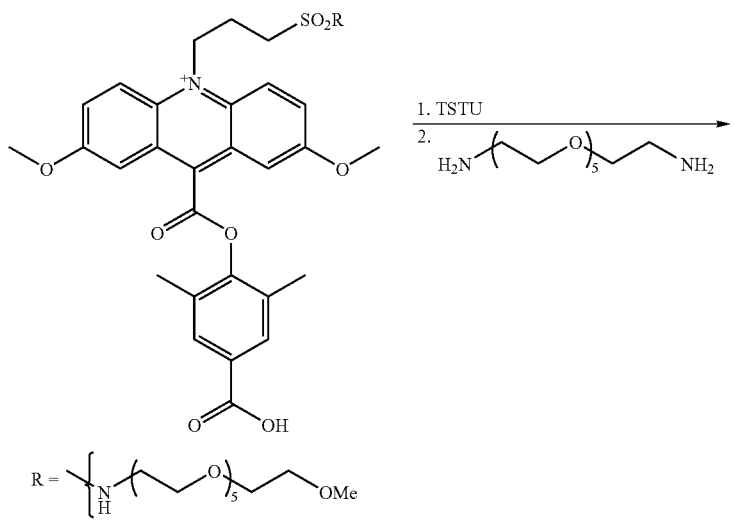

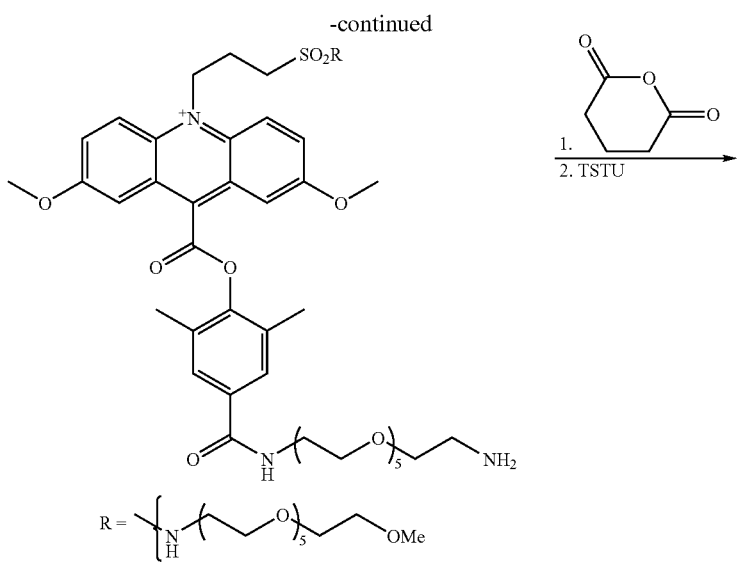

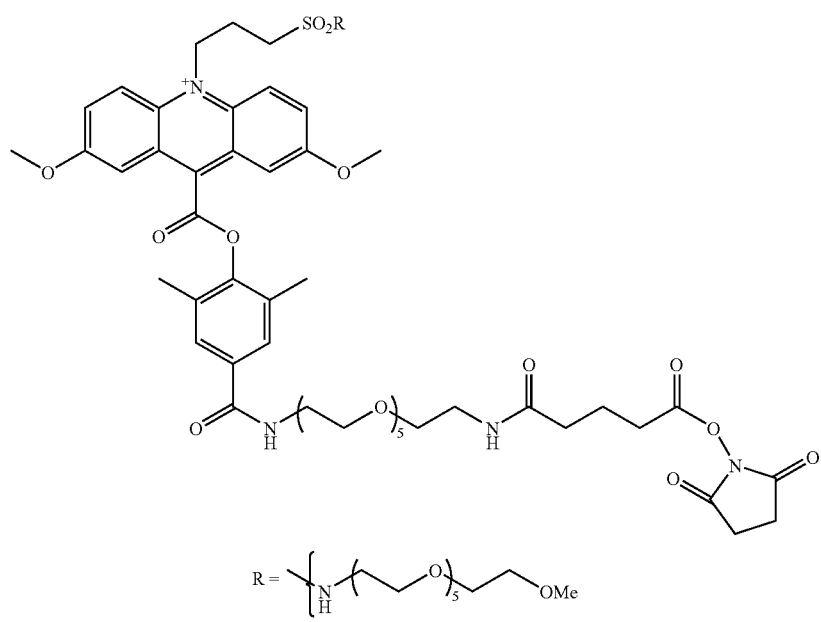

Example 13

Synthesis of 3-[9-({5-carboxypentyl)[4-methylphenyl)sulfonyl]amino}carbonyl)-10-acridiniumyl]-1-propanesulfonate (NSP-AS) and its N-succinimidyl ester (NSP-AS-NHS)

NSP-AS was synthesized using the procedures reported by Adamczyk et al., *Tetrahedron*, vol. 55, pp. 10899-10914 (1999) as follows. NSP-AS (8.8 mg, 14.4 umoles) was dissolved in anhydrous DMF (1 mL) and was treated with diisopropylethylamine (5 uL, 2 equivalents) and TSTU (8.2 mg, 1.5 equivalents). The reaction was stirred at room temperature. After 30 minutes HPLC analysis using a $C_{18}$ column from Phenomenex, 4.6 mm×30 cm, and a 30 minute gradient of 10%→70% MeCN in water, each with 0.05% trifluoroacetic acid, at a flow rate of 1 mL/min, showed complete conversion to product eluting at 17.7 minutes with no starting material at 15.5 minutes. The product was purified by preparative HPLC using a $C_{18}$, 20 mm×30 cm column. The product fraction, containing product was frozen at −80° C. and lyophilized to dryness. Yield=5-8 mg (57%)

The following reactions describe the synthesis of NSP-AS-NHS ester.

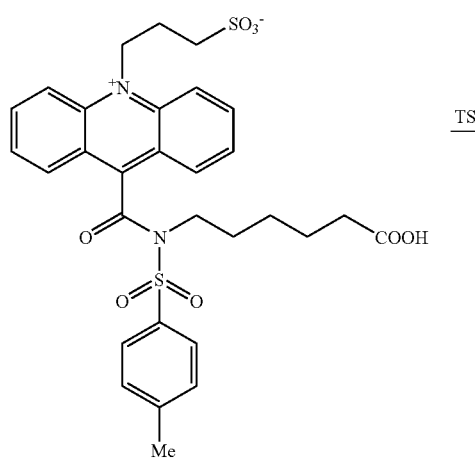

TSTU, DMF →

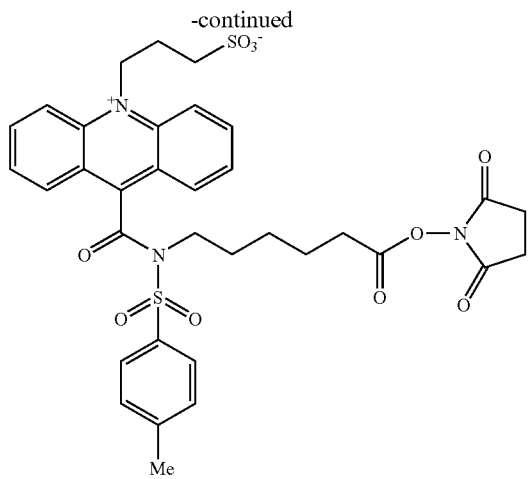

Example 14

Synthesis of 3-[9-({5-carboxypentyl)[4-methylphenyl)sulfonyl]amino}carbonyl)-2,7-dimethoxy-10-acridiniumyl]-1-propanesulfonate (NSP-2,7-dimethoxy-AS) and its N-succinimidyl ester (NSP-AS-NHS)

These compounds were synthesized using the procedures and reference cited in Examples 7-13.

The following reactions describe the synthesis of NSP-2, 7-(OMe)$_2$-AS and its NHS ester.

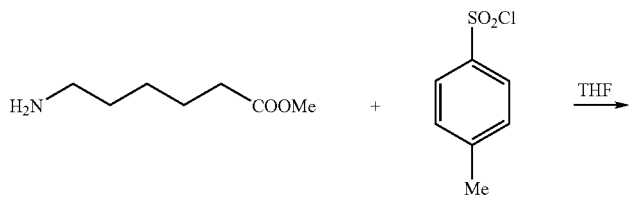

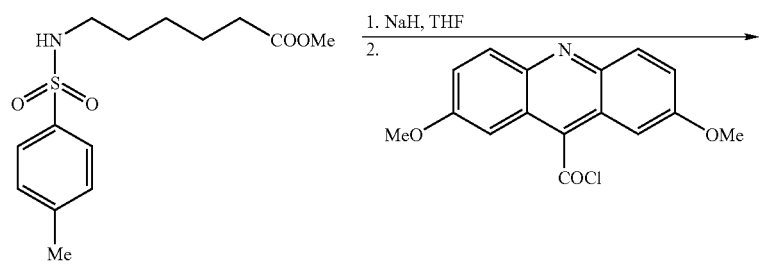

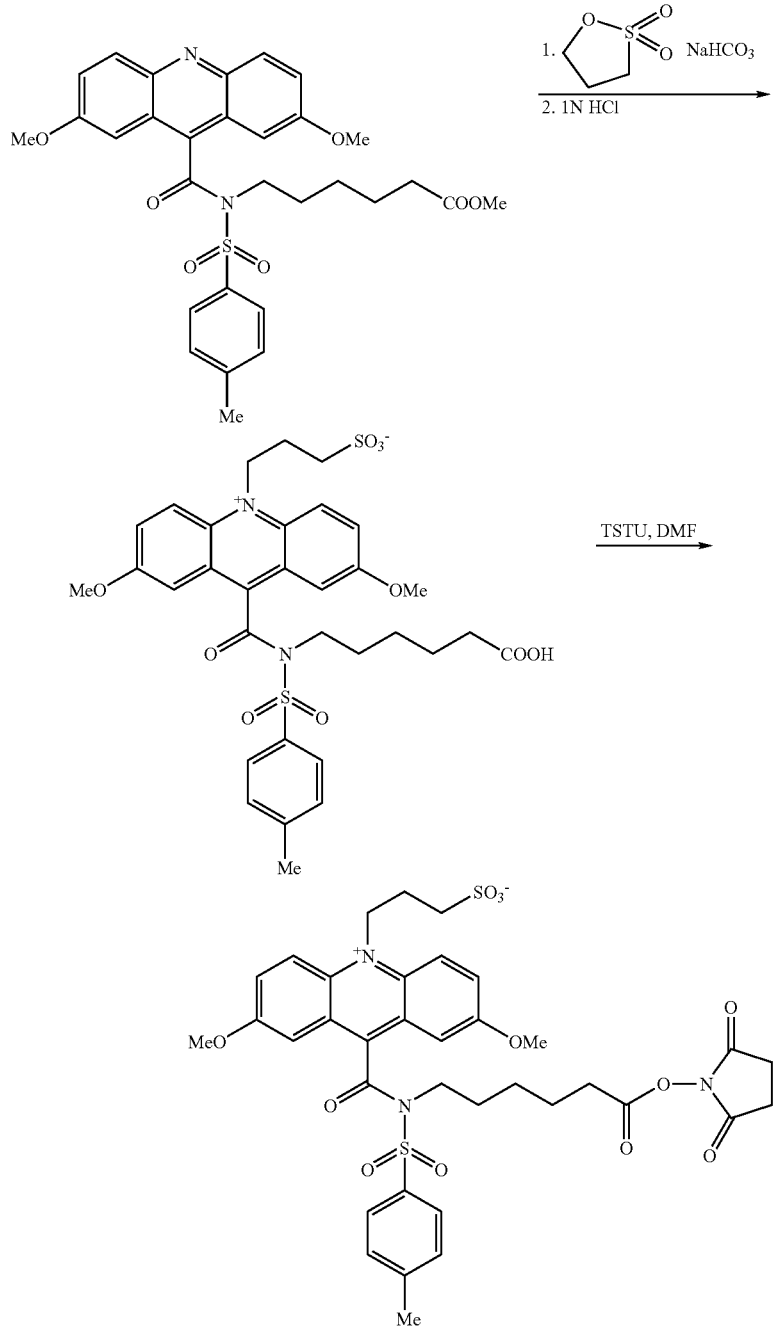

Example 15

Synthesis of NSP-2,7-(OMHEG)$_2$-DMAE-HEG-Theophylline Conjugate

A solution of 8-carboxypropyltheophylline (Sigma, 5 mg, 18.7 umoles) in anhydrous DMF (1 mL) was treated with diisopropylethylamine (3.2 uL, 1 equivalent) and HATU (7 mg, 1 equivalent). The reaction was stirred at room temperature for 10 minutes and then a solution of NSP-2,7-(OMHEG)$_2$-DMAE-HEG-NH$_2$ (5 mg, 3.7 umoles) from Example 9, step (f) was added in anhydrous DMF (1 mL) along with diisopropylethylamine (2 uL). This reaction was stirred at room temperature. After 16 hours HPLC analysis-using a C$_{18}$ column from Phenomenex, 4.6 mm×30 cm, and a 30 minute gradient of 10%→70% MeCN in water, each with 0.05% trifluoroacetic acid, at a flow rate of 1 mL/min, showed complete conversion to product eluting at 18 minutes. The product was purified by preparative HPLC using a C$_{18}$ YMC, 20×300 mm column. The HPLC fraction containing product was frozen at −80° C. and lyophilized to dryness. Yield=4.0 mg (67%). MALDI-TOF-MS 1593.8 calc. 1596.7 obs.

The following reactions describe the synthesis of NSP-2,7-(OMHEG)$_2$-DMAE-HEG-Theophylline.

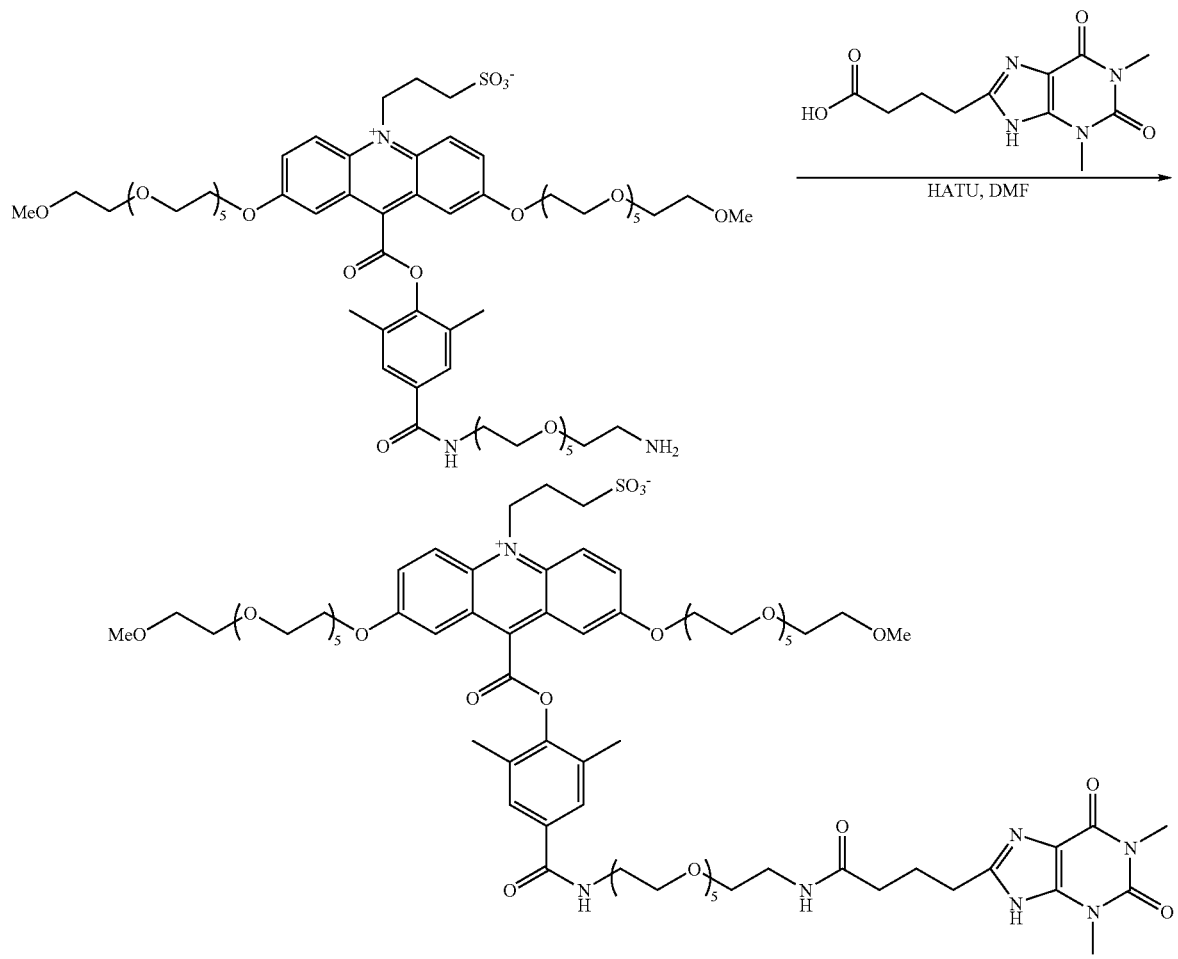

Example 16

General Procedure for Protein Labeling with Acridinium Compounds

The anti-TSH murine monoclonal antibody (1 mg, 6.67 nmoles, stock solution 5 mg/mL, 0.2 mL) was diluted with 300 uL of 0.1 M sodium phosphate, pH 8. The protein solutions were treated with DMF solutions of various acridinium esters as follows:

a) For labeling with 20 equivalents NSP-DMAE-HEG-Glutarate-NHS ester, 63 uL of a 2 mg/mLDMF solution of the compound was added;
b) for labeling with 20 equivalents of NSP-2,7-(OMTEG)$_2$-DMAE-NHS ester, 46 uL of a 2.67 mg/mL DMF solution of the compound was added;
c) for labeling with 20 equivalents of NSP-2,7-(OMTEG)$_2$-DMAE-HEG-Glutarate-NHS ester, 52 uL of a 3.33 mg/mL DMF solution was added;
d) for labeling with 20 equivalents of NSP-2,7-(OMHEG)$_2$-DMAE-AC-NHS ester, 43 uL of a 4 mg/mL DMF solution was added and;
e) for labeling with 20 equivalents of NSP-2,7-(OMHEG)2-DMAE-HEG-Glutarate-NHS ester, 52 uL of a 3.33 mg/mL DMF solution was added.

All reactions were stirred at 4° C. for 16 hours and were then transferred to 2 mL amicon filters(MW 30,000 cutoff) and diluted with 1.5 mL de-ionized water. The volume was reduced to ~0.1 mL by centrifuging at 4500 G. The concentrated conjugate solutions were diluted with 2 mL de-ionized water and centrifuged again to reduce the volume. This process was repeated a total of four times. Finally, the concentrated conjugates were diluted with 0.1 mL de-ionized water.

These solutions were used for MALDI-TOF (Matrix-Assisted Laser Desorption Ionization-Time of Flight) mass spectral analysis, using the Voyager-DE instrument from Perkin-Elmer, to measure acridinium compound incorporation. Typically, this entailed measuring the molecular weight of the unlabeled antibody and the labeled antibody. The acridinium compound label contributed the difference in mass of these two measurements. By knowing the molecular weight of the specific acridinium compound label, the extent of label incorporation of that specific acridinium compound could thus be calculated.

The number of labels per antibody molecule for NSP-DMAE-HEG-glutarate, NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate were 8, 8, 7, 10 and 8 respectively.

Protein concentrations were determined by a commercial calorimetric assay.

Chemiluminescence from the conjugates was measured by first diluting the conjugates in 10 mM phosphate pH 8 containing 150 mM NaCl, 0.05% BSA and 0.01% sodium azide and then conducting measurements in a ACS:180®-Automated Chemiluminescent Immunoassay System instrument from Bayer Diagnostics. A typical measurement involves triggering chemiluminescence from 25 uL of the diluted conjugate solution with the addition of two reagents. Reagent 1 is a solution of 0.5% hydrogen peroxide in 0.1 N nitric acid. Reagent 2 is 0.25 N sodium hydroxide. Light was measured for a total of 5 seconds. Under these conditions, >90% of the light from each sample was collected. The output from luminometer instrument is expressed as RLUs (Relative Light Units). These values were normalized to that of NSP-DMAE which was assigned a relative chemiluminesence quantum yield of 1.0.

Labeling reactions with other acridinium compounds were carried out in a similar manner.

Example 17

Chemiluminescence and Emission Wavelength Measurements of Acridinium Compounds

Chemiluminescence from the various acridinium compounds was measured as described for the protein conjugates in Example 16. A solution, typically 1 mg/mL in DMF, of the various HPLC-purified compounds, was serially diluted into 10 mM phosphate pH 8 containing 150 mM NaCl, 0.05% BSA and 0.01% sodium azide and then chemiluminescence measurements were conducted in a luminometer (MLA1™, Bayer Diagnostics). The relative quantum yield of NSP-DMAE was assigned a value of 1.0.

Emission wavelength from the acridinium compounds was measured using FSSS (Fast Spectral Scanning System) camera from Photoresearch Inc. In a typical measurement, 25-50 uL of a 1 mg/mL DMF solution of the acridinium compound was diluted with DMF (~0.3 mL). Chemiluminescence was triggered by the addition of the two reagents described in example 10. Just prior to the addition of the second reagent, the shutter of the camera was opened and light was collected for 5 seconds. The output of the instrument is a graph of light intensity versus wavelength. Emission maxima for each compound are listed in Table 1.

Example 18

Theophylline Immunoassay Using a High Quantum Yield Acridinium Compound as Chemiluminescent Label A high quantum yield acridinium compound was tested as a label in a competitive immunoassay for comparison with a control acridinium compound used separately as a label in the same competitive immunoassay. A label is an atom, molecule, compound, ion, radical or macromolecule, that when conjugated or complexed to a ligand, or when conjugated or complexed to a receptor, enables qualitative or quantitative identification, assessment, characterization, detection or measurement of an analyte or analytes in an assay.

In this example the high quantum yield acridinium compound NSP-2,7-(OMHEG)$_2$-DMAE-HEG was the label to be tested and to be compared to the control acridinium compound NSP-DMAE-HEG, which is the actual label in the commercially marketed Bayer Diagnostics ACS:180® Theophylline Assay. The control acridinium compound NSP-DMAE-HEG is referred to as a control because it is the actual label in the commercially available product, the Bayer Diagnostics ACS:180® Theophylline Assay.

The high quantum yield acridinium compound NSP-2,7-(OMHEG)$_2$-DMAE-HEG has a higher quantum yield than the control acridinium compound NSP-DMAE-HEG, which has a lower quantum yield. When used as a label in the Bayer Diagnostics ACS:180® Theophylline Assay, the high quantum yield acridinium compound NSP-2,7-(OMHEG)$_2$-DMAE-HEG was expected to enhance the Bayer Diagnostics ACS:180® Theophylline Assay when compared with the lower quantum yield control acridinium compound NSP-DMAE-HEG, when also used separately as a label in the Bayer Diagnostics ACS:180® Theophylline Assay.

An assay, which is synonymous with test, is a method, a reaction or the act of qualitative or quantitative identification, assessment, characterization, detection or measurement of the properties or amount of a substance, substances, analyte or analytes or their parts.

The Bayer Diagnostics ACS:180® Theophylline Assay is one of a series of commercially marketed immunoassays manufactured by Bayer Diagnostics for application on the Bayer Diagnostics ACS:180® (Automated Chemiluminescent Immunoassay System).

An immunoassay, which is synonymous with immunologic assay or immunochemical assay, is a method, a reaction or the act of qualitative or quantitative identification, assessment, characterization, detection or measurement of the properties or amount of a substance, substances, analyte or analytes or their parts by action of an antigen, epitope, hapten, ligand, carrier, or macromolecule with a receptor that is usually an antibody or other biological receptor.

The Bayer Diagnostics ACS:180® Theophylline Assay is a competitive immunoassay which uses a chemiluminescent acridinium compound conjugate of theophylline, which is NSP-DMAE-HEG-theophylline, for measurement of theophylline in a sample.

A sample is a material, which may contain an analyte or analytes. In reference to the Bayer Diagnostics ACS:180® Theophylline Assay, the sample was serum, which might contain analyte.

An analyte is a substance or substances, which may be present in a sample, and which can be qualitatively or quantitatively identified, assessed, characterized, detected or measured in an assay. In reference to the Bayer Diagnostics ACS:180® Theophylline Assay the analyte is theophylline.

Both the high quantum yield acridinium compound NSP-2,7-(OMHEG)$_2$-DMAE-HEG and the control acridinium compound NSP-DMAE-HEG were labels conjugated to a ligand. A ligand is an atom, molecule, compound, ion or radical that binds specifically to a macromolecule: that macromolecule being a receptor. In reference to the Bayer Diagnostics ACS:180® Theophylline Assay the ligand is theophylline.

An acridinium compound conjugated to a ligand is a tracer. A tracer is a conjugate or complex of a label with a ligand, or is a conjugate or complex of a label with a receptor, which by action of the label, enables qualitative or quantitative identification, assessment, characterization, detection or measurement of an analyte or analytes in an assay.

In the Bayer Diagnostics ACS:180® Theophylline Assay reagents were mixed with the sample to start the assay reaction. A reagent is a substance or substances which have chemical action with another substance or other substances, but more specifically with respect to an assay, an assay reagent is a substance or substances, other than and not including the sample, which will react with an analyte, if the analyte is present in a sample.

In reference to the Bayer Diagnostics ACS:180® Theophylline Assay there were two assay reagents. The first assay reagent was the solid phase. The solid phase is an assay reagent consisting of a ligand or a receptor conjugated to or complexed to, directly or indirectly to a separable material. In reference to the Bayer Diagnostics ACS:180® Theophylline Assay the solid phase is a receptor on magnetically separable paramagnetic particles.

A receptor is a macromolecule, which specifically binds one or more analytes, antigens, atoms, compounds, epitopes, haptens, ions, ligands, molecules, radicals, tracers or other receptors. In reference to the Bayer Diagnostics ACS:180® Theophylline Assay, the receptor is anti-theophylline antibody which binds both the analyte, which is theophylline, and the tracer.

The second assay reagent is the tracer. In reference to the Bayer Diagnostics ACS:180® Theophylline Assay, the tracer, which is synonymous with Lite Reagent, is a conjugate of a label, which is an acridinium compound, and a ligand, which like the analyte is theophylline. Since, in reference to the Bayer Diagnostics ACS:180® Theophylline Assay, the ligand is theophylline and is the same as the analyte, which is also theophylline, both the analyte and the tracer will bind to the receptor in the reaction mixture.

The reaction mixture is a combining of reagents, but more specifically with respect to an assay, the assay reaction mixture is a combining of sample and assay reagents in an assay or assay reaction. A reaction is the action of a substance or substances on another substance or other substances, but more specifically with respect to an assay, the assay reaction is the action of assay reagents on a sample in an assay.

In reference to the Bayer Diagnostics ACS:180® Theophylline Assay, the assay reaction mixture contains sample, solid phase and tracer, and the assay reaction is the action of the solid phase and tracer on the sample, which may contain analyte.

In reference to the Bayer Diagnostics ACS:180® Theophylline Assay, the assay reaction is the binding of both the analyte, which is theophylline if present in the sample, and the tracer, which is the acridinium compound conjugate of the ligand theophylline, to the same solid phase, which binds either an analyte or a tracer at any one receptor, but does not bind both an analyte and a tracer at the same time at the same receptor.

Since the solid phase has a smaller amount of receptor, with respect to the total amount of analyte, when present in the sample, then the total of the amount of analyte plus tracer in the assay reaction mixture is greater than the amount of the receptor on the solid phase. Thus the total of the amount of analyte plus tracer cannot bind to the solid phase in totality.

Consequently, the presence of analyte in a sample will block or compete with the binding of the tracer to the solid phase in the assay reaction mixture, where the amount of blocking or competition depends on the amount of analyte present in the sample.

Therefore, the amount of analyte in a sample is inversely correlated to the amount of tracer that will bind to the solid phase in an assay reaction mixture. In reference to the Bayer Diagnostics ACS:180® Theophylline Assay, the analyte, which is theophylline if present in the sample, blocks or competes with the tracer, which is an acridinium compound conjugate of theophylline, for a limited amount of anti-theophylline antibody, which is the receptor on magnetically separable paramagnetic particles.

The Bayer Diagnostics ACS:180® automatically performed the following steps for the Bayer Diagnostics ACS:180® Theophylline Assay. First, 0.020 mL of each of fourteen samples was dispensed into a separate cuvet. A cuvet is an optically transparent or translucent container that holds the assay reaction mixture and in which the assay reaction takes place.

The fourteen samples each contained separate known amounts of theophylline. The amounts of theophylline given as concentrations in each of these fourteen samples were 0, 1.40, 2.10, 2.80, 4.20, 5.60, 9.21, 15.6, 32,7, 68.3, 129, 288, 500, and 1000 micromolar. The amounts of theophylline given as numbers of molecules in each of these same fourteen samples were 0, 0.028, 0.042, 0.056, 0.084, 0.112, 0.184, 0.313, 0.655, 1.37, 2,59, 5.76, 10.0, and 2.00 picomoles, respectively.

Next, the Bayer Diagnostics ACS:180® dispensed two assay reagents together into each cuvet and mixed the assay reagents with the sample within each cuvet. The first of the two assay reagents was 0.450 mL of solid phase, which contained 8.7 picomoles of anti-theophylline antibody on magnetically separable paramagnetic particles.

The second of the two assay reagents was 0.100 mL of tracer, which was 0.026 picomole of acridinium compound conjugated to theophylline. Both the high quantum yield acridinium compound NSP-2,7-(OMHEG)$_2$-DMAE-HEG and the control acridinium compound NSP-DMAE-HEG were tested separately as labels conjugated to theophylline, in the form of two tracers: NSP-2,7-(OMHEG)$_2$-DMAE-HEG-theophylline and NSP-DMAE-HEG-theophylline, respectively.

The assay reaction proceeded for 7.5 minutes at 37° C. The Bayer Diagnostics ACS:180® finished the ACS:180® Theophylline Assay by magnetically separating the solid phase from other assay reagents, then removing fluid from the cuvet and then washing the solid phase in the cuvet with water.

Chemiluminescence from acridinium compound on the solid phase was initiated with subsequent light emission with sequential additions of 0.30 mL each of Bayer Diagnostics ACS:180® Reagent 1 and Bayer Diagnostics ACS:180® Reagent 2. Bayer Diagnostics ACS:180® Reagent 1 was 0.1 M nitric acid and 0.5% hydrogen peroxide. Bayer Diagnostics ACS:180® Reagent 2 was 0.25 M sodium hydroxide and 0.05% cetyltrimethylanmuonium chloride.

The Bayer Diagnostics ACS:180® measured the chemiluminescence in each cuvet with each cuvet corresponding to a single assayed sample. The Bayer Diagnostics ACS:180® measured the chemiluminescence as relative light units (RLUs). In reference to the Bayer Diagnostics ACS:180® Theophylline Assay, the amount of analyte is inversely correlated to the amount of tracer that will bind to the solid phase.

Consequently, the amount of analyte is inversely correlated to the number of RLUs measured by the Bayer Diagnostics ACS:180®. This means that the greater the amount of the analyte theophylline in a sample then fewer RLUs are measured with respect to lower amounts of the analyte theophylline in a sample where more RLUs are measured.

Normalization to percentage of chemiluminescence measured in the absence of analyte was calculated for comparison of the relative chemiluminescence given for each amount of analyte for the high quantum yield acridinium compound, NSP-2,7-(OMHEG)$_2$-DMAE-HEG, compared with the control acridinium compound NSP-DMAE-BEG.

The greater the spacing between chemiluminescence values for successive amounts of analyte is an indicator of enhanced sensitivity. The greater the chemi-luminescence difference between small amounts of analyte from the chemiluminescence obtained in the absence of analyte, permits better differentiation of small amounts of analyte and the absence of analyte in competitive assay, thereby enhancing sensitivity.

In reference to the Bayer Diagnostics ACS:180® Theophylline Assay relative to the lower quantum yield label NSP-DMAE-HEG, the high quantum yield acridinium compound NSP-2,7-(OMHEG)$_2$-DMAE-HEG generated greater differentiation between small amounts of theophylline and the absence of theophylline when used as a competitive immunoassay label.

The slope of the line generated for each tracer using the Bayer Diagnostics ACS:180® Theophylline Assay is an indicator of sensitivity. The greater the absolute magnitude of the slope of the line for a particular tracer or label in a competitive immunoassay, the more distant is the chemiluminescence for a particular amount of analyte from the chemiluminescence from a sample with no analyte and the assay is better able to measure the difference between the presence of analyte and the absence of analyte.

In reference to the Bayer Diagnostics ACS:180® Theophylline Assay, the high quantum yield acridinium compound label NSP-2,7-(OMHEG)$_2$-DMAE-HEG gave enhanced slope relatives to the control acridinium compound label NSP-DMAE-HEG.

The greater absolute magnitude of the slope generated by the high quantum yield acridinium compound label for both the high amounts and particularly the low amounts of theophylline, relative to the control acridinium compound and NSP-DMAE-HEG, indicates an enhancement of sensitivity for the Bayer Diagnostics ACS:180® Theophylline Assay using high quantum yield acridinium compounds as immunoassay labels.

For the Bayer Diagnostics ACS:180® Theophylline Assay, which is a competitive immunoassay, sensitivity is the least measurable non-zero amount of analyte. The least measurable non-zero amount of analyte in the Bayer Diagnostics ACS:180® Theophylline Assay is the amount of analyte corresponding to the greatest measured chemiluminescence that is less than the difference of the chemiluminescence measured in the absence of analyte minus two standard deviations of chemiluminescence measured in the absence of analyte.

For example, in competitive immunoassays where the following representations are given:

n=positive integer greater than 0.

x=the measured amount of analyte corresponding to y, where x0<x1<x2<x3< . . . <xn are successively greater measured amounts of analyte.

y=the chemiluminescence measured for an amount of analyte, represented by x, where y0>y1>y2>y3> . . . >yn are successively lesser values of chemiluminescence, measured for x0<x1<x2<x3< . . . <xn, respectively.

x0=a zero amount of analyte or the amount of analyte equal to zero.

y0=the chemiluminescence measured for an amount of analyte equal to zero, which is x0.

s=one standard deviation of y0.

Then the sensitivity=xn for yn<y0−2s, when n=the least, positive, nonzero integer.

The sensitivity for the Bayer Diagnostics ACS:180® Theophylline Assay using the high quantum yield acridinium compound NSP-2,7-(OMHEG)$_2$-DMAE-HEG was 1.4 µM. The sensitivity for the Bayer Diagnostics ACS:180® Theophylline Assay using the control acridinium compound NSP-DMAE-HEG was 4.2 µM. The quotient of 4.2 µM and 1.4 µM is 3.

The Bayer Diagnostics ACS:180® Theophylline Assay using the high quantum yield acridinium compound as a label measured an amount of theophylline that was three-fold smaller than the commercially marketed Bayer Diagnostics ACS:180® Theophylline Assay that used the lower quantum yield control acridinium compound as a label.

The high quantum yield acridinium compound NSP-2,7-(OMHEG)$_2$-DMAE-HEG enhanced the sensitivity of the Bayer Diagnostics ACS:180® Theophylline Assay three-fold when compared to the control acridinium compound NSP-DMAE-HEG.

The example establishes that when used as chemiluminescent immunoassay labels the enhanced chemiluminescent light emission from high quantum yield acridinium compounds enhances the sensitivity of competitive immunoassays.

Example 19

TSH Immunoassay Using High Quantum Yield Acridinium Compounds as Chemiluminescent Labels High quantum yield acridinium compounds were tested as labels in a sandwich immunoassay for comparison with control acridinium compounds used separately as labels in the same sandwich immunoassay.

In this example the high quantum yield acridinium compounds, NSP-2,7-(OMTEG)$_2$-DMAE, NSP-2,7-(OMTEG)$_2$-DMAE-HEG-glutarate, NSP-2,7-(OMHEG)$_2$-DMAE-HEG-glutarate and NSP-2,7-(OMHEG)$_2$-DMAE-AC were the chemiluminescent labels to be tested and to be compared to the control acridinium compound NSP-DMAE-HEG-glutarate.

The high quantum yield acridinium compounds have higher quantum yields than the control acridinium compound NSP-DMAE-HEG-glutarate, and were expected to enhance the Bayer Diagnostics ACS:180® TSH3 Assay.

The Bayer Diagnostics ACS:180® TSH3 Assay is a sandwich immunoassay which uses a chemiluminescent acridinium compound conjugate of anti-TSH antibody, for measurement of TSH (Thyroid Stimulating Hormone) in a sample.

A sample is a material, which may contain an analyte or analytes. In reference to the Bayer Diagnostics ACS:180® TSH3 Assay, the sample was serum, which might contain analyte. An analyte is a substance or substances, which may be present in a sample, and which can be qualitatively or quantitatively identified, assessed, characterized, detected or measured in an assay.

In reference to the Bayer Diagnostics ACS:180® TSH3 Assay, the analyte is TSH. Both the high quantum yield acridinium compounds and the control acridinium compound NSP-DMAE-HEG-glutarate were labels conjugated to a antibodies.

In reference to the Bayer Diagnostics ACS:180® TSH3 Assay, there are two antibodies, one of which is labeled with the acridinium compound and is called the tracer while the other is covalently attached to paramagnetic particles (PMP) solid phase.

In the ACS:80® TSH3 Assay, the assay mixture contains sample, tracer and solid phase, and the assay reaction is the action of the tracer and solid phase on the sample, which may contain analyte. Since the tracer binds to the analyte and the analyte is bound to the solid phase, a three-part 'sandwich' is formed of tracer, analyte and solid phase.

Consequently, the presence of analyte in a sample will cause the binding of the tracer through the analyte to the solid phase in the assay reaction mixture, where the amount of tracer bound to the solid phase depends on the amount of analyte present in the sample.

The Bayer Diagnostics ACS:180® automatically performed the following steps for the TSH3 Assay. First, 200 μL of each of twelve samples was dispensed into a separate cuvet. A cuvet is an optically transparent or translucent container that holds the assay reaction mixture and in which the assay reaction takes place. The twelve samples each contained separate known amounts of TSH.

The amounts of TSH given as concentrations in each of these twelve samples were 0, 0.002, 0.004, 0.010, 0.015, 0.020, 0.025, 0.030, 0.10, 1.0, 10 and 100 mIU/L. Next, the Bayer Diagnostics ACS:180® dispensed two assay reagents together into each cuvet and mixed the assay reagents with the sample within each cuvet.

The first of the two assay reagents was 0.100 mL of tracer, which contained 0.22 picomoles of anti-TSH antibody conjugated with acridinium compound. Both the high quantum yield acridinium compounds and the control acridinium compounds NSP-DMAE-HEG-glutarate were tested separately as labels conjugated to anti-TSH antibody. The assay reaction proceeded for 2,5 minutes at 37° C.

The second of the two assay reagents was 0.225 mL of solid phase, which was anti-TSH antibody conjugated to paramagnetic microparticles. The assay reaction proceeded for 5.0 minutes at 37° C. The assay reaction proceeded for a total of 7.5 minutes at 37° C.

The Bayer Diagnostics ACS:180® finished the ACS:180® TSH3 Assay by magnetically separating the solid phase from other assay reagents, then removing fluid from the cuvet and then washing the solid phase in the cuvet with water.

Chemiluminescence from acridinium compound on the solid phase was initiated with subsequent light emission with sequential additions of 0.30 mL each of Bayer Diagnostics ACS:180® Reagent 1 and Bayer Diagnostics ACS:180® Reagent 2. Bayer Diagnostics ACS:180® Reagent 1 was 0.1 M nitric acid and 0.5% hydrogen peroxide. Bayer Diagnostics ACS:180® Reagent 2 was 0.25 M sodium hydroxide and 0.05% cetyltrimethylammonium chloride.

The Bayer Diagnostics ACS:180® measured the chemiluminescence as relative light units (RLUs) in each cuvet with each cuvet corresponding to a single assayed sample. In the assay, the amount of analyte is correlated to the amount of tracer that will bind to the solid phase.

Consequently, the amount of analyte is correlated to the number of RLUs measured by the Bayer Diagnostics ACS:180®. This means that the greater the amount of the analyte TSH in a sample, then the greater the amount of RLUs are measured with respect to lower amounts of the analyte TSH in a sample where fewer RLUs are measured.

The high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced chemiluminescence for all amounts of analyte.

Noise is the portion of chemiluminescence in a sandwich immunoassay of a sample which is due to tracer that binds nonspecifically to the solid phase and which is measured in samples that contain no analyte. Signal is the portion of the chemiluminescence due to the specific binding of the tracer to the solid phase when analyte is present in the sample.

The total chemiluminescence measured in the Bayer Diagnostics ACS:180® TSH3 Assay for samples that do contain analyte is the sum of signal plus noise, where signal is calculated as the difference of the total chemiluminescence minus the noise.

Assay sensitivity is often defined as the least measurable amount of analyte. For the Bayer Diagnostics ACS:180® TSH3 Assay, which is a sandwich immunoassay, sensitivity is the least measurable non-zero amount of analyte. The least measurable non-zero amount of analyte is the amount of analyte corresponding to the least measured chemiluminescence that is greater than the sum of the noise plus two-standard deviations of the noise.

In the Bayer Diagnostics ACS:180® TSH3 Assay signal and noise were determined for each tested tracer. The ratio of the signal divided by the noise in a sandwich immunoassay for a particular amount of analyte is an indicator of sandwich immunoassay sensitivity. The greater the signal to noise ratio for a particular amount of analyte in a sandwich immunoassay, the more distant is the corresponding signal from the noise and the better able is the assay to measure the difference between the signal and the noise.

In the current assay, the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced signal to noise ratios for amounts of analyte relative to the control acridinium compound label NSP-DMAE-HEG-glutarate.

The greater signal to noise ratios generated by the high quantum yield acridinium compound labels for both the high amounts and particularly the low amounts of TSH, relative to the control acridinium compounds DMAE and NSP-DMAE-HEG-glutarate, indicate an enhancement of sensitivity for the Bayer Diagnostics ACS:180® TSH3 Assay using high quantum yield acridinium compound as immunoassay labels.

The slope of the line generated for each tracer using the Bayer Diagnostics ACS:180® TSH3 Assay is an indicator of sensitivity. The greater the slope of the line for a particular tracer or label in a sandwich immunoassay, the more distant is the signal for a particular amount of analyte from the noise and the better able is the assay to measure the difference between the signal and the noise.

In the current assay, the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate gave enhanced slopes relative to the control acridinium compound label NSP-DMAE-HEG-glutarate.

The greater slopes generated by the high quantum yield acridinium compound labels for both the high amounts and particularly the low amounts of TSH, relative to the control acridinium compounds DMAE and NSP-DMAE-HEG-glutarate, indicate an enhancement of sensitivity for the Bayer Diagnostics ACS:180® TSH3 Assay using high quantum yield acridinium compound as immunoassay labels.

The sensitivities measured for the Bayer Diagnostics ACS:180® TSH3 Assay using the high quantum yield acridinium compound labels NSP-2,7-(OMTEG)$_2$-DMAE, NSP-2,7-(OMTEG)$_2$-DMAE-HEG-glutarate, NSP-2,7-(OMHEG)$_2$-DMAE-AC and NSP-2,7-(OMHEG)$_2$-DMAE-HEG-glutarate were enhanced over the sensitivities measured using for the control acridinium compound NSP-DMAE-HEG-glutarate.

Assay sensitivity is often defined as the least measurable amount of analyte. In the current sandwich immunoassay the least measurable non-zero amount of analyte is the amount of analyte corresponding to the least measured chemiluminescence that is greater than the sum of the noise plus two-standard deviations of the noise.

For example, in sandwich immunoassays where the following representations are given:

n=positive integer greater than 0.

x=the measured amount of analyte corresponding to y, where $x0<x1<x2<x3< \ldots <xn$ are successively greater measured amounts of analyte.

y=the chemiluminescence measured for an amount of analyte, represented by x, where $y0<y1<y2<y3< \ldots <yn$ are successively greater values of chemiluminescence, measured for $x0<x1<x2<x3< \ldots <xn$, respectively.

x0=a zero amount of analyte or the amount of analyte equal to zero.

y0=the chemiluminescence measured for an amount of analyte equal to zero, which is x0.

s=one standard deviation of y0.

Then the sensitivity=xn for $yn>y0+2s$, when n=the least, positive, nonzero integer.

High quantum yield acridinium compounds enhanced the sensitivity of the Bayer Diagnostics ACS:180® TSH3 Assay 1.5- to 7.5-fold when compared to the control acridinium compound NSP-DMAE-HEG-glutarate. The example establishes that when used as chemiluminescent immunoassay labels the enhanced chemiluminescent light emission from high quantum yield acridinium compounds enhances the sensitivity of sandwich immunoassays.

DEFINITIONS

Analog: A chemical compound with some structural similarity to another different compound.

Analyte: A substance or substances in a sample to be identified, assessed, characterized, detected or measured in an assay.

Assay: The method, the reaction or the act of qualitative or quantitative identification, assessment, characterization, detection or measurement of the properties or amount of a substance, substances, analyte or analytes or their parts; and is synonymous with test.

Antigen: A substance which elicits the production of antibodies, or an immune system response, generally against a specific determinant or determinants.

Antibody (immunoglobulins, immune gamma globulin, immune globulin, immune serum globulin, immunoglobulin): a protein which can normally bind antigen thus producing an immune response.

Assay Reaction: the action of assay reagents on a sample in an assay.

Assay Reaction Mixture: a mixture of sample and assay reagents in an assay or assay reaction.

Carrier: A substance, generally a macromolecule, conjugated or complexed to one or more antigens, atoms, compounds, epitopes, haptens, ions, labels, ligands, molecules, radicals or receptors.

Competitive Immunoassay (generally synonymous with Competitive Binding Assay, Ligand Assay, Ligand-receptor Assay, Hapten Assay, Saturation Binding Assay): A subset of immunoassay where the amount of receptor is less than the amount of ligand and is based on the competitive binding, between a labeled ligand (tracer) and an unlabeled ligand (analyte) for a receptor, or based on the competitive binding between an immobilized ligand and a non-immobilized ligand (analyte) for a labeled receptor.

Complex: a non-covalent union of one or more atoms, molecules, compounds, ions or radicals with one or more atoms, molecules, compounds, ions or radicals.

Complexation: formation of a complex.

Conjugate: the act of or a covalent union of a molecule or molecules, compound or compounds with one or more atoms, molecules, compounds, ions or radicals forming a new molecule.

Conjugation: formation of a conjugate.

Determinant: a specific molecule or feature on the surface of a microbe or macromolecule that triggers an immune response.

Epitope: a specific site on a macromolecule to which a specific antibody can bind.

Hapten: a small molecule which cannot itself initiate an immune response but can act as an antigen when complexed or conjugated to a larger carrier and can thus initiate specific antibody production to which it can subsequently be bound.

Heterogeneous Immunoassay: immunoassay method which includes steps for separation of bound substances form unbound substances.

Homogeneous Immunoassay: immunoassay method which has no steps for separation of bound substances form unbound substances.

Immunoassay: the method, the reaction or the act of qualitative or quantitative identification, assessment, characterization, detection or measurement of the properties or amount of a substance or an analyte or its parts by action of an antigen, epitope, hapten, ligand, carrier, or macromolecule with a receptor which is usually an antibody or other biological receptor; and is synonymous with immunologic assay or immunochemical assay.

Label: an atom, molecule, compound, ion, radical or macromolecule that when conjugated or complexed to a ligand or to a receptor enables qualitative or quantitative identification, assessment, detection or measurement of an analyte in an assay.

Ligand: an atom, molecule, compound, ion or radical that binds specifically to a macromolecule (e.g. a hormone is a ligand for its receptor).

Macromolecule: a large molecule generally with a molecular weight greater than 1,000 daltons.

Sample: biological material which potentially contains an analyte or analytes.

Tracer: an immunoassay reagent made of a conjugate or complex of a label with a ligand or a receptor, which by action of the label, enables qualitative or quantitative identification, assessment, detection or measurement of an analyte in an assay.

Receptor: a macromolecule which can bind specifically one or more antigens, atoms, compounds, epitopes, haptens, ions, labels, ligands, molecules, radicals, other receptors or tracers.

We claim:

1. A reagent for the detection or quantification of an analyte comprising a hydrophilic, high quantum yield acridinium sulfonamide compound attached to an analyte, an analyte analog, or a binding molecule for an analyte; wherein the acridinium sulfonamide compound comprises a sulfonamide linkage at C-9 position of the acridinium ring and an electron-donating functional groups of the form —OR*, where R* is a group comprising a sulfopropyl moiety or ethylene glycol moieties, or a combination thereof, at the C-2 and/or the C-7 position of the acridinium ring, wherein the high quantum yield acridinium sulfonamide compound has a relative quantum light yield greater than 1 as compared with a corresponding acridinium sulfonamide compound without electron-donating functional groups at the C-2 and/or the C-7 position of the acridinium ring.

2. The reagent of claim 1, wherein the electron donating functional group at the C-2 and/or the C-7 position is —OCH$_2$CH$_2$CH$_2$SO$_3^-$ or —O(CH$_2$CH$_2$O)$_n$—CH$_2$—CH$_2$—OMe, wherein n=0-5.

3. The reagent of claim 1, wherein said acridinium compound comprises said electron-donating functional groups at the C-2 and the C-7 position of the acridinium ring.

4. A heterogeneous immunoassay for the quantification of a macromolecular analyte comprising:
   a) providing a conjugate of a binding molecule specific for a macromolecular analyte with a hydrophilic, high quantum yield chemiluminescent acridinium sulfonamide compound comprising a sulfonamide linkage at C-9 position of the acridinium ring and containing electron donating functional groups of the form —OR*, where R* is a group comprising a sulfopropyl moiety or ethylene glycol moieties, or a combination thereof, at the C-2 and/or C-7 position of the acridinium ring;
   b) providing a solid phase immobilized with a second binding molecule specific for said macromolecular analyte;
   c) mixing the conjugate, the solid phase and a sample suspected of containing the analyte to form a binding complex;
   d) separating the binding complex captured on the solid phase;
   e) triggering the chemiluminescence of the binding complex of d) by adding chemiluminescence triggering reagents;
   f) measuring the amount of light emission with a luminometer; and
   g) detecting the presence or calculating the concentration of the analyte by comparing the amount of light emitted from the reaction mixture with a standard dose response curve which relates the amount of light emitted to a known concentration of the analyte.

5. A heterogeneous immunoassay for the quantification of a small molecule analyte comprising:
   (a) providing a conjugate of an analyte or an analyte analog with a hydrophilic, high quantum yield chemiluminescent acridinium sulfonamide compound comprising a sulfonamide linkage at C-9 position of the acridinium ring and containing electron donating functional groups of the form —OR*, where R* is a group comprising a sulfopropyl moiety or ethylene glycol moieties, or a combination thereof, at the C-2 and/or C-7 position of the acridinium ring;
   (b) providing a solid phase immobilized with a binding molecule specific for the analyte;
   (c) mixing the conjugate, solid phase and a sample suspected of containing the analyte to form a binding complex;
   (d) separating the binding complex captured on the solid phase;
   (e) triggering the chemiluminescence of the binding complex of d) by adding chemiluminescence triggering reagents;
   (f) measuring the amount of light with an luminometer; and
   (g) detecting the presence or calculating the concentration of the analyte by comparing the amount of light emitted from the reaction mixture with a standard dose response curve which relates the amount of light emitted to a known concentration of the analyte.

6. A heterogeneous immunoassay for the quantification of a small molecule analyte comprising:
   (a) providing a solid phase immobilized with an analyte or an analyte analog;
   (b) providing a conjugate of a binding molecule specific for the analyte with a hydrophilic, high quantum yield chemiluminescent acridinium sulfonamide compound comprising a sulfonamide linkage at C-9 position of the acridinium ring and containing electron donating functional groups of the form —OR*, where R* is a group comprising a sulfopropyl moiety or ethylene glycol moieties, or a combination thereof, at the C-2 and/or C-7 position of the acridinium ring;
   (c) mixing the solid phase, the conjugate and a sample suspected containing the analyte to form a binding complex;
   (d) separating the binding complex captured on the solid phase;
   (e) triggering the chemiluminescence of the binding complex of d) by adding chemiluminescence triggering reagents;
   (f) measuring the amount of light with an luminometer; and
   (g) detecting the presence or calculating the concentration of the analyte by comparing the amount of light emitted from the reaction mixture with a standard dose response curve which relates the amount of light emitted to a known concentration of the analyte.

7. A hydrophilic, high quantum yield acridinium sulfonamide compound having the following structure:

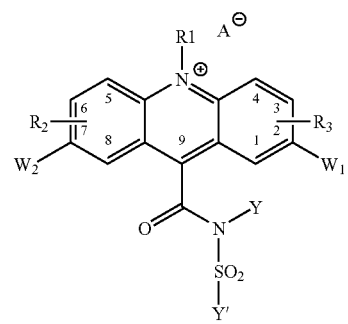

wherein, $R_1$ is an alkyl, alkenyl, alkynyl or aralkyl, wherein $R_1$ comprises up to 20 heteroatoms;

$R_2$ and $R_3$ are the same or different and are hydrogen, halides or R where R is an alkyl, alkenyl, alkynyl, aryl, or aralkyl, wherein R comprises up to 20 heteroatoms at positions other than C(2) and C(7);

$W_1$ and $W_2$ are the same or different and represent hydrogen or an electron-donating group of the form —OR*, where R* is a group comprising a sulfopropyl moiety or ethylene glycol moieties, or a combination thereof; with the proviso that at least one of $W_1$ and $W_2$ is said electron-donating group;

$A^-$ is a counter ion to pair with the quaternary nitrogen of said acridinium nucleus;

Y is a group —$R_9$—$R_{10}$, where $R_9$ is not required or is branched or straight-chained alkyl, substituted or unsubstituted aryl or aralkyl, each comprising up to 20 heteroatoms, and $R_{10}$ is a leaving group or an electrophilic functional group attached with a leaving group selected from the group consisting of:

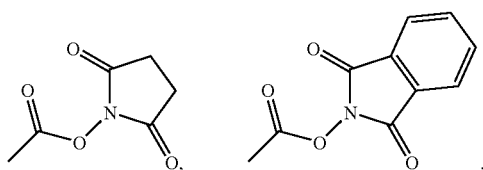

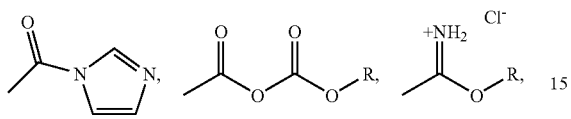

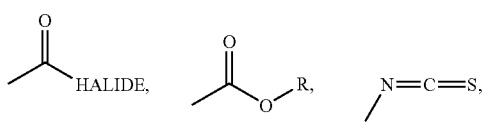

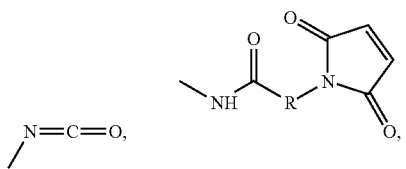

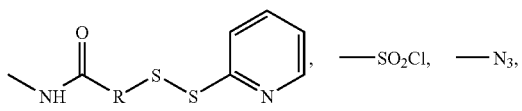

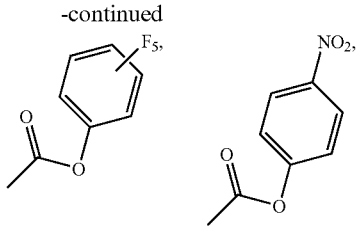

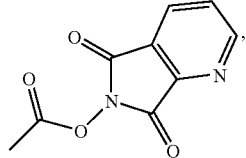

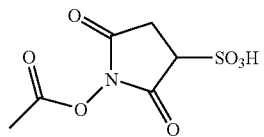

a halide or —COOH; or $R_{10}$ is a nucleophilic group —NH—R—NHR wherein R is independently hydrogen, alkyl, alkenyl, alkynyl, or aralkyl; each comprising up to 20 heteroatoms; and Y' is a substituted or unsubstituted aryl group or branched or straight chain alkyl group.

8. The hydrophilic, high quantum yield acridinium sulfonamide compound according to claim 7 having the following structure:

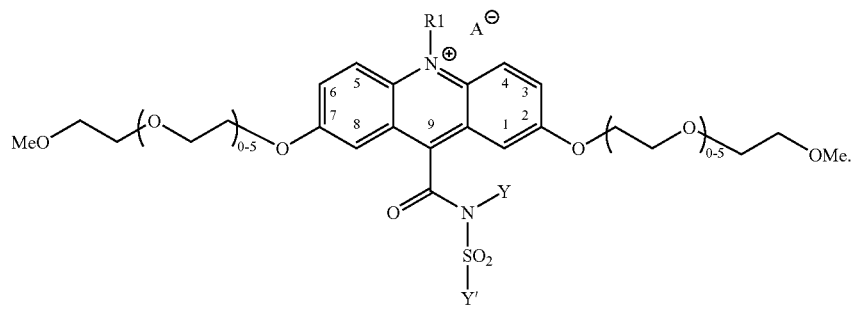

9. The hydrophilic, high quantum yield acridinium sulfonamide compound according to claim 8 having the following structure:

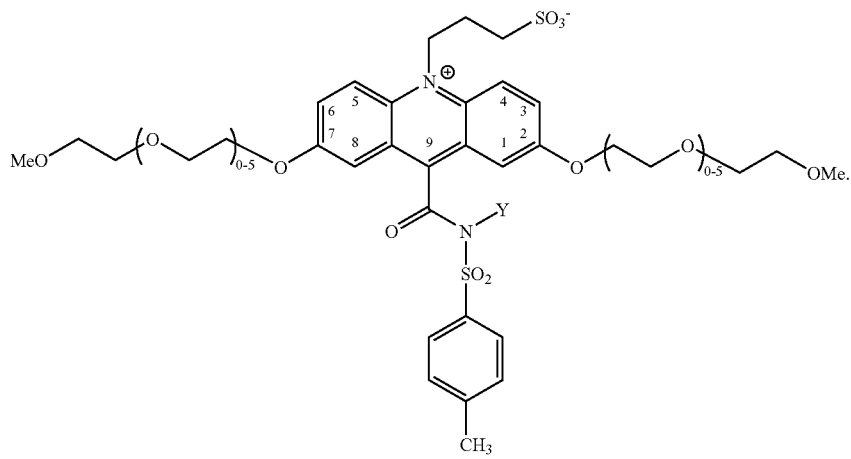

10. The hydrophilic, high quantum yield acridinium sulfonamide compound according to claim 9 having the following structure:

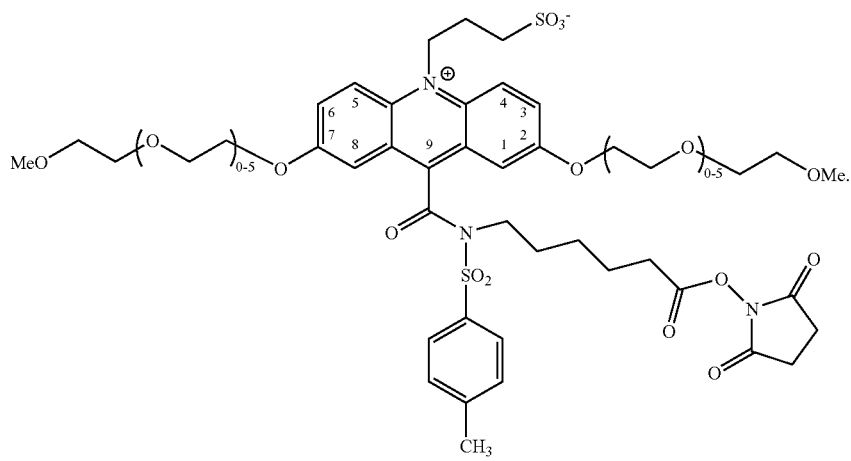

11. The heterogeneous immunoassay of claim 4, wherein the macromolecular analyte is selected from the group consisting of proteins, nucleic acids, oligosaccharides, antibodies, antibody fragments, cells, viruses, and synthetic polymers.

12. The heterogeneous immunoassay of claim 5, wherein the small molecule analyte is selected from the group consisting of steroids, vitamins, hormones, therapeutic drugs, and small peptides.

13. The heterogeneous immunoassay of claim 6, wherein the small molecule analyte is selected from the group consisting of steroids, vitamins, hormones, therapeutic drugs, and small peptides.

14. The heterogeneous immunoassay of claim 4, wherein the macromolecular analyte is thyroid stimulating hormone.

15. The heterogeneous immunoassay of claim 5, wherein the small molecule analyte is theophylline.

* * * * *